US009975926B2

(12) United States Patent
Puckette et al.

(10) Patent No.: US 9,975,926 B2
(45) Date of Patent: May 22, 2018

(54) METHODS OF MAKING AND USING VACCINES UTILIZING MINICIRCLE DNA EXPRESSION VECTORS FOR PRODUCTION OF FOOT-AND-MOUTH-DISEASE VIRUS PROTEINS AND VIRUS-LIKE PARTICLES

(71) Applicant: The United States of America, as Represented by the Secretary, Department of Homeland Security, Washington, DC (US)

(72) Inventors: Michael Puckette, Washington, DC (US); Max Rasmussen, Washington, DC (US); John Neilan, Washington, DC (US)

(73) Assignee: The United States of America, as represented by the Secretary of Homeland Security, Washington, DC (US)

( * ) Notice: Subject to any disclaimer, the term of this patent is extended or adjusted under 35 U.S.C. 154(b) by 0 days. days.

(21) Appl. No.: 14/962,272

(22) Filed: Dec. 8, 2015

(65) Prior Publication Data
US 2017/0158739 A1 Jun. 8, 2017

(51) Int. Cl.
C07K 14/005 (2006.01)
G01N 33/569 (2006.01)
A61K 39/00 (2006.01)

(52) U.S. Cl.
CPC ..... *C07K 14/005* (2013.01); *G01N 33/56983* (2013.01); *A61K 39/00* (2013.01); *C12N 2770/32122* (2013.01); *C12N 2770/32123* (2013.01); *C12N 2770/32134* (2013.01); *G01N 2333/09* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | | |
|---|---|---|---|---|
| 5,354,670 A | * | 10/1994 | Nickoloff | C12N 15/102 435/488 |
| 8,236,548 B2 | | 8/2012 | Chen et al. | |
| 2012/0258133 A1 | | 10/2012 | Charleston et al. | |
| 2012/0315295 A1 | * | 12/2012 | Rieder | A61K 39/135 424/205.1 |
| 2017/0158739 A1 | * | 6/2017 | Puckette | C07K 14/005 |

FOREIGN PATENT DOCUMENTS

WO    WO 2011/048353    *   4/2011

OTHER PUBLICATIONS

Rajasekhar et al. (Research in Veterinary Science. 2013; 95: 291-297).*
Montes et al. (Information and Computation. 2012; 213: 59-69).*
Sequence alignment of SEQ ID No. 4 with Geneseq database access No. AAA13691 by Iadarola et al. in WO20001680 on Jul. 2000.*
Sequence alignment of SEQ ID No. 5 with Geneseq database access No. AAC84000 by Prusiner et al. in WO 200068382 on Nov. 2000.*
Yang et al., "A novel minicircle vector based system for inhibiting the replication and gene expression of Enterovirus 71 and Coxsackievirus A16", Antiviral Research 96 (2012), p. 234-244.
Wang et al., "In Vivo Electroporation of Minicircle DNA as a novel method of vaccine delivery to enhance HIV-1-Specific Immune Responses", Journal of Virology, vol. 88, No. 4 (2014), p. 1924-1934.
de Crecy-Lagard, Valerie, "Identification of Genes Encoding tRNA Modification Enzymes by Comparative Genomics", Methods Enzymol, 2007, vol. 425, p. 153-183.
Green et al., "Characterization of the Mechanical unfolding of RNA Pseudoknots", J. Mol. Biol. (2008), vol. 375, p. 511-528.
Kay et al., "A robust system for production of minicircle DNA vectors", Nature Biotechnology, 2010, p. 1-5.
Kim et al., "Superluminescent variants of Marine Luciferases for Bioassays", Analytical Chemistry, 2011, vol. 83, p. 8732-8740.
Mayr et al., "Immune responses and protection against foot-and-mouth disease virus (FMDV) challenge in swine vaccinated with adenovirus-FMDV constructs", Vaccine, 19, 2001, p. 2152-2162.
Moraes et al., "Early protection against homologous challenge after a single dose of replication-defective human adenovirus type 5 expressing capsid proteins of foot-and-mouth disease virus (FMDV) strain A24", Vaccine, 20, 2002, p. 1631-1639.
Pacheco et al., "Rapid protecting of cattle from direct challenge with foot-and-mouth disease virus (FMDV) by a single inoculation with an adenovirus-vectored FMDV subunit vaccine", Virology, 337, 2005, p. 205-209.
Porta et al., "Efficient production of foot-and-mouth disease virus empty capsids in insect cells following down regulation of 3C protease activity", Journal of Virological Methods, 187, 2013, p. 406-412.

* cited by examiner (Continued)

Primary Examiner — Shanon A. Foley
(74) Attorney, Agent, or Firm — Lavanya Ratnam; Trenton Roche; Joseph Hsiao

(57) ABSTRACT

This application is directed generally to minicircle DNA vectors for the vaccination of foot-and-mouth disease (FMD). The transgene expression cassette in the minicircle DNA vector includes: a eukaryotic translation initiation nucleotide sequence, a mutant nucleotide sequence that encodes a foot-and-mouth disease virus (FMDV) capsid polyprotein precursor that contains at least one mutation to eliminate a restriction enzyme recognition site, a nucleotide sequence that encodes a protease that cleaves the FMDV capsid polyprotein precursor into a plurality of FMDV capsid proteins and a translational regulatory element to regulate the expression of the protease. The minicircle DNA vectors can be transfected directly into the cell of a mammalian host. When transfected into the mammalian host cell, virus-like particles can be produced intrinsically to stimulate the mammalian host's immune system to develop adaptive immunity toward foot-and-mouth disease.

7 Claims, 8 Drawing Sheets

FIG. 4 mc SGLuc mc O1P1-3C mc O1P1-HIV-3C(C142T)

SEQUENCE LISTING

<160> NUMBER OF SEQ ID NOS: 39

<210> SEQ ID NO 1
<211> LENGTH: 2259
<212> TYPE: DNA
<213> ORGANISM: Artificial Sequence
<220> FEATURE:
<223> OTHER INFORMATION: P1 polyprotein precursor from FMDV O1 Manisa
      isolate 87, mutated

<400> SEQUENCE: 1
ggagccgggc aatccagccc ggcaaccggg tcacagaacc aatcaggcaa cactgggagc      60
atcatcaaca attactacat gcagcagtac caaaactcta tggacacaca acttggtgac     120
aacgctacaa gcggaggctc aaacgagggg tccacggaca caacctccac ccacacaacc     180
aacactcaga caaacgactg gttctcgaag ctggccagtt ccgctttcag cggtcttttc     240
ggcgctcttc tcgccgacaa gaaaaccgag gagaccactc ttcttgagga ccgcatcctc     300
actactcgta acggacacac cacctcgaca acccagtcga gcgtaggagt cacatacggg     360
tatgcaacgg ctgaggattt cgtgagcggg ccaaacacct ctggtcttga gaccagggtt     420
gcccaggcag agcggttctt taaaacccac ctgttcgact gggtcacaag tgacccgttc     480
ggacggtgcc acctgctaga acttccaact gaccacaaag gtgtctatgg cagcctgacc     540
gactcgtatg cttatatgag gaacggctgg gatgttgaag tcactgctgt gggaaatcag     600
ttcaatggag gatgcctgtt ggtggctatg gtgccagaac tttgctccat acagaagagg     660
gagctgtacc agctcacgct ctttcctcac cagttcatca accctcggac gaacatgaca     720
gcacacatca ctgtgccctt tgttggcgtc aaccgttatg accagtacaa ggtacacaaa     780 ccttggacce tcgtggttat ggttgtagcc cccctgaccg tcaacagtga aggtgccccg     840
caaatcaagg tgtatgccaa catcgcacct accaacgtac acgtcgcggg tgagttccct     900
tccaaagagg ggatcttccc tgtggcttgc agcgatggtt atggcggtct ggtgacaact     960
gacccgaaaa cggctgaccc cgcttacggg aaagtgttta cccccccccg caacatgttg    1020
ccggggcggt tcaccaattt tcttgacgtg gctgaggcgt gccccacgtt tctccacttc    1080
gagggtgacg tgccatacgt gaccacgaag acggattcag acagggtgct cgctcagttc    1140
gacttgtctt tggcagcaaa gcacatgtcc aacaccttcc ttgcaggtct cgcccagtac    1200

| | |
|---|---|
| tacacacagt acagcggcac catcaacctg cacttcatgt tcacagggcc tactgacgcg | 1260 |
| aaggcgcgtt acatgattgc gtatgctcct cctggcatgg aaccacctaa aacgccagag | 1320 |
| gcggctgccc actgcatcca tgctgaatgg gacacagggt tgaactcaaa attcacattt | 1380 |
| tcaatccctt accttttcggc ggctgattac gcttacacag cgtctgacac tgctgagacc | 1440 |
| acaaatgtac agggatgggt ttgcctgttt caaataacac acgggaaagc tgacggcgac | 1500 |
| gcactggtcg ttttggccag cgccggaaag gactttgagc tgcgcctgcc ggtggatgct | 1560 |
| cgcacacaga ctacctcagc gggcgagtca gcagaccccg tgaccgccac cgttgagaat | 1620 |
| tacggtggcg agacacaggt ccagaggcgc aacacacgg acgtgtcatt tatattagac | 1680 |
| agatttgtga aagtgacacc aaaagaccaa attaatgtat tggacctgat gcaaaccccct | 1740 |
| gctcacactt tggtgggagc actccttcgt actgccactt actatttcgc tgacttagag | 1800 |
| gtggcagtga agcacgaggg aaacctcacc tgggtgccga acggggcgcc tgaagcggcg | 1860 |
| ttggacaaca ccaccaaccc aacagcttac cacaaggcac cactcacccg acttgcactg | 1920 |
| ccttacacgg cgccacaccg cgtgttggct actgtttaca acgggaacag caagtatggt | 1980 |
| gacggcacgg tggccaatgt gagaggtgat ctgcaagtgt tggcccagaa ggcggcgaga | 2040 |
| gcgctgccta cctccttcaa ctacggtgcc attaaagcta ctcgggtgac tgaactgcct | 2100 |
| taccgcatga gagggctga gacatactgt ccccggcctc ttttggccat tcacccggac | 2160 |
| caggctagac acaagcagaa gattgtggct ccggtgaaac agcttctaaa ttttgacctg | 2220 |
| ctcaaattgg cgggagatgt ggagtccaac cctgggccc | 2259 |

<210> SEQ ID NO 2
<211> LENGTH: 3059
<212> TYPE: DNA
<213> ORGANISM: Artificial Sequence
<220> FEATURE:
<223> OTHER INFORMATION: Transgene expression cassette
<400> SEQUENCE: 2

| | |
|---|---|
| ggatccgccg ccgccatggg agccgggcaa tccagcccgg caaccgggtc acagaaccaa | 60 |
| tcaggcaaca ctgggagcat catcaacaat tactacatgc agcagtacca aaactctatg | 120 |
| gacacacaac ttggtgacaa cgctacaagc ggaggctcaa cgagggggtc cacggacaca | 180 |
| acctccaccc acacaaccaa cactcagaac aacgactggt tctcgaagct ggccagttcc | 240 |
| gctttcagcg gtcttttcgg cgctcttctc gccgacaaga aaaccgagga gaccactctt | 300 |
| cttgaggacc gcatcctcac tactcgtaac ggacacacca cctcgacaac ccagtcgagc | 360 |
| gtaggagtca catacgggta tgcaacggct gaggatttcg tgagcgggcc aaacacctct | 420 |
| ggtcttgaga ccagggttgc ccaggcagag cggttctttta aacccacct gttcgactgg | 480 |
| gtcacaagtg acccgttcgg acggtgccac ctgctagaac ttccaactga ccacaaaggt | 540 |
| gtctatggca gcctgaccga ctcgtatgct tatatgagga acggctggga tgttgaagtc | 600 |
| actgctgtgg gaaatcagtt caatggagga tgcctgttgg tggctatggt gccagaactt | 660 |
| tgctccatac agaagaggga gctgtaccag ctcacgctct ttcctcacca gttcatcaac | 720 |
| cctcggacga acatgacagc acacatcact gtgcccttg ttggcgtcaa ccgttatgac | 780 |
| cagtacaagg tacacaaacc ttggaccctc gtggttatgg ttgtagcccc cctgaccgtc | 840 |
| aacagtgaag gtgccccgca aatcaaggtg tatgccaaca tcgcacctac caacgtacac | 900 |
| gtcgcgggtg agttcccttc caaagagggg atcttccctg tggcttgcag cgatggttat | 960 |
| ggcggtctgg tgacaactga cccgaaaacg gctgaccccg cttacgggaa agtgtttaac | 1020 |

```
cccccccgca acatgttgcc ggggcggttc accaattttc ttgacgtggc tgaggcgtgc    1080
cccacgtttc tccacttcga gggtgacgtg ccatacgtga ccacgaagac ggattcagac    1140
agggtgctcg ctcagttcga cttgtctttg gcagcaaagc acatgtccaa caccttcctt    1200
gcaggtctcg cccagtacta cacacagtac agcggcacca tcaacctgca cttcatgttc    1260
acagggccta ctgacgcgaa ggcgcgttac atgattgcgt atgctcctcc tggcatggaa    1320
ccacctaaaa cgccagaggc ggctgccccac tgcatccatg ctgaatggga cagggttg     1380 aactcaaaat tcacattttc aatcccttac ctttcggcgg ctgattacgc ttacacagcg    1440
tctgacactg ctgagaccac aaatgtacag ggatgggttt gcctgtttca ataacacac    1500 gggaaagctg acggcgacgc actggtcgtt ttggccagcg ccggaaagga ctttgagctg    1560
cgcctgccgg tggatgctcg cacacagact acctcagcgg gcgagtcagc agaccccgtg    1620
accgccaccg ttgagaatta cggtggcgag acacaggtcc agaggcgcca acacacggac    1680
gtgtcattta tattagacag atttgtgaaa gtgacaccaa aagaccaaat taatgtattg    1740
gacctgatgc aaacccctgc tcacactttg gtgggagcac tccttcgtac tgccacttac    1800
tatttcgctg acttagaggt ggcagtgaag cacgagggaa acctcacctg ggtgccgaac    1860
ggggcgcctg aagcggcgtt ggacaacacc accaacccaa cagcttacca caaggcacca    1920
ctcacccgac ttgcactgcc ttacacgcg ccacaccgcg tgttggctac tgtttacaac     1980
gggaacagca agtatggtga cggcacggtg gccaatgtga gaggtgatct gcaagtgttg    2040
gcccagaagg cggcgagagc gctgcctacc tccttcaact acggtgccat taaagctact    2100
cgggtgactg aactgctttta ccgcatgaag agggctgaga catactgtcc ccggcctctt    2160
ttggccattc acccggacca ggctagacac aagcagaaga ttgtggctcc ggtgaaacag    2220
cttctaaatt ttgacctgct caaattggcg ggagatgtgg agtccaaccc tgggcccagc    2280
ggccgcggac cttttttagg gaagatctgg ccttcctaca agggaaggcc agggaatttt    2340
cttacgaggg accggtaaaa aaacccgtag cactcaaggt taaagcaaag aatctcattg    2400
ttaccgaaag tggagcccca ccgaccgact tgcaaaagat ggtcatgggc aacaccaagc    2460
ctgttgaact catcctcgac gggaagacgg tggccatttg ttgtgctacc ggtgtgtttg    2520
gcactgcgta cctcgtgcct cgtcatcttt ttgcagaaaa atatgacaag atcatgctgg    2580
acggcagagc catgacagac agtgactaca gagtgtttga gtttgagatt aaagtaaaag    2640
gacaggacat gctctcagac gctgcgctca tggtactcca ccgtgggaat cgcgtgagag    2700
acatcacgaa acactttcgt gacacagcaa gaatgaagaa aggcacccct gttgtcggag    2760
taatcaacaa tgccgacgtc gggagactga tcttctctgg tgaggccctt acctacaagg    2820
acattgtagt gacaatggat ggagacacca tgcctggcct gtttgcctac aaagccgcca    2880
ccaaggctgg ctactgtggg ggagccgttc ttgctaagga cggagctgac acattcatcg    2940
ttggcactca ctccgcaggc ggcaatggag ttggatactg ctcatgcgtt ccaggtcca    3000 tgttgctgaa aatgaaggcg cacatcgacc ccgaaccaca ccacgagaag taagaattc    3059
```

<210> SEQ ID NO 3
<211> LENGTH: 4788
<212> TYPE: DNA
<213> ORGANISM: Artificial Sequence
<220> FEATURE:
<223> OTHER INFORMATION: pMC-CMV-SV40-polyA O1P1-HIV-3C(C142T)(without bacterial backbone)

<400> SEQUENCE: 3

```
cccttgggct ccccgggcgc gactagtgaa ttgatactag tattatgccc agtacatgac      60
cttatgggac tttcctactt ggcagtacat ctacgtatta gtcatcgcta ttaccatggt     120
gatgcggttt tggcagtaca tcaatgggcg tggatagcgg tttgactcac ggggatttcc     180
aagtctccac cccattgacg tcaatgggag tttgttttgg caccaaaatc aacgggactt     240
tccaaaatgt cgtaacaact ccgccccatt gacgcaaatg ggcggtaggc gtgtacggtg     300
ggaggtttat ataagcagag ctcgtttagt gaaccgtcag atcgcctgga gacgccatcc     360
acgctgtttt gacctccata gaagattcta gagtcgacgc ggccgcggat ccgccgccgc     420
catgggagcc gggcaatcca gcccggcaac cgggtcacag aaccaatcag caacactgg      480
gagcatcatc aacaattact acatgcagca gtaccaaaac tctatggaca cacaacttgg     540
tgacaacgct acaagcggag gctcaaacga ggggtccacg gacacaacct ccacccacac     600
aaccaacact cagaacaacg actggttctc gaagctggcc agttccgctt tcagcggtct     660
tttcggcgct cttctcgccg acaagaaaac cgaggagacc actcttcttg aggaccgcat     720
cctcactact cgtaacggac acaccacctc gacaacccag tcgagcgtag gagtcacata     780
cgggtatgca acggctgagg atttcgtgag cgggccaaac acctctggtc ttgagaccag     840
ggttgcccag gcagagcggt tctttaaaac ccacctgttc gactgggtca aagtgacccc     900
gttcggacgg tgccacctgc tagaacttcc aactgaccac aaaggtgtct atggcagcct     960
gaccgactcg tatgcttata tgaggaacgg ctgggatgtt gaagtcactg ctgtgggaaa    1020
tcagttcaat ggaggatgcc tgttggtggc tatggtgcca gaactttgct ccatacagaa    1080
gagggagctg taccagctca cgctctttcc tcaccagttc atcaaccctc ggacgaacat    1140
gacagcacac atcactgtgc cctttgttgg cgtcaaccgt tatgaccagt acaaggtaca    1200
caaaccttgg accctcgtgg ttatggttgt agccccctg accgtcaaca gtgaaggtgc     1260
cccgcaaatc aaggtgtatg ccaacatcgc acctaccaac gtacacgtcg cgggtgagtt    1320
cccttccaaa gagggatct tccctgtggc ttgcagcgat ggttatggcg gtctggtgac     1380
aactgacccg aaaacggctg accccgctta cgggaaagtg tttaacccccc cccgcaacat    1440
gttgccgggg cggttcacca atttttcttga cgtggctgag gcgtgcccca cgtttctcca    1500
cttcgagggt gacgtgccat acgtgaccac gaagacggat tcagacaggg tgctcgctca    1560
gttcgacttg tctttggcag caaagcacat gtccaacacc ttccttgcag gtctcgccca    1620
gtactacaca cagtacagcg gcaccatcaa cctgcacttc atgttcacag gcctactga     1680
cgcgaaggcg cgttacatga ttgcgtatgc tcctcctggc atggaaccac ctaaaacgcc    1740
agaggcggct gcccactgca tccatgctga atgggacaca gggttgaact caaaattcac    1800
attttcaatc ccttacccttt cggcggctga ttacgcttac acagcgtctg acactgctga    1860
gaccacaaat gtacagggat gggttttgcct gtttcaaata acacacggga agctgacgg     1920
cgacgcactg tcgttttgg ccagcgccgg aaaggacttt gagctgcgcc tgccggtgga    1980
tgctcgcaca cagactacct cagcgggcga gtcagcagac cccgtgaccg ccaccgttga    2040
gaattacggt ggcgagacac aggtccagag gcgccaacac acggacgtgt catttatatt    2100
agacagattt gtgaaagtga caccaaaaga ccaaattaat gtattggacc tgatgcaaac    2160
ccctgctcac actttggtgg gagcactcct tcgtactgcc acttactatt tcgctgactt    2220
agaggtggca gtgaagcacg agggaaacct cacctgggtg ccgaacgggg cgcctgaagc    2280
ggcgttggac aacaccacca acccaacagc ttaccacaag gcaccactca cccgacttgc    2340
```

```
actgccttac acggcgccac accgcgtgtt ggctactgtt tacaacggga acagcaagta    2400
tggtgacggc acggtggcca atgtgagagg tgatctgcaa gtgttggccc agaaggcggc    2460
gagagcgctg cctacctcct tcaactacgg tgccattaaa gctactcggg tgactgaact    2520
gctttaccgc atgaagaggg ctgagacata ctgtccccgg cctcttttgg ccattcaccc    2580
ggaccaggct agacacaagc agaagattgt ggctccggtg aaacagcttc taaattttga    2640
cctgctcaaa ttggcgggag atgtggagtc aacccctggg cccagcggcc gcggaccttt    2700
tttagggaag atctggcctt cctacaaggg aaggccaggg aattttctta cgagggaccg    2760
gtaaaaaaac ccgtagcact caaggttaaa gcaaagaatc tcattgttac gaaagtgga    2820
gccccaccga ccgacttgca aagatggtc atgggcaaca ccaagcctgt tgaactcatc    2880
ctcgacggga agacggtggc catttgttgt gctaccggtg tgtttggcac tgcgtacctc    2940
gtgcctcgtc atcttttgc agaaaaatat gacaagatca tgctggacgg cagagccatg    3000
acagacagtg actacagagt gtttgagttt gagattaaag taaaggaca ggacatgctc    3060
tcagacgctg cgctcatggt actccaccgt gggaatcgcg tgagagacat cacgaaacac    3120
tttcgtgaca cagcaagaat gaagaaaggc acccctgttg tcggagtaat caacaatgcc    3180
gacgtcggga gactgatctt ctctggtgag gcccttacct acaaggacat tgtagtgaca    3240
atggatggag acaccatgcc tggcctgttt gcctacaaag ccgccaccaa ggctggctac    3300
tgtgggggag ccgttcttgc taaggacgga gctgacacat tcatcgttgg cactcactcc    3360
gcaggcggca atggagttgg atactgctca tgcgtttcca ggtccatgtt gctgaaaatg    3420
aaggcgcaca tcgaccccga accacaccac gagaagtaag aattcgagct cgacaatcaa    3480
cctctggatt acaaaatttg tgaaagattg actggtattc ttaactatgt tgctcctttt    3540
acgctatgtg gatacgctgc tttaatgcct ttgtatcatg ctattgcttc ccgtatggct    3600
ttcattttct cctccttgta taaatcctgg ttgctgtctc tttatgagga gttgtggccc    3660
gttgtcaggc aacgtggcgt ggtgtgcact gtgtttgctg acgcaacccc cactggttgg    3720
ggcattgcca ccacctgtca gctcctttcc gggactttcg ctttccccct ccctattgcc    3780
acggcggaac tcatcgccgc ctgccttgcc cgctgctgga caggggctcg gctgttgggc    3840
actgacaatt ccgtggtgtt gtcggggaaa tcatcgtcct ttccttggct gctcgcctgt    3900
gttgccacct ggattctgcg cgggacgtcc ttctgctacg tcccttcggc cctcaatcca    3960
gcggaccttc cttcccgcgg cctgctgccg gctctgcggc ctcttccgcg tcttcgcctt    4020
cgccctcaga cgagtcggat ctccctttgg gccgcctccc cgcctggtac ctttaagacc    4080
aatgacttac aaggcagctg tagatcttag ccacttttta aaagaaaagg ggggactgga    4140
agggctaatt cactcccaac gaagataaga tctgcttttt gcttgtactg ggtctctctg    4200
gttagaccag atctgagcct gggagctctc tggctaacta gggaacccac tgcttaagcc    4260
tcaataaagc ttgccttgag tgcttcaagt agtgtgtgcc cgtctgttgt gtgactctgg    4320
taactagaga tccctcagac ccttttagtc agtgtggaaa atctctagca gtagtagttc    4380
atgtcatctt attattcagt atttataact tgcaaagaaa tgaatatcag agagtgagag    4440
gaacttgttt attgcagctt ataatggtta caaataaagc aatagcatca caaatttcac    4500
aaataaagca tttttttcac tgcattctag ttgtggtttg tccaaactca tcaatgtatc    4560
ttatcatgtc tggctctagc tatcccgccc ctaactccgc ccatcccgcc cctaactccg    4620
cccagttccg cccattctcc gccccatggc tgactaattt tttttattta tgcagaggcc    4680
gaggccgcct cggcctctga gctattccag aagtagtgag gaggcttttt tggaggccta    4740
```

```
gacttttgca gatcgaccca tgggggcccg ccccaactgg ggtaacct           4788
```

<210> SEQ ID NO 4
<211> LENGTH: 13
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (7)..(7)
<223> OTHER INFORMATION: r is g or a

<400> SEQUENCE: 4

```
gccgccrcca tgg                                                 13
```

<210> SEQ ID NO 5
<211> LENGTH: 13
<212> TYPE: DNA
<213> ORGANISM: Artificial Sequence
<220> FEATURE:
<223> OTHER INFORMATION: Kozak eukaryotic translation initiation
      sequence

<400> SEQUENCE: 5

```
gccgccgcca tgg                                                 13
```

<210> SEQ ID NO 6
<211> LENGTH: 120
<212> TYPE: DNA
<213> ORGANISM: Human immunodeficiency virus
<220> FEATURE:
<221> NAME/KEY: misc_feature
<223> OTHER INFORMATION: Human immunodeficiency virus frameshift element

<400> SEQUENCE: 6

```
acctttttta gggaagatct ggccttccta caagggaagg ccagggaatt ttcttacgag    60
ggaccggtaa aaaacccgt agcactcaag gttaaagcaa agaatctcat tgttaccgaa    120
```

<210> SEQ ID NO 7
<211> LENGTH: 642
<212> TYPE: DNA
<213> ORGANISM: Foot-and-mouth disease virus
<220> FEATURE:
<221> NAME/KEY: misc_feature
<223> OTHER INFORMATION: Foot-and-mouth disease virus - WT Asia Lebanon
      89 3C protease sequence

<400> SEQUENCE: 7

```
agtggtgccc caccgaccga cttgcaaaag atggtcatga gcaacactaa gcctgttgag    60
ctcatccttg acgtaagac ggtggccatc tgctgcgcca ccggagtgtt tggtactgcc    120
tacctcgtgc ctcgtcacct tttcgcagaa aagtacgaca ggatcatgtt ggacggcagg    180
gccatgacag acagtgacta cagagtgttt gagtttgaga ttaaagtaaa aggacaggac    240
atgctctcag acgctgcgct catggtgctc caccgtggca accgtgtgag agacatcacg    300
aaacactttc gtgatacagc aagaatgaag aaaggtaccc ccgttgtcgg cgtgatcaac    360
aacgccgacg ttgggagact gattttctcc ggtgaggccc tcacctacaa ggacattgta    420
gtgtgcatgg atggagacac catgccgggc ctatttgcct acagagccgc taccaaggct    480
ggctactgtg gaggagccgt tcttgccaag acggagctg acacatttat cgtcggcact    540
cactccgcag gaggcaatgg agtcgggtac tgctcatgcg tatctaggtc catgctcttg    600
```
aagatgaagg cacacattga ccccgaacca caccacgagt ag                642

<210> SEQ ID NO 8
<211> LENGTH: 214
<212> TYPE: PRT
<213> ORGANISM: Foot-and-mouth disease virus
<220> FEATURE:
<221> NAME/KEY: MISC_FEATURE
<223> OTHER INFORMATION: Foot-and-mouth disease virus - WT Asia Lebanon
      89 3C protease sequence

<400> SEQUENCE: 8

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Thr Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu Lys
    210

<210> SEQ ID NO 9
<211> LENGTH: 642
<212> TYPE: DNA
<213> ORGANISM: Artificial Sequence
<220> FEATURE:
<223> OTHER INFORMATION: FMDV A22 Iraq strain 3C protease with C142T
      mutation

<400> SEQUENCE: 9
agtggagccc caccgaccga cttgcaaaag atggtcatgg gcaacaccaa gcctgttgaa     60
ctcatcctcg acgggaagac ggtggccatt tgttgtgcta ccggtgtgtt tggcactgcg    120
tacctcgtgc ctcgtcatct ttttgcagaa aaatatgaca agatcatgct ggacggcaga    180
gccatgacag acagtgacta cagagtgttt gagtttgaga ttaaagtaaa aggacaggac    240
atgctctcag acgctgcgct catggtactc caccgtggga atcgcgtgag agacatcacg    300
aaacactttc gtgacacagc aagaatgaag aaaggcaccc ctgttgtcgg agtaatcaac    360

```
aatgccgacg tcgggagact gatcttctct ggtgaggccc ttacctacaa ggacattgta      420
gtgacaatgg atggagacac catgcctggc ctgtttgcct acaaagccgc caccaaggct      480
ggctactgtg ggggagccgt tcttgctaag gacggagctg acacattcat cgttggcact      540
cactccgcag gcggcaatgg agttggatac tgctcatgcg tttccaggtc catgttgctg      600
aaaatgaagg cgcacatcga ccccgaacca caccacgaga ag                        642
```

<210> SEQ ID NO 10
<211> LENGTH: 214
<212> TYPE: PRT
<213> ORGANISM: Artificial Sequence
<220> FEATURE:
<223> OTHER INFORMATION: FMDV A22 Iraq strain 3C protease with C142T
      mutation

<400> SEQUENCE: 10

```
Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Thr Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu Lys
    210
```

<210> SEQ ID NO 11
<211> LENGTH: 2259
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV O1 Manisa isolate 87

<400> SEQUENCE: 11

```
ggagccgggc aatccagccc ggcaaccggg tcacagaacc aatcaggcaa cactgggagc       60
atcatcaaca attactacat gcagcagtac caaaactcca tggacacaca acttggtgac      120
```

```
aacgctacaa gcggaggctc aaacgagggg tccacggaca caacctccac ccacacaacc    180
aacactcaga acaacgactg gttctcgaag ctggccagtt ccgctttcag cggtcttttc    240
ggcgctcttc tcgccgacaa gaaaaccgag gagaccactc ttctagagga ccgcatcctc    300
actactcgta acggacacac cacctcgaca acccagtcga gcgttggagt cacgtacggg    360
tatgcaacag ctgaggattt cgtgagcggg ccaaacacct ctggtctcga gaccagggtt    420
gcccaggcag agcggttctt taaaacccac ctgttcgact gggtcaccag tgacccgttc    480
ggacggtgcc acctgctgga acttccaact gaccacaaag gtgtctacgg cagcctgacc    540
gactcgtatg cttatatgag gaacggctgg gatgttgaag tcactgcagt gggaaaccag    600
ttcaatggag gatgcctgtt ggtggccatg gtgccagaac tttgctccat acagaagagg    660
gagctgtacc agctcacgct ctttcctcac cagttcatca accctcggac gaacatgaca    720
gcacacatca ctgtgcccct tgttggcgtc aaccgttatg accagtacaa ggtacacaaa    780
ccttggaccc tcgtggttat ggttgtagcc cccctgaccg tcaacagtga aggtgccccg    840
caaatcaagg tgtatgccaa catcgcacct accaacgtac acgtcgcggg tgagttccct    900
tccaaagagg ggatcttccc tgtggcttgc agcgatggtt atggcggtct ggtgaccact    960
gacccgaaaa cggctgaccc cgcttacggg aaagtgttta accccccccg caacatgttg   1020
ccggggcggt tcaccaattt tcttgacgtg gctgaggcgt gccccacgtt tctccacttc   1080
gagggtgacg tgccatacgt gaccacgaag acggattcag acagggtgct cgctcagttc   1140
gacttgtctt tggcagcaaa gcacatgtcg aacaccttcc ttgcaggtct cgcccagtac   1200
tacacacagt acagcggcac catcaacctg cacttcatgt tcacagggcc tactgacgcg   1260
aaggcgcgtt acatgattgc gtatgctcct cctggcatgg aaccacctaa acgccagag   1320 gcggctgccc actgcattca tgctgaatgg gacacagggt tgaactcaaa attcacattt   1380
tcaatccctt accttttcgg ggctgattac gcttacacag cgtctgacac tgctgagacc   1440
acaaatgtac agggatgggt ttgcctgttt caaataacac acgggaaagc tgacggcgac   1500
gcactggtcg ttttggctag cgccggaaag gactttgagc tgcgcctgcc ggtggatgct   1560
cgcacacaga ctacctccgc gggcgagtca gctgaccccg tgaccgccac cgttgagaat   1620
tacggtggcg agacacaggt ccagaggcgc caacacacgg acgtctcatt tatattagac   1680
agatttgtga agtgacacc aaaagaccaa attaatgtat tggacctgat gcaaccccct   1740
gctcacactt tggtgggagc actccttcgt actgccactt actatttcgc tgacttagag   1800
gtggcagtga agcacgaggg aaacctcacc tgggtcccga acggggcgcc tgaagcggcg   1860
ttggacaaca ccaccaaccc aacagcttac cacaaggcac cactcacccg acttgcactg   1920
ccttacacgg cgccacaccg cgtgttggct actgtttaca acgggaacag caagtatggt   1980
gacggcacgg tggccaatgt gagaggtgac ctgcaagtgt ggcccagaa ggcggcgaga   2040 gcgctgccta cctccttcaa ctacggtgcc attaaagcta ctcgggtgac tgaactgctt   2100
taccgcatga agagggctga acatactgt ccccggcctc ttttggccat tcacccggac   2160
caggctagac acaagcagaa gattgtggca ccggtgaaac agcttctaaa ttttgacctg   2220
ctcaaattgg cgggagatgt ggagtccaac cctgggccc                          2259
```

```
<210> SEQ ID NO 12
<211> LENGTH: 2211
<212> TYPE: DNA
<213> ORGANISM: Foot-and-mouth disease virus
<220> FEATURE:
<221> NAME/KEY: misc_feature
```

<223> OTHER INFORMATION: Wild-type P1 polyprotein precursor derived from
FMDV Type A (A/IRN/1/96)

<400> SEQUENCE: 12

```
ggagccggac aatccagtcc ggcaaccggg tcgcaaaacc aatcaggtaa cactggaagc      60
atcatcaaca actactacat gcaacaatac cagaattcca tggacacaca acttggagac    120
aacgccatca gcggaggctc caacgaggga tccacagaca ccacctccac ccacacaacc    180
aacacccaaa acaacgactg ttttcaaaa ttggccagct ctgcctttag cgggctcttc     240
ggtgctcttc ttgctgacaa gaagacagag gaaaccaccc tcctggaaga ccgcatcctc    300
actacccgca acggacatac cacctcaaca acccagtcga gtgtgggagt cacctacggg    360
tattccactg agaagaccca cgtttccggg cccaatacgt ctggcttgga acscgggtg     420
acacaggcag agagatttttt caagaaacac ttgtttaatt ggacaactga caaacctttt    480
gggtacttgg aaaagctgga acttcccact gaccacaagg gtgtttacgg cacctagtg     540
gattcttttg catacatgag aaacggctgg gacgtggagg tgtccgccgt tggcaaccag    600
ttcaacggtg gatgcctcct agtggccatg gtgcctgaat ggaaagagtt cactccacgt    660
gagaagtacc agctcacctt gttcccgcat cagttcatta gccccagaac caacatgact    720
gctcacatca cggtcccgta ccttggtgtg aatagatatg accagtacaa gaagcacaag    780
ccctggacgc tggtcgtgat ggtggttttcg ccgcttacca acagcagcat ggtgccaca    840
gaaatcaagg tctacgccaa catcgcccca acccacgttc acgtagccgg tgagctcccg    900
tcgaaagagg ggatcgtgcc ggttgcttgc tcggatgggt acggcggtct ggtgacaacg    960
gacccgaaaa cagctgaccc tgtctacggt aaggtgtaca ccccgcctag gacaaactat   1020
cctgggcgct tcacaaactt gttggacgtg gccgaggctt gcccaaccct cctctgttc    1080
gacgacggga accgtacgt tgtgacaaga gaggatgagc agcgtctact ggccaagttc    1140
gacgtctctc ttgctgcaaa gcacatgtca aacacctacc tatcagggat agcgcagtac   1200
tatgcacagt actctggcac catcaacctc cacttcatgt tcactggttc tactgactca   1260
aaagcccgct acatggtagc gtacgtcccg cccggcgtgg aaacaccgcc ggacacgcct   1320
gagagagctg cacactgcat ccacgctgag tgggacacag ggctgaactc caaattcact   1380
ttttctatcc cgtacgtgtc cgccgcggat tacgcgtaca ccgcgtctga tgtggccgaa   1440
acaacaaacg tacagggatg ggtctgcatc taccagatca cgcacgggaa ggctcaaaac   1500
gacactctgg ttgtgtcgat tagcgccggc aaggactttg agttgcgtct cccgattgac   1560
ccccgcacac agaccacatc tgccggggag tctgcagacc cagtcaccac cactgttgaa   1620
aactacggcg gtgagacaca gtccagcgga cgtcaccaca ctgatgtcgg cttcataatg   1680
gacagatttg tgaagattaa caaccaccagc cccacacacg tcattgacct catgcaaacc   1740
caccagcacg ggttggtggg cgctctcctg cgtgctgcca cgtactactt ctcagacctg   1800
gagattgtgg tgcgccacga aggcaacctg acgtgggtgc caatggagc accagaggca   1860
gccctgagca acgcgggcaa ccccaccgcc tacaacaaag caccattcac gaggctagca   1920
ctcccctaca ctgcgccgca ccgcgtgttg gcgacggtgt acaacgggac gagcaagtac   1980
tcgacaactg gtgggcacac acggggtgac ttggagctc ttgcggcgag ggtcgccgcc   2040
caactccctg cctctttcaa ctttggcgca atccggggcca ctgacatcag tgagcttctt   2100
gtgcgcatga gcgtgctga gctctactgc cccaggccac tactggcagt ggaagtgaca   2160
gcgcaagaca ggcacaaaca gaagatcatt gcgcctgcga aacagctcct g             2211
```

<210> SEQ ID NO 13
<211> LENGTH: 2193
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
    FMDV Type C (Haute Loire FR/69)
<220> FEATURE:
<221> NAME/KEY: misc_feature
<222> LOCATION: (1182)..(1183)
<223> OTHER INFORMATION: n is a, c, g, or t
<220> FEATURE:
<221> NAME/KEY: misc_feature
<222> LOCATION: (1455)..(1456)
<223> OTHER INFORMATION: n is a, c, g, or t
<220> FEATURE:
<221> NAME/KEY: misc_feature
<222> LOCATION: (1708)..(1709)
<223> OTHER INFORMATION: n is a, c, g, or t
<220> FEATURE:
<221> NAME/KEY: misc_feature
<222> LOCATION: (1883)..(1885)
<223> OTHER INFORMATION: n is a, c, g, or t

<400> SEQUENCE: 13

| | | | | | |
|---|---|---|---|---|---|
| ggagctgggc | aatccagccc | agcgaccggt | tcgcagaacc | aatccggtaa | cactggcagc | 60 |
| ataattaaca | actactatat | gcagcagtac | caaaactcca | tggacacaca | actcggcgac | 120 |
| aacgccatca | gtggaggctc | taatgaaggc | tccacggaca | caacctctac | acacacaact | 180 |
| aacacccaga | caacgactg | gttttccaaa | cttgccagtt | cagccttcag | cggtcttttc | 240 |
| ggcgcccttc | tcgctgataa | gaaaacggag | gaaaccactc | tccttgaagg | ccgcattctc | 300 |
| actacccgta | acgggcacac | gacctcgaca | acccagtcga | gcgtcggagt | cacattcggg | 360 |
| tatgcaactg | ctgaagatag | cacgtctggg | cccaatacat | ctggtctaga | gacgcgcgtt | 420 |
| catcaggcag | agaggttttt | caaaatggca | cttttttgatt | gggttccctc | acaaaatttt | 480 |
| ggacacatgc | acaaggttgt | tctgccccat | gaaccaaaag | gtgtttacgg | gggtcttgtc | 540 |
| aagtcatacg | cgtacatgcg | caatggctgg | gacgtcgagg | tgactgctgt | tggaaaccag | 600 |
| ttcaacggcg | gctgcctcct | ggtggcgctc | gtccccgaga | tgggcgacat | cagtgacagg | 660 |
| gaaaagtacc | aactaaccct | ttaccccac | cagttcatca | acccacgcac | caacatgacg | 720 |
| gcacacatca | ctgtgcccta | cgtgggtgtc | aacaggtatg | accagtacaa | acagcacagg | 780 |
| ccctggaccc | tcgtggtcat | ggttgtcgca | ccactcacca | caaacacagc | aggtgcccaa | 840 |
| cagatcaagg | tgtatgccaa | catagcccca | accaacgtgc | acgtagcagg | tgagctcccc | 900 |
| tccaaggagg | ggatcttccc | cgttgcgtgt | tctgacggtt | acggcaacat | ggtgacaact | 960 |
| gacccgaaaa | cggctgaccc | tgcctacggg | aaagtttaca | ccccccccg | gactgctctg | 1020 |
| ccggggcggt | tcacaaacta | cctggatgtt | gccgaggctt | gtcccaccct | cctgatgttc | 1080 |
| gagaacgtac | cttacgtctc | aacacgaact | gacgggcaaa | ggctactggc | caagttcgac | 1140 |
| gtgtcgctgg | cagcgaaaca | catgtcaaac | acctacttgg | cnngcttggc | ccagtactac | 1200 |
| acacagtatg | ctgggacaat | caacctacac | ttcatgttca | ctgggccgac | cgacgcgaaa | 1260 |
| gctcggtaca | tggtggcgta | cgtgcccct | ggcatgacg | caccagacaa | cccagaagag | 1320 |
| gctgcccact | gcatacacgc | agaatgggac | actggtctga | actctaagtt | cacatttttcc | 1380 |
| atcccgtaca | tctcggccgc | tgactacgcg | taccgcgt | cccacgaggc | tgaaacaaca | 1440 |
| tgtgtacagg | ggtgnntctg | tgtgtaccaa | atcactcacg | gcaaggcaga | cgcagacgcg | 1500 |
| ctcgtcgtct | ccgcatcagc | ggggaaagac | tttgagctcc | ggctacctgt | ggacgctaga | 1560 |

-continued

```
cgacaaacta cggccactgg tgaatctgct gaccccgtca ccactaccgt tgagaactac     1620
ggaggagaga ctcaagtcca acgtcgccac acaccgacg ttgccttcgt ccttgaccgg      1680
tttgtgaagg tcacagtgtc gggtaacnna cacacactcg acgtgatgca ggcacacaaa    1740
gacaacatcg tgggcgcgct tcttcgcgca gccacgtact acttttctga ttcggaaata    1800
gcagtgaccc acactgggaa gctcacatgg gtgcccaacg gtgcaccagt ttctgcactt    1860
gacaacacaa ccaatcccac tgnnnaccac aagggcccgt tgactcgact ggctctccca    1920
tacaccgcgc cacaccgtgt gttggctacg gcgtacactg gcactacgac ctacaccgcc    1980
agtacacgcg gggatttggt tcacctagcg gcgacgcatg ctcggcactt gccgacatcg    2040
ttcaactttg gtgcagttaa agcagaaaca atcactgagt tgctcgtgcg catgaagcgt    2100
gctgaactct attgtcctag gccgattctt ccgattcagc caacgggtga tagacacaag    2160
caaccgctcg tcgcacctgc aaaacaactg ctg                                 2193
```

<210> SEQ ID NO 14
<211> LENGTH: 2220
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV SAT3 ZAM/04/96/3

<400> SEQUENCE: 14

```
ggagcaggcc agtcctcacc cgccacgggg tcacaaaacc aatctggcaa cactggtagc      60
attattaata actattacat gcaacagtac caaaattcca tggacaccca gcttggcgac     120
aacgccatat caggtggttc aaatgaaggt agcacggaca ccacgtccac gcataccaac     180
aacacccaga acaacgattg gttttcaaaa ttggcacaat cagccatttc agggctcttc     240
ggggctctgt tggctgacaa aaagacagaa gagacaactc ttcttgagga ccgcatcctc     300
accacgcgcc acaataccac cacctcaacc acccagagct cagtgggagt gacctacgga     360
tacgcgtcag cggaccgttt cctcccgggc cccaacacca gtgggcttga gactagggtc     420
gaacaggcgg agaggttctt caaggagaaa cttttcacct ggacggctgc tcaggagtac     480
gcacacgtgc acctgcttga gctcccagtt gaccacaaag gcatctacgg tgccatggtt     540
gacacacacg catacgtgcg caacggttgg gatgtgcagg tctccgcgac cagcacccaa     600
ttcaacggtg gtactctact ggtggccatg gtgccagagc tccactcact tgacaagcgc     660
gacgtgtcac aactcacgct gttcccacac cagttcatca cccacgtac caacacgacg     720 gcacacattg tcgtccccta cgtggggggtt aacagacatg accaggtgaa actccacaaa    780
gcctggacac tggtagtggc tgtcatggca ccactcacaa catcaagcat gggccaggac     840
aacgttgagg tgtacgccaa catcgcacct accaacgtgt tgttgctgg agagatgcca     900 aacaaacaag gtatcatccc cgtagcctgc aacgatggc atggcggctt ccagaacact     960 gaccccgaaga ccgcagaccc catctacggt ctagtgtcca acgcgcctcg cacggccttc    1020
cccggaaggt tcacaaacct tttggacgtg gccgaggcat gtcccacttt cctggatttt    1080
gacggcacac cgtacgttaa gacccggcac aacagtggat ctaaaattct cacgcacatt    1140
gatttggcat ttggacacaa agctttcaag aacacgtacc ttgctgggct agcacaatac    1200
tatgcccagt acagtggttc cctgaacctg catttcatgt acactgggcc cacgcagtca    1260
aaggcccgct tcatggttgt gtacgttcca cctgggacca cccggtccc cgacacacct    1320
```

| | | | | |
|---|---|---|---|---|
| gaggcggcgt | cgcactgcta | ccactcagaa | tgggacacag | gtctgaactc | caagttcacg | 1380 |
| ttcacagtgc | cgtacatttc | ggcggccgac | tttgcctaca | cctactgtga | tgaacctgaa | 1440 |
| caagcgtctg | cacaaggctg | ggttacgctc | taccaggtga | cagacacgca | cgaccccgac | 1500 |
| tcggcggtgc | tgatttcggt | cagtgccggg | tccgacttgg | aattcaggtt | gccaatcaac | 1560 |
| cccgcaccac | agacaaccag | tgcaggtgaa | ggtgcaaatg | tggtcacaac | cgatgtcacc | 1620 |
| acacatggtg | gtgaaacagt | gcaccccagg | agacagcaca | ccaacgtcga | gtttctgctt | 1680 |
| gacaggttca | cacacattgg | ggcaatgacc | acttctaaga | caattagcct | ccttgacaca | 1740 |
| aaggaacaca | cgctggtggg | cgcgatcctg | cgctcagcaa | cgtactactt | ttgtgacctg | 1800 |
| gaagtggcag | tattgggtga | cgcggaatgg | gtagcttggg | tgcccaatgg | gtgcccacac | 1860 |
| accgaccggg | tggaagacaa | tccagtcgtt | cactcgaaaa | acggtgtgac | ccgattcgcg | 1920 |
| ctgcctttta | ctgcgccaca | cggtgtcctc | tcaaccgtgt | acaatggaac | atgcaagtac | 1980 |
| tcaaagaccc | aacgcgtgac | tccccgacgc | ggcgaccttg | ccgtgttgtc | cacacgtgtt | 2040 |
| gagacggaac | aggaacgatg | tttgcccaca | gcattcaact | tcggtcgatt | gttgtgtgac | 2100 |
| tcgggcgacg | tgtactacag | gatgaagagg | gcggagcttt | actgcccgcg | ccctctcaga | 2160 |
| gtcaggtaca | cccacaccac | tgacaggtac | aaggtcgccc | tggttaaacc | agagaaacaa | 2220 |

<210> SEQ ID NO 15
<211> LENGTH: 2220
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from FMDV SAT2 SEN/05/75

<400> SEQUENCE: 15

| | | | | |
|---|---|---|---|---|
| ggcgcaggac | aatcctcacc | tgctacgggc | tcacaaaacc | agtccggcaa | cactggcagc | 60 |
| atcatcaata | actactacat | gcaacagtac | caaaactcaa | tggacactca | gttgggcgac | 120 |
| aacgccatca | gcggtgggtc | caacgagggg | tcgactgaca | ccacgtcgac | ccacaccaac | 180 |
| aacacccaga | caacgattg | gttttccaaa | ttggctcaat | ccgccatctc | gggtcttttc | 240 |
| ggggcccctcc | tggcagacaa | gaaaacagag | gagaccactc | tgctagagga | ccgcatactc | 300 |
| accacacgac | acggcactac | tacctcaacc | acacagagtt | cagtaggtgt | cacgtttggg | 360 |
| tacgcggacg | cggatagttt | cacagccggt | cctaacactt | ctggccttga | gactcacgtt | 420 |
| ccacaagcag | agaggttttt | caaagaaaaa | ttgtttgatt | ggacaagtga | caaaccattt | 480 |
| ggcacaacgt | gcgtgcttga | actgcccaaa | gatcacaaag | gcatctacgg | gaagctcaac | 540 |
| gactcatacg | cgtacatgag | gaacggctgg | gacgttcagg | tcagtgctac | cagcacacag | 600 |
| ttcaacggag | gttccctcct | tgtggctatg | gtgcctgaac | tcagttccat | ccgtgacagg | 660 |
| gaagagttcc | aaccaacact | ctacccgcac | cagttcataa | acccacgcac | caacaccacg | 720 |
| gcacacatcc | aggtcccgta | cctgggtgta | aaccgccatg | accagggcaa | acgccaccag | 780 |
| gcgtggtctc | tggttgtgat | ggtgctcacg | cctctcacca | ctgaggcaca | gatgaactct | 840 |
| gggaccgttg | aggtgtacgc | caacattgca | cccaccaacg | tgtacgtggc | gggcgaactc | 900 |
| cctgggaaac | agggaattgt | gcccgtcgcg | tgctcagacg | gttacggtgg | attccagaac | 960 |
| acagacccca | agacggccga | tccgatttac | ggacatgtgt | acaccccctc | gcggcaagac | 1020 |
| tgtcacggtc | ggttctccaa | cctgttggac | gtcgctgagg | catgccccac | actactgaac | 1080 |
| ttcgacggga | aaccgtacgt | tgtgacgaag | agcagtgggg | acaaggtaat | ggccgctttt | 1140 |

```
gacgtggcct tcacccacaa ggtgcacaag aacacgtttt tggcggggct ggccgactat    1200
tacacccagt acactggcag tctcaactac cacttcatgt acacaggccc cactcaccac    1260
aaagccaaat tcatggtggc atacgtccca ccagggattg cagttgcgca gctgcccaaa    1320
acaccggaag acgcttcaca ctgctaccac tctgaatggg acacgggtct gaactcatct    1380
ttcacgttcg cagttcctta catctcgtct gcggacttct cctacacaca cacagacaca    1440
cccgccatgg ccacaaccaa cggctgggtt gttgtgttgc aagtcacaga cacgcactcg    1500
gcagaagccg cagtcgttgt gtccgtcagt gctgggcctg acctcgagtt caggttccca    1560
atcgaccccg ttcgccagac acatcggcg ggcgagagcg cggacgtagt gacgaccgac    1620
ccaaccacac acggtggggc agtcacaaac ccgcgacgca aacacactga cgttgctttt    1680
ctcctggaca ggtcaaccca cgttcacact gggaagacca cattcgaggt caacttgatg    1740
gacaccaagg agaaagcctt ggtgggcgcc gttctgcgcg cggccaccta ctattttgt    1800 gacttggaaa ttgcatgtgt tggtgaccac aaaagggtgt tctggcaacc caacggtgcg    1860
cccagggcga cccagttggg agacaaccca atggtcttct cccacaacaa ggtggcacgg    1920
ttcgcaatcc cgttcaccgc gccacaccgt ctgctctcca ctgtttacaa cggtgagtgt    1980
aactactcca cgtcggtgac gccgatacgt ggtgacaggg cggtcctggc ggccaagtac    2040
gccagcacca agcacacgct cccgtccact ttcaatttcg ggtacgtgac cgccgacgcg    2100
ccagtcgacg tttactaccg aatgaaaagg agcgaactct actgcccag ccactcttg    2160 ccagcgtacg accaccaatc gcacgacagg tttgatgcgc ccattggcgt agagaagcaa    2220
```

<210> SEQ ID NO 16
<211> LENGTH: 2229
<212> TYPE: DNA
<213> ORGANISM: Artificial Sequence
<220> FEATURE:
<223> OTHER INFORMATION: Wild-type P1 polyprotein precursor derived from
    FMDV SAT1 NIG/15/75
<220> FEATURE:
<221> NAME/KEY: misc_feature
<223> OTHER INFORMATION: Wild-type P1 polyprotein precursor derived from
    FMDV SAT1 NIG/15/75

<400> SEQUENCE: 16

```
ggggccggac aatccagtcc ggcaactgga tcacagaacc agtcaggcaa cacaggtagt      60
atcatcaaca actactatat gcaacagtac caaaactcga tggacacgca gctcggcgac     120
aacgccatca gcgtggctc caatgagggg tcgacagaca ccacgtcgac ccacacaaac     180
aacacccaga caacgactg gttttcaaag ctggcccggt ccgcttcag cggtttggtc     240 ggcgctctgc tcgcagacaa gaaaccgag gaaacgactc tccttgagga ccggatcctc     300
accacgtcac acggaactac tacgtctacg acacagagtt ccgtgggagt gacgtatggg     360
tacgcttcgt ccgacaagtt ctaccaggg cccaacacca cgggctgga gactagagtc     420 gaacaggcgg agcgttactt caagcagaag ttgtttgact gggacacaac gcagaagttt     480
ggcacaaccc acatcctggc cctaccaacg gaccataagg gtgtctacgg tcaactgtta     540
gactcataca cttacatgag gaacggttgg gacgtccaag tctcggccac cgccacccag     600
ttcaacggtg gctgtctact agtggctatg gtgcctgagc tttgctcact gagtgaccgg     660
gagaagtacc aactcactct ttccccacac cagttcataa accccagaac caacaccact     720
gcgcacattc aggtgcctta cctgggtgtg atcgccacg accaggggaa acgccacaag     780
gcatggaccc tggttgtcat ggtggtgtca ccgtacacga atgaccagac aatcgggtca     840
```

```
tcaaaggctg aggtgtacgt aaacatcgca ccgaccaacg tgtacgtcgc cggagagaaa      900
ccggccaaac aaggtattgt gccagtcgct gtgtccgacg gatacggcgg cttccaaaac      960
acagacccaa agacatctga cccaatttat ggtcacgttt acaatgctgc acgtaccggt     1020
taccccggga agttcagcaa cctcatggat gttgcggagg cgtgtccaac gtttctcgac     1080
ttcaatggag caccatacgt aaccacacaa gcacattctg ggtcaaaggt catggcatgt     1140
ttcgatttgg ccttcgggca caagaacctt aaaaacacat acctctcagg cttggcacag     1200
tactacacac agtacagcgg tactttgaac ctccacttca tgtactctgg acccaccaac     1260
aacaaggcca agtacatggt tgcgtacata ccaccaggta cgcacccgct gcctgaaaca     1320
cctgaccagg cgtcccactg ttaccacgca gagtgggaca caggtctcaa ctccactttc     1380
acattcacag tgccatacat ttctggtgcg actttgcct acacccacgc ctacgaacct      1440
gaacaatcca gcgttcaagg ttgggtgggc gtctaccaga tcactgacac ccacgagaaa     1500
gatggtgcac tgatcgtcac ggttagcgcg gggcccgacc tcgagttccg cctaccgata     1560
agccccagcc ggcagacaac aagtgctgga aaggtgccg acgtcgtcac gaccgacgca      1620
tccgcgcacg gaggtaacac tcgccctaca cggcgggttc acaccgacgt cgcgtttctc     1680
ttggaccgtt ttactctggt tggcaagact gtggacaaca agatggtgtt agacttgctc     1740
aagacaaaag agaaggcact ggtgggcgca gtcttgcgtt ccgccacgta ctacttttca     1800
gacttggagg tagcatgtgt tggcactaac aaatgggtcg gttgggttcc taacggtgcc     1860
cctgtgccta aggaagtggg cgacaaccca gtcgtcttct cccacaacgg caccacccgt     1920
ttcgctctgc cgtacactgc tccacaccgt gtgttggcaa caacctacaa cggtgattgc     1980
aagtacaagg cccagcccgt ggagaacaga gagatccgcg gtgacatggc cgtcttggcc     2040
gctcgcgtcg ctgaggagac tcacatcccg accactttca actacgggat gatcttgacc     2100
gaaagcgaag ttgacgtcta cgtgagaatg aagagggctg agctctactg cccacgcttt     2160
ctgctcacca cgtacgacca caacggagct gacaggtaca agaccacgct ggtagcacca     2220
gagaaacaa                                                              2229
```

<210> SEQ ID NO 17
<211> LENGTH: 2196
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV Asia 1 IND 63/72

<400> SEQUENCE: 17

```
ggagccgggc aatccagccc ggcaaccggg tcgcagaacc agtcaggcaa cactggaagc       60
atcattaaca actactacat gcagcaatac cagaattcca tggacacaca acttggtgac      120
aacgctatta gcggaggctc caacgaaggt tccacggaca ccacttccac acacacaaac      180
aacacccaaa acaacgattg gttctcgcgc ctagccagtt cggccttcac cggactgttt      240
ggcgctcttt tggccgacaa gaaaacggaa gagacaaccc tgcttgaaga ccgcatcctc      300
accaccagga acgccacac gacgtcgacg acacagtcaa gcgtcggcgt gacttacggt       360
tacgctgtgg ccgaagacgc tgtttctggg cccaacacct caggcttgga cccgcgtg       420 acacaggctg aacggttttt caagaaacac ctgtttgatt ggacaccaaa tctatcgttt      480
ggacactgtc actacctgga actcccctcc gaacacaaag gcgtgttcgg cagcctcatg      540
```

| | |
|---|---|
| gactcctacg cctacatgag gaacgggtgg gacattgagg tgaccgctgt tggaaaccag | 600 |
| ttcaatggtg gttgcctcct cgtcgcactc gtcccggagc tgaaagaact tgacacgcgg | 660 |
| cagaagtacc agttgaccct cttcccacac cagttcatca acccacgcac caacatgacg | 720 |
| gctcacatca acgtgccgtt cgtgggtgtc aacaggtacg accaatacaa gctccacaag | 780 |
| ccgtggacgc ttgttgtgat ggtggtggct ccacttaccg tcaaaaccgg tggttccgaa | 840 |
| cagatcaagg tttacatgaa tgcagcacca acccacgtgc atgtggcagg gaactgccc | 900 |
| tcgaaagagg ggatagtacc cgttgcgtgt gcggccggtt atggcaacat ggtgaccaca | 960 |
| gacccgaaga cggctgaccc cgtttacggg aaagtgttca accccccag aacaaatctc | 1020 |
| cctgggcgct tcacaaactt ccttgatgta gcggaggcat gcccaacctt cctccgcttc | 1080 |
| ggagaagtac catttgtgaa gacggggaac tctggtgacc gcttgcttgc caagtttgac | 1140 |
| gtgtcgctcg ctgcggggca catgtccaac acctacttgg caggcttggc gcagtactac | 1200 |
| acacagtaca gcggcaccat gaacatccac ttcatgttca ccgggcccac ggatgccaaa | 1260 |
| gctcgctaca tggtggctta cgtacctcct ggtatggagc cacccacaga acccgagcgg | 1320 |
| gccgcgcact gtatacattc tgagtgggac actggtctta attccaagtt caccttttcc | 1380 |
| attccttacc tctctgctgc tgactacgct tacactgctt ctgacgtggc cgagaccacg | 1440 |
| agtgtgcagg gatgggtgtg catttatcag attacgcacg gcaaagctga aggcgacgcg | 1500 |
| ctggtcgtgt ctgtcagtgc cggcaaggac tttgagtttc gactgccagt ggatgctcgc | 1560 |
| cgagagacta ccaccgctgg cgagtccgca gacccagtca ccaccacagt tgagaactac | 1620 |
| ggaggagaga ctcagtcggc ccgacggcta cacactgacg ttgcttttgt tctcgacagg | 1680 |
| tttgtgaaac tcaccccaa gaacacccag attcttgatc tcatgcagat ccctcacac | 1740 |
| acactggttg gagcgttact ccggtccgcg acgtactact tctcggacct ggaggttgcg | 1800 |
| cttgttcaca caggctcagt cacatggggtg cccaatggcg cgcccaagga cgccttggac | 1860 |
| aaccacacca cccgactgc ctaccagaag aaacccatca cccgcctggc gctcccctac | 1920 |
| accgctcccc accgtgtgct ggcaacagtg tacaacggga agacaacgta cgggacacaa | 1980 |
| cccacgcggc gtggtgacct tgctgttctt gcacagcggg taagcaacag gctgcccacc | 2040 |
| tccttcaact acggtgctgt gaaggctgac accatcacgg agctgttgat ccgcatgacg | 2100 |
| cgtgcggaga catactgccc caggccttttg ctagctcttg acaccaccca cgaccgccgt | 2160 |
| aagcaggaga tcattgcacc tgagaagcaa gttttg | 2196 |

<210> SEQ ID NO 18
<211> LENGTH: 2925
<212> TYPE: DNA
<213> ORGANISM: Artificial Sequence
<220> FEATURE:
<223> OTHER INFORMATION: O1P1-3C(wt) insert

<400> SEQUENCE: 18

| | |
|---|---|
| gccgccgcca tgggagccgg gcaatccagc ccggcaaccg ggtcacagaa ccaatcaggc | 60 |
| aacactggga gcatcatcaa caattactac atgcagcagt accaaaactc tatggacaca | 120 |
| caacttggtg acaacgctac aagcggaggc tcaaacgagg ggtccacgga cacaacctcc | 180 |
| acccacacaa ccaacactca gaacaacgac tggttctcga agctggccag ttccgctttc | 240 |
| agcggtcttt tcggcgctct tctcgccgac aagaaaaccg aggagaccac tcttcttgag | 300 |
| gaccgcatcc tcactactcg taacggacac accacctcga caacccagtc gagcgtagga | 360 |
| gtcacatacg ggtatgcaac ggctgaggat ttcgtgagcg ggccaaacac ctctggtctt | 420 |

```
gagaccaggg ttgcccaggc agagcggttc tttaaaaccc acctgttcga ctgggtcaca    480
agtgacccgt tcggacggtg ccacctgcta gaacttccaa ctgaccacaa aggtgtctat    540
ggcagcctga ccgactcgta tgcttatatg aggaacggct gggatgttga agtcactgct    600
gtgggaaatc agttcaatgg aggatgcctg ttggtggcta tggtgccaga actttgctcc    660
atacagaaga gggagctgta ccagctcacg ctctttcctc accagttcat caaccctcgg    720
acgaacatga cagcacacat cactgtgccc tttgttggcg tcaaccgtta tgaccagtac    780
aaggtacaca aaccttggac cctcgtggtt atggttgtag ccccctgac cgtcaacagt      840 gaaggtgccc cgcaaatcaa ggtgtatgcc aacatcgcac ctaccaacgt acacgtcgcg    900
ggtgagttcc cttccaaaga ggggatcttc cctgtggctt gcagcgatgg ttatggcggt    960
ctggtgacaa ctgaccccgaa aacgctgac cccgcttacg ggaaagtgtt taacccccc    1020 cgcaacatgt tgccggggcg gttcaccaat tttcttgacg tggctgaggc gtgccccacg    1080
tttctccact tcgagggtga cgtgccatac gtgaccacga agacggattc agacagggtg    1140
ctcgctcagt tcgacttgtc tttggcagca agcacatgt ccaacaccctt ccttgcaggt    1200 ctcgcccagt actacacaca gtacagcggc caatcaacc tgcacttcat gttcacaggg    1260
cctactgacg cgaaggcgcg ttacatgatt gcgtatgctc ctcctggcat ggaaccacct    1320
aaaacgccag aggcggctgc ccactgcatc catgctgaat gggacacagg ttgaactca    1380 aaattcacat tttcaatccc ttaccttttcg gcggctgatt acgcttacac agcgtctgac    1440
actgctgaga ccacaaatgt acagggatgg gtttgcctgt ttcaaataac acacgggaaa    1500
gctgacggcg acgcactggt cgttttggcc agcgccggaa aggactttga gctgcgcctg    1560
ccggtggatg ctcgcacaca gactacctca gcgggcgagt cagcagaccc cgtgaccgcc    1620
accgttgaga attacggtgg cgagacacag gtccagaggc gccaacacac ggacgtgtca    1680
tttatattag acagatttgt gaaagtgaca ccaaaagacc aaattaatgt attggacctg    1740
atgcaaaccc ctgctcacac tttggtggga gcactccttc gtactgccac ttactatttc    1800
gctgacttag aggtggcagt gaagcacgag ggaaacctca cctgggtgcc gaacggggcg    1860
cctgaagcgg cgttggacaa caccaccaac ccaacagctt accacaaggc accactcacc    1920
cgacttgcac tgccttacac ggcgccacac cgcgtgttgg ctactgttta caacgggaac    1980
agcaagtatg tgacggcac ggtggccaat gtgagaggtg atctgcaagt gttggcccag    2040
aaggcggcga gcgctgcc tacctccttc aactacggtg ccattaaagc tactcgggtg    2100
actgaactgc tttaccgcat gaagagggct gagacatact gtccccggcc tcttttggcc    2160
attcacccgg accaggctag acacaagcag aagattgtgg ctccggtgaa acagcttcta    2220
aattttgacc tgctcaaatt ggcgggagat gtggagtcca accctgggcc cagcggccgc    2280
atgagtggtg ccccaccgac cgacttgcaa aagatggtca tgagcaacac taagcctgtt    2340
gagctcatcc ttgacggtaa gacggtggcc atctgctgcg ccaccggagt gtttggtact    2400
gcctacctcg tgcctcgtca ccttttcgca gaaaagtacg acaggatcat gttggacggc    2460
agggccatga cagacagtga ctacagagtg tttgagtttg agattaaagt aaaaggacag    2520
gacatgctct cagacgctgc gctcatggtg ctccaccgtg caaccgtgt gagagacatc    2580 acgaaacact ttcgtgatac agcaagaatg aagaaaggta ccccgttgt cggcgtgatc    2640 aacaacgccg acgttgggag actgatttttc tccggtgagg ccctcaccta caaggacatt    2700
gtagtgtgca tggatggaga caccatgccg ggcctatttg cctacagagc cgctaccaag    2760
```

-continued

| | |
|---|---|
| gctggctact gtggaggagc cgttcttgcc aaggacggag ctgacacatt tatcgtcggc | 2820 |
| actcactccg caggaggcaa tggagtcggg tactgctcat gcgtatctag gtccatgctc | 2880 |
| ttgaagatga aggcacacat tgaccccgaa ccacaccacg agtag | 2925 |

<210> SEQ ID NO 19
<211> LENGTH: 3047
<212> TYPE: DNA
<213> ORGANISM: Artificial Sequence
<220> FEATURE:
<223> OTHER INFORMATION: O1P1-HIV-3C(C142T) insert

<400> SEQUENCE: 19

| | |
|---|---|
| gccgccgcca tgggagccgg gcaatccagc ccggcaaccg ggtcacagaa ccaatcaggc | 60 |
| aacactggga gcatcatcaa caattactac atgcagcagt accaaaactc tatggacaca | 120 |
| caacttggtg acaacgctac aagcggaggc tcaaacgagg ggtccacgga cacaacctcc | 180 |
| acccacacaa ccaacactca gaacaacgac tggttctcga agctggccag ttccgctttc | 240 |
| agcggtcttt tcggcgctct tctcgccgac aagaaaaccg aggagaccac tcttcttgag | 300 |
| gaccgcatcc tcactactcg taacggacac accacctcga caacccagtc gagcgtagga | 360 |
| gtcacatacg gtatgcaac ggctgaggat ttcgtgagcg ggccaaacac ctctggtctt | 420 |
| gagaccaggg ttgcccaggc agagcggttc tttaaaaccc acctgttcga ctgggtcaca | 480 |
| agtgacccgt tcggacggtg ccacctgcta gaacttccaa ctgaccacaa aggtgtctat | 540 |
| ggcagcctga ccgactcgta tgcttatatg aggaacggct gggatgttga agtcactgct | 600 |
| gtgggaaatc agttcaatgg aggatgcctg ttggtggcta tggtgccaga actttgctcc | 660 |
| atacagaaga gggagctgta ccagctcacg ctctttcctc accagttcat caaccctcgg | 720 |
| acgaacatga cagcacacat cactgtgccc tttgttggcg tcaaccgtta tgaccagtac | 780 |
| aaggtacaca aaccttggac cctcgtggtt atggttgtag ccccctgac cgtcaacagt | 840 |
| gaaggtgccc cgcaaatcaa ggtgtatgcc aacatcgcac ctaccaacgt acacgtcgcg | 900 |
| ggtgagttcc cttccaaaga ggggatcttc cctgtggctt gcagcgatgg ttatggcggt | 960 |
| ctggtgacaa ctgaccccga aaacggctga cccgcttacg ggaaagtgtt taaccccccc | 1020 |
| cgcaacatgt tgccggggcg gttcaccaat tttcttgacg tggctgaggc gtgccccacg | 1080 |
| tttctccact cgagggtga cgtgccatac gtgaccacga agacggattc agacagggtg | 1140 |
| ctcgctcagt tcgacttgtc tttggcagca agcacatgt ccaacacctt ccttgcaggt | 1200 |
| ctcgcccagt actacacaca gtacagcggc accatcaacc tgcacttcat gttcacaggg | 1260 |
| cctactgacg cgaaggcgcg ttacatgatt gcgtatgctc ctcctggcat ggaaccacct | 1320 |
| aaaacgccag aggcggctgc ccactgcatc catgctgaat gggacacagg gttgaactca | 1380 |
| aaattcacat tttcaatccc ttaccttttcg gcggctgatt acgcttacac agcgtctgac | 1440 |
| actgctgaga ccacaaatgt acagggatgg gtttgcctgt tcaaataac acacgggaaa | 1500 |
| gctgacggcg acgcactggt cgttttggcc agcgccggaa aggactttga gctgcgcctg | 1560 |
| ccggtggatg ctcgcacaca gactacctca gcgggcgagt cagcagaccc cgtgaccgcc | 1620 |
| accgttgaga attacggtgg cgagacacag gtccagaggc gccaacacac ggacgtgtca | 1680 |
| tttatattag acagatttgt gaaagtgaca ccaaaagacc aaattaatgt attggacctg | 1740 |
| atgcaaaccc ctgctcacac tttggtggga gcactccttc gtactgccac ttactatttc | 1800 |
| gctgacttag aggtggcagt gaagcacgag ggaaacctca cctgggtgcc gaacgggggcg | 1860 |
| cctgaagcgg cgttggacaa caccaccaac ccaacagctt accacaaggc accactcacc | 1920 |

```
cgacttgcac tgccttacac ggcgccacac cgcgtgttgg ctactgttta caacgggaac    1980
agcaagtatg gtgacggcac ggtggccaat gtgagaggtg atctgcaagt gttggcccag    2040
aaggcggcga gagcgctgcc tacctccttc aactacggtg ccattaaagc tactcgggtg    2100
actgaactgc tttaccgcat gaagagggct gagacatact gtccccggcc tcttttggcc    2160
attcacccgg accaggctag acacaagcag aagattgtgg ctccggtgaa acagcttcta    2220
aattttgacc tgctcaaatt ggcgggagat gtggagtcca ccctgggcc cagcggccgc    2280 ggacctttt tagggaagat ctggccttcc tacaagggaa ggccagggaa ttttcttacg     2340
agggaccggt aaaaaaaccc gtagcactca aggttaaagc aaagaatctc attgttaccg    2400
aaagtggagc cccaccgacc gacttgcaaa agatggtcat gggcaacacc aagcctgttg    2460
aactcatcct cgacgggaag acggtggcca tttgttgtgc taccggtgtg tttggcactg    2520
cgtacctcgt gcctcgtcat cttttttgcag aaaaatatga caagatcatg ctggacggca   2580
gagccatgac agacagtgac tacagagtgt ttgagtttga gattaaagta aaaggacagg    2640
acatgctctc agacgctgcg ctcatggtac tccaccgtgg aatcgcgtg agagacatca     2700 cgaaacactt tcgtgacaca gcaagaatga gaaaaggcac ccctgttgtc ggagtaatca    2760
acaatgccga cgtcgggaga ctgatcttct ctggtgaggc ccttacctac aaggacattg    2820
tagtgacaat ggatgagac accatgcctg gcctgttttgc ctacaaagcc gccaccaagg   2880
ctggctactg tggggagcc gttcttgcta aggacggagc tgacacattc atcgttggca     2940
ctcactccgc aggcggcaat ggagttggat actgctcatg cgtttccagg tccatgttgc    3000
tgaaaatgaa ggcgcacatc gaccccgaac cacaccacga gaagtaa                  3047

<210> SEQ ID NO 20
<211> LENGTH: 558
<212> TYPE: DNA
<213> ORGANISM: Artificial Sequence
<220> FEATURE:
<223> OTHER INFORMATION: SGLuc insert

<400> SEQUENCE: 20
atgggagtca agttctgtt tgccctgatc tgcatcgctg tggccgaggc caagcccacc       60
gagaacaacg aagacttcaa catcgtggcc gtggccagca acttcgcgac cacggatctc    120
gatgctgacc gcgggaagtt gcccggcaag aagctgccgc tggaggtgct caaagagatg    180
gaagccaatg cccggaaagc tggctgcacc aggggctgtc tgatctgcct gtcccacatc    240
aagtgcacgc ccaagatgaa gaagtggctc caggacgct gccacaccta cgaaggcgac     300
aaagagtccg cacagggcgg cataggcgag gcgatcgtcg acattcctga gattcctggg    360
ttcaaggact tggagcccat ggagcagttc atcgcacagg tcgatctgtg tgtggactgc    420
acaactggct gcctcaaagg gcttgccaac gtgcagtgtt ctgacctgct caagaagtgg    480
ctgccgcaac gctgtgcgac cttttgccagc aagatccagg ccaggtggaa caagatcaag    540
ggggccggtg gtgactaa                                                   558

<210> SEQ ID NO 21
<211> LENGTH: 22
<212> TYPE: DNA
<213> ORGANISM: Artificial Sequence
<220> FEATURE:
<223> OTHER INFORMATION: Synthetic primer - O1MSeq1-F

<400> SEQUENCE: 21
```
gagcatcatc aacaattact ac                                            22

<210> SEQ ID NO 22
<211> LENGTH: 22
<212> TYPE: DNA
<213> ORGANISM: Artificial Sequence
<220> FEATURE:
<223> OTHER INFORMATION: Synthetic primer - O1MSeq2-F

<400> SEQUENCE: 22
ggaccgcatc ctcactactc gt                                            22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer - O1MSeq3-F

<400> SEQUENCE: 23
gccacctgct agaacttcca ac                                            22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer - O1MSeq4-F

<400> SEQUENCE: 24
aggtacacaa accttggacc ct                                            22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer - O1MSeq5-F

<400> SEQUENCE: 25
aacggctgac cccgcttacg gg                                            22

<210> SEQ ID NO 26
<211> LENGTH: 22
<212> TYPE: DNA
<213> ORGANISM: Artificial Sequence
<220> FEATURE:
<223> OTHER INFORMATION: Synthetic primer - O1MSeq6-F

<400> SEQUENCE: 26
gcttacacag cgtctgacac tg                                            22

<210> SEQ ID NO 27
<211> LENGTH: 22
<212> TYPE: DNA
<213> ORGANISM: Artificial Sequence
<220> FEATURE:
<223> OTHER INFORMATION: Synthetic primer - O1MSeq7-F

<400> SEQUENCE: 27
aaacctcacc tgggtgccga ac                                            22

<210> SEQ ID NO 28
<211> LENGTH: 22
<212> TYPE: DNA
<213> ORGANISM: Artificial Sequence

```
<220> FEATURE:
<223> OTHER INFORMATION: Synthetic primer - O1MSeq8-F

<400> SEQUENCE: 28
agatgtggag tccaaccctg gg                                            22

<210> SEQ ID NO 29
<211> LENGTH: 21
<212> TYPE: DNA
<213> ORGANISM: Artificial Sequence
<220> FEATURE:
<223> OTHER INFORMATION: Synthetic primer - O1P1-Seq-R1

<400> SEQUENCE: 29
gtccgtggac ccctcgtttg a                                             21

<210> SEQ ID NO 30
<211> LENGTH: 22
<212> TYPE: DNA
<213> ORGANISM: Artificial Sequence
<220> FEATURE:
<223> OTHER INFORMATION: Synthetic primer - O1P1-Seq-R2

<400> SEQUENCE: 30
tcgaggtggt gtgtccgtta cg                                            22

<210> SEQ ID NO 31
<211> LENGTH: 8825
<212> TYPE: DNA
<213> ORGANISM: Artificial Sequence
<220> FEATURE:
<223> OTHER INFORMATION: pMC-CMV-SV40-polyA O1P1-HIV-3C(C142T) (with
      bacterial backbone)

<400> SEQUENCE: 31
acattaccct gttatcccta gatacattac cctgttatcc cagatgacat accctgttat    60
ccctagatga cattaccctg ttatcccaga tgacattacc ctgttatccc tagatacatt   120
accctgttat cccagatgac atacccgttt atccctagat gacattaccc tgttatccca   180
gatgacatta ccctgttatc cctagataca ttaccctgtt atcccagatg acatacctg    240 ttatccctag atgacattac cctgttatcc cagatgacat accctgtta tccctagata   300 cattaccctg ttatcccaga tgacatacc tgttatccct agatgacatt accctgttat   360
cccagatgac attaccctgt tatccctaga tacattaccc tgttatccca gatgacatac   420
cctgttatcc ctagatgaca ttaccctgtt atcccagatg acattaccct gttatcccta   480
gatacattac cctgttatcc cagatgacat accctgttat cccagatga cattaccctg   540 ttatcccaga tgacattacc ctgttatccc tagatacatt accctgttat cccagatgac   600 atacccgtt atccctagat gacattaccc tgttatccca gatgacatta ccctgttatc   660
cctagataca ttaccctgtt atcccagatg acatacctg ttatccctag atgacattac   720
cctgttatcc cagataaact caatgatgat gatgatgatg tcgagactc agcggccgcg   780 gtgccagggc gtgccttgg ctccccggg cgcgactagt gaattgatac tagtattatg   840
cccagtacat gaccttatgg gactttccta cttggcagta catctacgta ttagtcatcg   900
ctattaccat ggtgatgcgg ttttggcagt acatcaatgg gcgtggatag cggtttgact   960
cacggggatt tccaagtctc caccccattg acgtcaatgg gagtttgttt tggcaccaaa  1020
atcaacggga ctttccaaaa tgtcgtaaca actccgcccc attgacgcaa atgggcggta  1080
ggcgtgtacg gtgggaggtt tatataagca gagctcgttt agtgaaccgt cagatcgcct  1140
```

```
ggagacgcca tccacgctgt tttgacctcc atagaagatt ctagagtcga cgcggccgcg    1200
gatccgccgc cgccatggga gccgggcaat ccagcccggc aaccgggtca cagaaccaat    1260
caggcaacac tgggagcatc atcaacaatt actacatgca gcagtaccaa aactctatgg    1320
acacacaact tggtgacaac gctacaagcg gaggctcaaa cgaggggtcc acggacacaa    1380
cctccaccca cacaaccaac actcagaaca cgactggtt ctcgaagctg ccagttccg      1440 cttttcagcgg tcttttcggc gctcttctcg ccgacaagaa aaccgaggag accactcttc   1500
ttgaggaccg catcctcact actcgtaacg acacaccac ctcgacaacc cagtcgagcg     1560
taggagtcac atacgggtat gcaacggctg aggatttcgt gagcgggcca aacacctctg    1620
gtcttgagac cagggttgcc caggcagagc ggttctttaa acccacctg ttcgactggg     1680 tcacaagtga cccgttcgga cggtgccacc tgctagaact tccaactgac cacaaaggtg    1740
tctatggcag cctgaccgac tcgtatgctt atatgaggaa cggctgggat gttgaagtca    1800
ctgctgtggg aaatcagttc aatggaggat gcctgttggt ggctatggtg ccagaacttt    1860
gctccataca gaagagggag ctgtaccagc tcacgctctt tcctcaccag ttcatcaacc    1920
ctcggacgaa catgacagca cacatcactg tgccctttgt tggcgtcaac cgttatgacc    1980
agtacaaggt acacaaacct tggaccctcg tggttatggt tgtagccccc ctgaccgtca    2040
acagtgaagg tgccccgcaa atcaaggtgt atgccaacat cgcacctacc aacgtacacg    2100
tcgcgggtga gttcccttcc aaagagggga tcttccctgt ggcttgcagc gatggttatg    2160
gcggtctggt gacaactgac ccgaaaaacgg ctgaccccgc ttacgggaaa gtgtttaacc   2220
ccccccgcaa catgttgccg gggcggttca ccaattttct tgacgtggct gaggcgtgcc    2280
ccacgtttct ccacttcgag ggtgacgtgc catacgtgac cacgaagacg gattcagaca    2340
gggtgctcgc tcagttcgac ttgtctttgg cagcaaagca catgtccaac accttccttg    2400
caggtctcgc ccagtactac acacagtaca gcggcaccat caacctgcac ttcatgttca    2460
cagggcctac tgacgcgaag gcgcgttaca tgattgcgta tgctcctcct ggcatggaac    2520
cacctaaaac gccagaggcg gctgcccact gcatccatgc tgaatgggac acagggttga    2580
actcaaaatt cacatttca atcccttacc tttcggcggc tgattacgct tacacagcgt     2640
ctgacactgc tgagaccaca aatgtacagg gatgggtttg cctgttcaa ataacacacg     2700 ggaaagctga cggcgacgca ctggtcgttt tggccagcgc cggaaaggac tttgagctgc    2760
gcctgccggt ggatgctcgc acacagacta cctcagcggg cgagtcagca gaccccgtga    2820
ccgccaccgt tgagaattac ggtggcgaga cacaggtcca gaggcgccaa cacacggacg    2880
tgtcatttat attagacaga tttgtgaaag tgacaccaaa agaccaaatt aatgtattgg    2940
acctgatgca aaccccctgct cacactttgg tgggagcact ccttcgtact gccacttact   3000
atttcgctga cttagaggtg gcagtgaagc acgagggaaa cctcacctgg gtgccgaacg    3060
gggcgcctga agcggcgttg gacaacacca ccaacccaac agcttaccac aaggcaccac    3120
tcacccgact tgcactgcct tacacggcgc cacaccgcgt gttggctact gtttacaacg    3180
ggaacagcaa gtatggtgac ggcacggtgg ccaatgtgag aggtgatctg caagtgttgg    3240
cccagaaggc ggcgagagcg ctgcctacct ccttcaacta cggtgccatt aaagctactc    3300
gggtgactga actgctttac cgcatgaaga gggctgagac atactgtccc cggcctcttt    3360
tggccattca cccggaccag gctagacaca agcagaagat tgtggctccg gtgaaacagc    3420
ttctaaattt tgacctgctc aaattggcgg gagatgtgga gtccaaccct gggcccagcg    3480
```

```
gccgcggacc ttttttaggg aagatctggc cttcctacaa gggaaggcca gggaattttc      3540
ttacgaggga ccggtaaaaa aacccgtagc actcaaggtt aaagcaaaga atctcattgt      3600
taccgaaagt ggagccccac cgaccgactt gcaaaagatg gtcatgggca acaccaagcc      3660
tgttgaactc atcctcgacg ggaagacggt ggccatttgt tgtgctaccg gtgtgtttgg      3720
cactgcgtac ctcgtgcctc gtcatctttt tgcagaaaaa tatgacaaga tcatgctgga      3780
cggcagagcc atgacagaca gtgactacag agtgtttgag tttgagatta agtaaaagg      3840 acaggacatg ctctcagacg ctgcgctcat ggtactccac cgtgggaatc gcgtgagaga      3900
catcacgaaa cactttcgtg acacagcaag aatgaagaaa ggcacccctg ttgtcggagt      3960
aatcaacaat gccgacgtcg ggagactgat cttctctggt gaggccctta cctacaagga      4020
cattgtagtg acaatggatg gagacaccat gcctggcctg tttgcctaca agccgccac       4080 caaggctggc tactgtgggg gagccgttct tgctaaggac ggagctgaca cattcatcgt      4140
tggcactcac tccgcaggcg gcaatggagt tggatactgc tcatgcgttt ccaggtccat      4200
gttgctgaaa atgaaggcgc acatcgaccc cgaaccacac cacgagaagt aagaattcgc      4260
tagctcgaca atcaacctct ggattacaaa atttgtgaaa gattgactgg tattcttaac      4320
tatgttgctc cttttacgct atgtggatac gctgctttaa tgcctttgta tcatgctatt      4380
gcttcccgta tggctttcat tttctcctcc ttgtataaat cctggttgct gtctctttat      4440
gaggagttgt ggcccgttgt caggcaacgt ggcgtggtgt gcactgtgtt tgctgacgca      4500
acccccactg gttggggcat tgccaccacc tgtcagctcc tttccgggac tttcgctttc      4560
ccctccccta ttgccacggc ggaactcatc gccgcctgcc ttgcccgctg ctggacaggg      4620
gctcggctgt tgggcactga caattccgtg gtgttgtcgg ggaaatcatc gtccttcct      4680 tggctgctcg cctgtgttgc cacctggatt ctgcgcggga cgtccttctg ctacgtccct      4740
tcggccctca atccagcgga ccttccttcc cgcggcctgc tgccggctct gcggcctctt      4800
ccgcgtcttc gccttcgccc tcagacgagt cggatctccc tttgggccgc ctccccgcct      4860
ggtaccttta agaccaatga cttacaaggc agctgtagat cttagccact ttttaaaaga      4920 aaaggggga ctgaaggggc taattcactc ccaacgaaga taagatctgc ttttgcttg       4980 tactgggtct ctctggttag accagatctg agcctgggag ctctctggct aactagggaa      5040
cccactgctt aagcctcaat aaagcttgcc ttgagtgctt caagtagtgt gtgcccgtct      5100
gttgtgtgac tctggtaact agagatccct cagacccttt tagtcagtgt ggaaaatctc      5160
tagcagtagt agttcatgtc atcttattat tcagtattta aacttgcaa agaaatgaat       5220 atcagagagt gagaggaact tgtttattgc agcttataat ggttacaaat aaagcaatag      5280
catcacaaat ttcacaaata aagcattttt ttcactgcat tctagttgtg gtttgtccaa      5340
actcatcaat gtatcttatc atgtctggct ctagctatcc cgcccctaac tccgcccatc      5400
ccgcccctaa ctccgcccag ttccgcccat tctccgcccc atggctgact aattttttt       5460 atttatgcag aggccgaggc cgcctcggcc tctgagctat tccagaagta gtgaggaggc      5520
ttttttggag gcctagactt ttgcagatcg acccatgggg gcccgcccca actggggtaa      5580
cctttgagtt ctctcagttg ggggtaatca gcatcatgat gtggtaccac atcatgatgc      5640
tgattataag aatgcggccg ccacactcta gtggatctcg agttaataat tcagaagaac      5700
tcgtcaagaa ggcgatagaa ggcgatgcgc tgcgaatcgg gagcggcgat accgtaaagc      5760
acgaggaagc ggtcagccca ttcgccgcca agctcttcag caatatcacg ggtagccaac      5820
gctatgtcct gatagcggtc cgccacaccc agccggccac agtcgatgaa tccagaaaag      5880
```

```
cggccatttt ccaccatgat attcggcaag caggcatcgc catgggtcac gacgagatcc    5940
tcgccgtcgg gcatgctcgc cttgagcctg gcgaacagtt cggctggcgc gagcccctga    6000
tgctcttcgt ccagatcatc ctgatcgaca agaccggctt ccatccgagt acgtgctcgc    6060
tcgatgcgat gtttcgcttg gtggtcgaat gggcaggtag ccggatcaag cgtatgcagc    6120
cgccgcattg catcagccat gatggatact ttctcggcag gagcaaggtg agatgacagg    6180
agatcctgcc ccggcacttc gcccaatagc agccagtccc ttcccgcttc agtgacaacg    6240
tcgagcacag ctgcgcaagg aacgcccgtc gtggccagcc acgatagccg cgctgcctcg    6300
tcttgcagtt cattcagggc accggacagg tcggtcttga caaaaagaac cgggcgcccc    6360
tgcgctgaca gccggaacac ggcggcatca gagcagccga ttgtctgttg tgcccagtca    6420
tagccgaata gcctctccac ccaagcggcc ggagaacctg cgtgcaatcc atcttgttca    6480
atcatgcgaa acgatcctca tcctgtctct tgatcagagc ttgatcccct cgccatcag    6540 atccttggcg gcgagaaagc catccagttt actttgcagg gcttcccaac cttaccagag    6600
ggcgccccag ctggcaattc cggttcgctt gctgtccata aaaccgccca gtctagctat    6660
cgccatgtaa gcccactgca agctacctgc tttctctttg cgcttgcgtt ttcccttgtc    6720
cagatagccc agtagctgac attcatccgg ggtcagcacc gtttctgcgg actggctttc    6780
tacgtgctcg agggggggcca aacggtctcc agcttggctg ttttggcgga tgagagaaga    6840
ttttcagcct gatacagatt aaatcagaac gcagaagcgg tctgataaaa cagaatttgc    6900
ctggcggcag tagcgcggtg gtcccacctg accccatgcc gaactcagaa gtgaaacgcc    6960
gtagcgccga tggtagtgtg gggtctcccc atgcgagagt agggaactgc caggcatcaa    7020
ataaaacgaa aggctcagtc gaaagactgg gcctttcgtt ttatctgttg tttgtcggtg    7080
aacgctctcc tgagtaggac aaatccgccg ggagcggatt tgaacgttgc gaagcaacgg    7140
cccggagggt ggcgggcagg acgcccgcca taaactgcca ggcatcaaat taagcagaag    7200
gccatcctga cggatggcct ttttgcgttt ctacaaactc ttttgtttat ttttctaaat    7260
acattcaaat atgtatccgc tcatgaccaa aatcccttaa cgtgagtttt cgttccactg    7320
agcgtcagac cccgtagaaa agatcaaagg atcttcttga tccttttttt ttctgcgcgt    7380
aatctgctgc ttgcaaacaa aaaaaccacc gctaccagcg gtggtttgtt tgccggatca    7440
agagctacca actctttttc cgaaggtaac tggcttcagc agagcgcaga taccaaatac    7500
tgtccttcta gtgtagccgt agttaggcca ccacttcaag aactctgtag caccgcctac    7560
atacctcgct ctgctaatcc tgttaccagt ggctgctgcc agtggcgata agtcgtgtct    7620
taccgggttg gactcaagac gatagttacc ggataaggcg cagcggtcgg gctgaacggg    7680
gggttcgtgc acacagccca gcttggagcg aacgacctac accgaactga gatacctaca    7740
gcgtgagcta tgagaaagcg ccacgcttcc cgaagggaga aaggcggaca ggtatccggt    7800
aagcggcagg gtcggaacag gagagcgcac gagggagctt ccagggggaa acgcctggta    7860
tctttatagt cctgtcgggt ttcgccacct ctgacttgag cgtcgatttt tgtgatgctc    7920
gtcagggggg cggagcctat ggaaaaacgc cagcaacgcg gcctttttac ggttcctggc    7980
cttttgctgg ccttttgctc acatgttctt tcctgcgtta tccctgatt ctgtggataa    8040 ccgtattacc gcctttgagt gagctgatac cgctcgccgc agccgaacga ccgagcgcag    8100
cgagtcagtg agcgaggaag cggaagagcg cctgatgcgg tattttctcc ttacgcatct    8160
gtgcggtatt tcacaccgca tatggtgcac tctcagtaca atctgctctg atgccgcata    8220
```

| | |
|---|---|
| gttaagccag tatacactcc gctatcgcta cgtgactggg tcatggctgc gccccgacac | 8280 |
| ccgccaacac ccgctgacgc gccctgacgg gcttgtctgc tcccggcatc cgcttacaga | 8340 |
| caagctgtga ccgtctccgg gagctgcatg tgtcagaggt tttcaccgtc atcaccgaaa | 8400 |
| cgcgcgaggc agcagatcaa ttcgcgcgcg aaggcgaagc ggcatgcata atgtgcctgt | 8460 |
| caaatggacg aagcagggat tctgcaaacc ctatgctact ccgtcaagcc gtcaattgtc | 8520 |
| tgattcgtta ccaattatga caacttgacg gctacatcat tcactttttc ttcacaaccg | 8580 |
| gcacggaact cgctcgggct ggccccggtg catttttaa atacccgcga gaaatagagt | 8640 |
| tgatcgtcaa aaccaacatt gcgaccgacg gtggcgatag gcatccgggt ggtgctcaaa | 8700 |
| agcagcttcg cctggctgat acgttggtcc tcgcgccagc ttaagacgct aatccctaac | 8760 |
| tgctggcgga aagatgtga cagacgcgac ggcgacaagc aaacatgctg tgcgacgctg | 8820 |
| gcgat | 8825 |

<210> SEQ ID NO 32
<211> LENGTH: 28
<212> TYPE: DNA
<213> ORGANISM: Artificial Sequence
<220> FEATURE:
<223> OTHER INFORMATION: Synthetic primer - NotI-3cLeb89-F

<400> SEQUENCE: 32

| | |
|---|---|
| cagcggccgc atgagtggtg ccccaccg | 28 |

<210> SEQ ID NO 33
<211> LENGTH: 23
<212> TYPE: DNA
<213> ORGANISM: Artificial Sequence
<220> FEATURE:
<223> OTHER INFORMATION: Synthetic primer - 3CLeb89-EcoRI-R

<400> SEQUENCE: 33

| | |
|---|---|
| gaattcctac tcgtggtgtg gtt | 23 |

<210> SEQ ID NO 34
<211> LENGTH: 8703
<212> TYPE: DNA
<213> ORGANISM: Artificial Sequence
<220> FEATURE:
<223> OTHER INFORMATION: pMC-CMV-SV40-polyA O1P1-3C(wt) (with bacterial backbone)

<400> SEQUENCE: 34

| | |
|---|---|
| acattaccct gttatcccta gatacattac cctgttatcc cagatgacat accctgttat | 60 |
| ccctagatga cattaccctg ttatcccaga tgacattacc ctgttatccc tagatacatt | 120 |
| accctgttat cccagatgac ataccctgtt atccctagat gacattaccc tgttatccca | 180 |
| gatgacatta ccctgttatc cctagataca ttaccctgtt atcccagatg acataccctg | 240 |
| ttatccctag atgacattac cctgttatcc cagatgacat taccctgtta tcccagatga | 300 |
| cattaccctg ttatcccaga tgacataccc tgttatccct agatgacatt accctgttat | 360 |
| cccagatgac attaccctgt tatccctaga tacattaccc tgttatccca gatgacatac | 420 |
| cctgttatcc ctagatgaca ttaccctgtt atcccagatg acattaccct gttatcccta | 480 |
| gatacattac cctgttatcc cagatgacat accctgttat ccctagatga cattaccctg | 540 |
| ttatcccaga tgacattacc ctgttatccc tagatacatt accctgttat cccagatgac | 600 |
| ataccctgtt atccctagat gacattaccc tgttatccca gatgacatta ccctgttatc | 660 |

```
cctagataca ttaccctgtt atcccagatg acatacccctg ttatccctag atgacattac    720
cctgttatcc cagataaact caatgatgat gatgatgatg gtcgagactc agcggccgcg    780
gtgccagggc gtgcccttgg gctccccggg cgcgactagt gaattgatac tagtattatg    840
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt ccaagtctc caccccattg acgtcaatgg gagtttgttt tggcaccaaa   1020
atcaacggga ctttccaaaa tgtcgtaaca actccgcccc attgacgcaa atgggcggta   1080
ggcgtgtacg gtgggaggtt tatataagca gagctcgttt agtgaaccgt cagatcgcct   1140
ggagacgcca tccacgctgt tttgacctcc atagaagatt ctagagtcga cgcggccgcg   1200
gatccgccgc cgccatggga gccgggcaat ccagcccggc aacccgggtca cagaaccaat   1260
caggcaacac tgggagcatc atcaacaatt actacatgca gcagtaccaa aactctatgg   1320
acacacaact tggtgacaac gctacaagcg gaggctcaaa cgaggggtcc acggacacaa   1380
cctccacccca cacaaccaac actcagaaca acgactggtt ctcgaagctg ccagttccg   1440
ctttcagcgg tcttttcggc gctcttctcg ccgacaagaa aaccgaggag accactcttc   1500
ttgaggaccg catcctcact actcgtaacg gacacaccac ctcgacaacc cagtcgagcg   1560
taggagtcac atacgggtat gcaacggctg aggatttcgt gagcgggcca aacacctctg   1620
gtcttgagac caggggttgcc caggcagagc ggttctttaa aacccacctg ttcgactggg   1680
tcacaagtga cccgttcgga cggtgccacc tgctagaact tccaactgac cacaaaggtg   1740
tctatggcag cctgaccgac tcgtatgctt atatgaggaa cggctgggat gttgaagtca   1800
ctgctgtggg aaatcagttc aatggaggat gcctgttggt ggctatggtg ccagaactttt   1860
gctccataca gaagagggag ctgtaccagc tcacgctctt tcctcaccag ttcatcaacc   1920
ctcggacgaa catgacagca cacatcactg tgccctttgt tggcgtcaac cgttatgacc   1980
agtacaaggt acacaaacct tggaccctcg tggttatggt tgtagccccc ctgaccgtca   2040
acagtgaagg tgccccgcaa atcaaggtgt atgccaacat cgcacctacc aacgtacacg   2100
tcgcgggtga gttcccttcc aaagagggga tcttccctgt ggcttgcagc gatggttatg   2160
gcggtctggt gacaactgac ccgaaaacgg ctgaccccgc ttacgggaaa gtgtttaacc   2220
ccccccgcaa catgttgccg gggcggttca ccaattttct tgacgtggct gaggcgtgcc   2280
ccacgtttct ccacttcgag ggtgacgtgc catacgtgac cacgaagacg gattcagaca   2340
gggtgctcgc tcagttcgac ttgtctttgg cagcaaagca catgtccaac accttccttg   2400
caggtctcgc ccagtactac acacagtaca gcggcaccat caacctgcac ttcatgttca   2460
cagggcctac tgacgcgaag gcgcgttaca tgattgcgta tgctcctcct ggcatggaac   2520
cacctaaaac gccagaggcg gctgcccact gcatccatgc tgaatgggac acagggttga   2580
actcaaaatt cacattttca atcccttacc tttcggcggc tgattacgct tacacagcgt   2640
ctgacactgc tgagaccaca aatgtacagg gatgggtttg cctgtttcaa ataacacacg   2700
ggaaagctga cggcgacgca ctggtcgttt tggccagcgc cggaaaggac tttgagctgc   2760
gcctgccggt ggatgctcgc acacagacta cctcagcggg cgagtcagca gaccccgtga   2820
ccgccaccgt tgagaattac ggtggcgaga cacaggtcca gaggcgccaa cacacggacg   2880
tgtcatttat attagacaga tttgtgaaag tgacaccaaa agaccaaatt aatgtattgg   2940
acctgatgca aaccccctgct cacactttgg tgggagcact ccttcgtact gccacttact   3000
atttcgctga cttagaggtg gcagtgaagc acgagggaaa cctcacctgg gtgccgaacg   3060
```

```
gggcgcctga agcggcgttg gacaacacca ccaacccaac agcttaccac aaggcaccac    3120
tcacccgact tgcactgcct tacacggcgc cacaccgcgt gttggctact gtttacaacg    3180
ggaacagcaa gtatggtgac ggcacggtgg ccaatgtgag aggtgatctg caagtgttgg    3240
cccagaaggc ggcgagagcg ctgcctacct ccttcaacta cggtgccatt aaagctactc    3300
gggtgactga actgctttac cgcatgaaga gggctgagac atactgtccc cggcctcttt    3360
tggccattca cccggaccag gctagacaca agcagaagat tgtggctccg gtgaaacagc    3420
ttctaaattt tgacctgctc aaattggcgg agatgtgga gtccaaccct gggcccagcg    3480
gccgcatgag tggtgcccca ccgaccgact tgcaaaagat ggtcatgagc aacactaagc    3540
ctgttgagct catccttgac ggtaagacgg tggccatctg ctgcgccacc ggagtgtttg    3600
gtactgccta cctcgtgcct cgtcaccttt tcgcagaaaa gtacgacagg atcatgttgg    3660
acggcagggc catgacagac agtgactaca gagtgtttga gtttgagatt aaagtaaaag    3720
gacaggacat gctctcagac gctgcgctca tggtgctcca ccgtggcaac cgtgtgagag    3780
acatcacgaa acactttcgt gatacagcaa gaatgaagaa aggtaccccc gttgtcggcg    3840
tgatcaacaa cgccgacgtt gggagactga ttttctccgg tgaggccctc acctacaagg    3900
acattgtagt gtgcatggat ggagacacca tgccgggcct atttgcctac agagccgcta    3960
ccaaggctgg ctactgtgga ggagccgttc ttgccaagga cggagctgac acatttatcg    4020
tcggcactca ctccgcagga ggcaatggag tcgggtactg ctcatgcgta tctaggtcca    4080
tgctcttgaa gatgaaggca cacattgacc ccgaaccaca ccacgagtag gaattcgcta    4140
gctcgacaat caacctctgg attacaaaat tgtgaaaga ttgactggta ttcttaacta    4200
tgttgctcct tttacgctat gtggatacgc tgctttaatg cctttgtatc atgctattgc    4260
ttcccgtatg gctttcattt tctcctcctt gtataaatcc tggttgctgt ctctttatga    4320
ggagttgtgg cccgttgtca ggcaacgtgg cgtggtgtgc actgtgtttg ctgacgcaac    4380
ccccactggt tggggcattg ccaccacctg tcagctcctt tccggacttt cgctttccc     4440 cctcccctatt gccacggcgg aactcatcgc cgcctgcctt gcccgctgct ggacaggggc    4500
tcggctgttg ggcactgaca attccgtggt gttgtcgggg aaatcatcgt cctttccttg    4560
gctgctcgcc tgtgttgcca cctggattct gcgcgggacg tccttctgct acgtcccttc    4620
ggccctcaat ccagcggacc ttccttcccg cggcctgctg ccggtctgc ggcctcttcc     4680 gcgtcttcgc cttcgccctc agacgagtcg gatctccctt gggccgcct ccccgcctgg     4740 tacctttaag accaatgact acaaggcag ctgtagatct tagccacttt ttaaaagaaa    4800 agggggggact ggaagggcta attcactccc aacgaagata agatctgctt tttgcttgta    4860
ctgggtctct ctggttagac cagatctgag cctgggagct ctctggctaa ctagggaacc    4920
cactgcttaa gcctcaataa agcttgcctt gagtgcttca agtagtgtgt gcccgtctgt    4980
tgtgtgactc tggtaactag agatccctca gacccttta gtcagtgtgg aaaatctcta    5040
gcagtagtag ttcatgtcat cttattattc agtatttata acttgcaaag aaatgaatat    5100
cagagagtga gaggaacttg tttattgcag cttataatgg ttacaaataa agcaatagca    5160
tcacaaattt cacaaataaa gcatttttt cactgcattc tagttgtggt ttgtccaaac    5220
tcatcaatgt atcttatcat gtctggctct agctatcccg cccctaactc cgcccatccc    5280
gcccctaact ccgcccagtt ccgcccattc tccgccccat ggctgactaa ttttttttat    5340
ttatgcagag gccgaggccg cctcggcctc tgagctattc cagaagtagt gaggaggctt    5400
```

```
ttttggaggc ctagactttt gcagatcgac ccatgggggc ccgccccaac tggggtaacc    5460
tttgagttct ctcagttggg ggtaatcagc atcatgatgt ggtaccacat catgatgctg    5520
attataagaa tgcggccgcc acactctagt ggatctcgag ttaataattc agaagaactc    5580
gtcaagaagg cgatagaagg cgatgcgctg cgaatcggga gcggcgatac cgtaaagcac    5640
gaggaagcgg tcagcccatt cgccgccaag ctcttcagca atatcacggg tagccaacgc    5700
tatgtcctga tagcggtccg ccacacccag ccggccacag tcgatgaatc cagaaaagcg    5760
gccattttcc accatgatat tcggcaagca ggcatcgcca tgggtcacga cgagatcctc    5820
gccgtcgggc atgctcgcct tgagcctggc gaacagttcg gctggcgcga gcccctgatg    5880
ctcttcgtcc agatcatcct gatcgacaag accggcttcc atccgagtac gtgctcgctc    5940
gatgcgatgt ttcgcttggt ggtcgaatgg gcaggtagcc ggatcaagcg tatgcagccg    6000
ccgcattgca tcagccatga tggatacttt ctcggcagga gcaaggtgag atgacaggag    6060
atcctgcccc ggcacttcgc ccaatagcag ccagtccctt cccgcttcag tgacaacgtc    6120
gagcacagct gcgcaaggaa cgcccgtcgt ggccagccac gatagccgcg ctgcctcgtc    6180
ttgcagttca ttcagggcac cggacaggtc ggtcttgaca aaaagaaccg ggcgcccctg    6240
cgctgacagc cggaacacgg cggcatcaga gcagccgatt gtctgttgtg cccagtcata    6300
gccgaatagc ctctccaccc aagcggccgg agaacctgcg tgcaatccat cttgttcaat    6360
catgcgaaac gatcctcatc ctgtctcttg atcagagctt gatccctgc gccatcagat     6420
ccttggcggc gagaaagcca tccagtttac tttgcagggc ttcccaacct taccagaggg    6480
cgccccagct ggcaattccg gttcgcttgc tgtccataaa accgcccagt ctagctatcg    6540
ccatgtaagc ccactgcaag ctacctgctt tctctttgcg cttgcgtttt cccttgtcca    6600
gatagcccag tagctgacat tcatccgggg tcagcaccgt ttctgcggac tggctttcta    6660
cgtgctcgag gggggccaaa cggtctccag cttggctgtt ttggcggatg agagaagatt    6720
ttcagcctga tacagattaa atcagaacgc agaagcggtc tgataaaaca gaatttgcct    6780
ggcggcagta gcgcggtggt cccacctgac cccatgccga actcagaagt gaaacgccgt    6840
agcgccgatg gtagtgtggg gtctcccat gcgagagtag ggaactgcca ggcatcaaat    6900
aaaacgaaag gctcagtcga aagactgggc ctttcgtttt atctgttgtt tgtcggtgaa    6960
cgctctcctg agtaggacaa atccgccggg agcggatttg aacgttgcga agcaacggcc    7020
cggagggtgg cgggcaggac gcccgccata aactgccagg catcaaatta agcagaaggc    7080
catcctgacg gatggccttt ttgcgtttct acaaactctt tgtttatttt ttctaaatac    7140
attcaaatat gtatccgctc atgaccaaaa tcccttaacg tgagttttcg ttccactgag    7200
cgtcagaccc cgtagaaaag atcaaaggat cttcttgaga tccttttttt ctgcgcgtaa    7260
tctgctgctt gcaaacaaaa aaaccaccgc taccagcggt ggtttgtttg ccggatcaag    7320
agctaccaac tctttttccg aaggtaactg gcttcagcag agcgcagata ccaaatactg    7380
tccttctagt gtagccgtag ttaggccacc acttcaagaa ctctgtagca ccgcctacat    7440
acctcgctct gctaatcctg ttaccagtgg ctgctgccag tggcgataag tcgtgtctta    7500
ccgggttgga ctcaagacga tagttaccgg ataaggcgca gcggtcgggc tgaacggggg    7560
gttcgtgcac acagcccagc ttggagcgaa cgacctacac cgaactgaga tacctacagc    7620
gtgagctatg agaaagcgcc acgcttcccg aagggagaaa ggcggacagg tatccggtaa    7680
gcggcagggt cggaacagga gagcgcacga gggagcttcc agggggaaac gcctggtatc    7740
tttatagtcc tgtcgggttt cgccacctct gacttgagcg tcgatttttg tgatgctcgt    7800
```

| | |
|---|---|
| caggggggcg gagcctatgg aaaaacgcca gcaacgcggc cttttttacgg ttcctggcct | 7860 |
| tttgctggcc ttttgctcac atgttctttc ctgcgttatc ccctgattct gtggataacc | 7920 |
| gtattaccgc ctttgagtga gctgataccg ctcgccgcag ccgaacgacc gagcgcagcg | 7980 |
| agtcagtgag cgaggaagcg gaagagcgcc tgatgcggta ttttctcctt acgcatctgt | 8040 |
| gcggtatttc acaccgcata tggtgcactc tcagtacaat ctgctctgat gccgcatagt | 8100 |
| taagccagta tacactccgc tatcgctacg tgactgggtc atggctgcgc ccgacaccc | 8160 |
| gccaacaccc gctgacgcgc cctgacgggc ttgtctgctc ccggcatccg cttacagaca | 8220 |
| agctgtgacc gtctccggga gctgcatgtg tcagaggttt tcaccgtcat caccgaaacg | 8280 |
| cgcgaggcag cagatcaatt cgcgcgcgaa ggcgaagcgg catgcataat gtgcctgtca | 8340 |
| aatggacgaa gcaggattc tgcaaaccct atgctactcc gtcaagccgt caattgtctg | 8400 |
| attcgttacc aattatgaca acttgacggc tacatcattc acttttctt cacaaccggc | 8460 |
| acggaactcg ctcgggctgg ccccggtgca tttttttaaat acccgcgaga atagagttg | 8520 |
| atcgtcaaaa ccaacattgc gaccgacggt ggcgatagc atccgggtgg tgctcaaaag | 8580 |
| cagcttcgcc tggctgatac gttggtcctc gcgccagctt aagacgctaa tccctaactg | 8640 |
| ctggcggaaa agatgtgaca gacgcgacgg cgacaagcaa acatgctgtg cgacgctggc | 8700 |
| gat | 8703 |

<210> SEQ ID NO 35
<211> LENGTH: 4668
<212> TYPE: DNA
<213> ORGANISM: Artificial Sequence
<220> FEATURE:
<223> OTHER INFORMATION: pMC-CMV-SV40-polyA O1P1-3C(wt) (without bacterial backbone)

<400> SEQUENCE: 35

| | |
|---|---|
| cccttgggct ccccgggcgc gactagtgaa ttgatactag tattatgccc agtacatgac | 60 |
| cttatgggac tttcctactt ggcagtacat ctacgtatta gtcatcgcta ttaccatggt | 120 |
| gatgcggttt tggcagtaca tcaatgggcg tggatagcgg tttgactcac ggggatttcc | 180 |
| aagtctccac cccattgacg tcaatgggag tttgttttgg caccaaaatc aacgggactt | 240 |
| tccaaaatgt cgtaacaact ccgccccatt gacgcaaatg ggcggtaggc gtgtacggtg | 300 |
| ggaggtttat ataagcagag ctcgtttagt gaaccgtcag atcgcctgga gacgccatcc | 360 |
| acgctgtttt gacctccata gaagattcta gagtcgacgc ggccgcggat ccgccgccgc | 420 |
| catgggagcc gggcaatcca gcccggcaac cgggtcacag aaccaatcag gcaacactgg | 480 |
| gagcatcatc aacaattact acatgcagca gtaccaaaac tctatggaca cacaacttgg | 540 |
| tgacaacgct acaagcggag gctcaaacga ggggtccacg gacacaacct ccacccacac | 600 |
| aaccaacact cagaacaacg actggttctc gaagctggcc agttccgctt tcagcggtct | 660 |
| tttcggcgct cttctcgccg acaagaaaac cgaggagacc actcttcttg aggaccgcat | 720 |
| cctcactact cgtaacggac acaccacctc gacaacccag tcgagcgtag gagtcacata | 780 |
| cgggtatgca acggctgagg atttcgtgag cgggccaaac acctctggtc ttgagaccag | 840 |
| ggttgcccag gcagagcggt tctttaaaac ccacctgttc gactgggtca caagtgaccc | 900 |
| gttcggacgg tgccacctgc tagaacttcc aactgaccac aaaggtgtct atggcagcct | 960 |
| gaccgactcg tatgcttata tgaggaacgg ctggatgtt gaagtcactg ctgtgggaaa | 1020 |
| tcagttcaat ggaggatgcc tgttggtggc tatggtgcca gaactttgct ccatacagaa | 1080 |

```
gagggagctg taccagctca cgctctttcc tcaccagttc atcaaccctc ggacgaacat   1140
gacagcacac atcactgtgc cctttgttgg cgtcaaccgt tatgaccagt acaaggtaca   1200
caaaccttgg accctcgtgg ttatggttgt agccccctg accgtcaaca gtgaaggtgc    1260
cccgcaaatc aaggtgtatg ccaacatcgc acctaccaac gtacacgtcg cgggtgagtt   1320
cccttccaaa gagggatct tccctgtggc ttgcagcgat ggttatggcg gtctggtgac    1380
aactgacccg aaaacggctg accccgctta cgggaaagtg tttaaccccc ccgcaacat    1440 gttgccgggg cggttcacca attttcttga cgtggctgag gcgtgcccca cgtttctcca   1500
cttcgagggt gacgtgccat acgtgaccac gaagacggat tcagacaggg tgctcgctca   1560
gttcgacttg tctttggcag caaagcacat gtccaacacc ttccttgcag gtctcgccca   1620
gtactacaca cagtacagcg gcaccatcaa cctgcacttc atgttcacag gcctactga    1680 cgcgaaggcg cgttacatga ttgcgtatgc tcctcctggc atggaaccac ctaaaacgcc   1740
agaggcggct gcccactgca tccatgctga atgggacaca gggttgaact caaaattcac   1800
attttcaatc ccttaccttt cggcggctga ttacgcttac acagcgtctg acactgctga   1860
gaccacaaat gtacagggat gggttttgcct gtttcaaata acacacggga aagctgacgg   1920
cgacgcactg gtcgttttgg ccagcgccgg aaaggacttt gagctgcgcc tgccggtgga   1980
tgctcgcaca cagactacct cagcgggcga gtcagcagac cccgtgaccg ccaccgttga   2040
gaattacggt ggcgagacac aggtccagag gcgccaacac acggacgtgt catttatatt   2100
agacagattt gtgaaagtga caccaaaaga ccaaattaat gtattggacc tgatgcaaac   2160
ccctgctcac actttggtgg gagcactcct tcgtactgcc acttactatt tcgctgactt   2220
agaggtggca gtgaagcacg agggaaacct cacctgggtg ccgaacgggg cgcctgaagc   2280
ggcgttggac aacaccacca acccaacagc ttaccacaag gcaccactca cccgacttgc   2340
actgccttac acggcgccac accgcgtgtt ggctactgtt tacaacggga acagcaagta   2400
tggtgacggc acggtggcca atgtgagagg tgatctgcaa gtgttggccc agaaggcggc   2460
gagagcgctg cctacctcct tcaactacgg tgccattaaa gctactcggg tgactgaact   2520
gctttaccgc atgaagaggg ctgagacata ctgtccccgg cctcttttgg ccattcaccc   2580
ggaccaggct agacacaagc agaagattgt ggctccggtg aaacagcttc taaattttga   2640
cctgctcaaa ttggcgggag atgtggagtc caaccctggg cccagcggcc gcatgagtgg   2700
tgccccaccg accgacttgc aaaagatggt catgagcaac actaagcctg ttgagctcat   2760
ccttgacggt aagacggtgg ccatctgctg cgccaccgga gtgtttggta ctgcctacct   2820
cgtgcctcgt cacctttcg cagaaaagta cgacaggatc atgttggacg gcagggccat    2880
gacagacagt gactacagag tgtttgagtt tgagattaaa gtaaaaggac aggacatgct   2940
ctcagacgct gcgctcatgg tgctccaccg tggcaaccgt gtgagagaca tcacgaaaca   3000
cttccgtgat acagcaagaa tgaagaaagg taccccccgtt gtcggcgtga tcaacaacgc   3060
cgacgttggg agactgattt tctccggtga ggccctcacc tacaaggaca ttgtagtgtg   3120
catggatgga gacaccatgc cgggcctatt tgcctacaga gccgctacca aggctggcta   3180
ctgtggagga gccgttcttg ccaaggacgg agctgacaca tttatcgtcg gcactcactc   3240
cgcaggaggc aatggagtcg ggtactgctc atgcgtatct aggtccatgc tcttgaagat   3300
gaaggcacac attgaccccg aaccacacca cgagtaggaa ttcgctagct cgacaatcaa   3360
cctctggatt acaaaatttg tgaaagattg actggtattc ttaactatgt tgctcctttt   3420
```

```
acgctatgtg gatacgctgc tttaatgcct ttgtatcatg ctattgcttc ccgtatggct    3480
ttcattttct cctccttgta taaatcctgg ttgctgtctc tttatgagga gttgtggccc    3540
gttgtcaggc aacgtggcgt ggtgtgcact gtgtttgctg acgcaacccc cactggttgg    3600
ggcattgcca ccacctgtca gctcctttcc gggactttcg ctttccccct cccattgcc     3660 acggcggaac tcatcgccgc ctgccttgcc cgctgctgga caggggctcg gctgttgggc    3720
actgacaatt ccgtggtgtt gtcggggaaa tcatcgtcct ttccttggct gctcgcctgt    3780
gttgccacct ggattctgcg cgggacgtcc ttctgctacg tcccttcggc cctcaatcca    3840
gcggaccttc cttcccgcgg cctgctgccg gctctgcggc ctcttccgcg tcttcgcctt    3900
cgccctcaga cgagtcggat ctcccttggg gccgcctccc cgcctggtac ctttaagacc    3960
aatgacttac aaggcagctg tagatcttag ccactttta aaagaaaagg ggggactgga    4020
agggctaatt cactcccaac gaagataaga tctgcttttt gcttgtactg ggtctctctg    4080
gttagaccag atctgagcct gggagctctc tggctaacta gggaacccac tgcttaagcc    4140
tcaataaagc ttgccttgag tgcttcaagt agtgtgtgcc cgtctgttgt gtgactctgg    4200
taactagaga tccctcagac ccttttagtc agtgtggaaa atctctagca gtagtagttc    4260
atgtcatctt attattcagt atttataact tgcaaagaaa tgaatatcag agagtgagag    4320
gaacttgttt attgcagctt ataatggtta caaataaagc aatagcatca caaatttcac    4380
aaataaagca tttttttcac tgcattctag ttgtggtttg tccaaactca tcaatgtatc    4440
ttatcatgtc tggctctagc tatcccgccc ctaactccgc ccatcccgcc cctaactccg    4500
cccagttccg cccattctcc gccccatggc tgactaattt tttttattta tgcagaggcc    4560
gaggccgcct cggcctctga gctattccag aagtagtgag gaggcttttt tggaggccta    4620
gacttttgca gatcgaccca tgggggcccg ccccaactgg ggtaacct                 4668
```

<210> SEQ ID NO 36
<211> LENGTH: 28
<212> TYPE: DNA
<213> ORGANISM: Artificial Sequence
<220> FEATURE:
<223> OTHER INFORMATION: Synthetic primer - AscI-Kzk-Gluc-F

<400> SEQUENCE: 36

```
ttggcgcgcc gccaccatgg gagtcaaa                                          28
```

<210> SEQ ID NO 37
<211> LENGTH: 26
<212> TYPE: DNA
<213> ORGANISM: Artificial Sequence
<220> FEATURE:
<223> OTHER INFORMATION: Synthetic primer - Gluc-R-NotI

<400> SEQUENCE: 37

```
gcggccgctt agtcaccacc ggcccc                                            26
```

<210> SEQ ID NO 38
<211> LENGTH: 6430
<212> TYPE: DNA
<213> ORGANISM: Artificial Sequence
<220> FEATURE:
<223> OTHER INFORMATION: pMC-CMV-SV40-polyA SGLuc (with bacterial
      backbone)

<400> SEQUENCE: 38

```
acattaccct gttatcccta gatacattac cctgttatcc cagatgacat accctgttat     60
```

-continued

```
ccctagatga cattaccctg ttatcccaga tgacattacc ctgttatccc tagatacatt    120
accctgttat cccagatgac atacccgtt atccctagat gacattaccc tgttatccca     180
gatgacatta ccctgttatc cctagataca ttaccctgtt atcccagatg acatccctg    240 ttatccctag atgacattac cctgttatcc cagatgacat taccctgtta tccctagata    300
cattaccctg ttatcccaga tgacataccc tgttatccct agatgacatt accctgttat    360
cccagatgac attaccctgt tatccctaga tacattaccc tgttatccca gatgacatac    420
cctgttatcc ctagatgaca ttaccctgtt atcccagatg acattaccct gttatccta    480 gatacattac cctgttatcc cagatgacat accctgttat ccctagatga cattaccctg    540
ttatcccaga tgacattacc ctgttatccc tagatacatt accctgttat cccagatgac    600 atacctgtt atccctagat gacattaccc tgttatccca gatgacatta ccctgttatc    660
cctagataca ttaccctgtt atcccagatg acatacctg ttatccctag atgacattac    720
cctgttatcc cagataaact caatgatgat gatgatgatg tcgagactc agcggccgcg    780 gtgccagggc gtgcccttgg ctcccccggg cgcgactagt gaattgatac tagtattatg    840
cccagtacat gaccttatgg gactttccta cttggcagta catctacgta ttagtcatcg    900
ctattaccat ggtgatgcgg ttttggcagt acatcaatgg gcgtggatag cggtttgact    960 cacgggatt tccaagtctc caccccattg acgtcaatgg gagtttgttt tggcaccaaa     1020
atcaacggga ctttccaaaa tgtcgtaaca actccgcccc attgacgcaa atgggcggta    1080
ggcgtgtacg gtgggaggtt tatataagca gagctcgttt agtgaaccgt cagatcgcct    1140
ggagacgcca tccacgctgt tttgacctcc atagaagatt ctagagtcga cgcggccgcg    1200
gatccttgct agcctcgaga cgcgtgattt tggcgcgccg ccaccatggg agtcaaagtt    1260
ctgtttgccc tgatctgcat cgctgtggcc gaggccaagc ccaccgagaa caacgaagac    1320
ttcaacatcg tggccgtggc cagcaacttc gcgaccacgg atctcgatgc tgaccgcggg    1380
aagttgcccg gcaagaagct gccgctggag gtgctcaaag agatggaagc caatgcccgg    1440
aaagctggct gcaccagggg ctgtctgatc tgcctgtccc acatcaagtg cacgcccaag    1500
atgaagaagt ggctcccagg acgctgccac acctacgaag cgacaaaga gtccgcacag    1560 ggcggcatag gcgaggcgat cgtcgacatt cctgagattc tgggttcaa ggacttggag    1620 cccatggagc agttcatcgc acaggtcgat ctgtgtgtgg actgcacaac tggctgcctc    1680
aaagggcttg ccaacgtgca gtgttctgac ctgctcaaga gtggctgcc gcaacgctgt    1740 gcgacctttg ccagcaagat ccagggccag gtggacaaga tcaaggggc cggtggtgac    1800 taagcggacg caaaatcagc ctcaatcttt cccggggta ccgtcgactg cggccgcgaa    1860
ttcgctagct cgacaatcaa cctctggatt acaaaatttg tgaaagattg actggtattc    1920
ttaactatgt tgctcctttt acgctatgtg gatacgctgc tttaatgcct ttgtatcatg    1980
ctattgcttc ccgtatggct ttcattttct cctccttgta taaatcctgg ttgctgtctc    2040
tttatgagga gttgtggccc gttgtcaggc aacgtggcgt ggtgtgcact gtgtttgctg    2100
acgcaacccc cactggttgg ggcattgcca ccacctgtca gctccttttcc gggactttcg    2160 ctttcccct cctattgcc acggcggaac tcatcgccgc ctgccttgcc cgctgctgga    2220
caggggctcg gctgttgggc actgacaatt ccgtggtgtt gtcggggaaa tcatcgtcct    2280
ttccttggct gctcgcctgt gttgccacct ggattctgcg cggacgtcc ttctgctacg    2340 tcccttcggc cctcaatcca gcggaccttc cttcccgcgg cctgctgccg gctctgcggc    2400
ctcttccgcg tcttcgcctt cgccctcaga cgagtcggat ctcccttgg gccgcctccc    2460
```

```
cgcctggtac ctttaagacc aatgacttac aaggcagctg tagatcttag ccactttta    2520 aaagaaaagg ggggactgga agggctaatt cactcccaac gaagataaga tctgcttttt    2580
gcttgtactg ggtctctctg gttagaccag atctgagcct gggagctctc tggctaacta    2640
gggaacccac tgcttaagcc tcaataaagc ttgccttgag tgcttcaagt agtgtgtgcc    2700
cgtctgttgt gtgactctgg taactagaga tccctcagac ccttttagtc agtgtggaaa    2760
atctctagca gtagtagttc atgtcatctt attattcagt atttataact tgcaaagaaa    2820
tgaatatcag agagtgagag gaacttgttt attgcagctt ataatggtta caaataaagc    2880
aatagcatca caaatttcac aaataaagca tttttttcac tgcattctag ttgtggtttg    2940
tccaaactca tcaatgtatc ttatcatgtc tggctctagc tatcccgccc ctaactccgc    3000
ccatcccgcc cctaactccg cccagttccg cccattctcc gccccatggc tgactaattt    3060
tttttattta tgcagaggcc gaggccgcct cggcctctga gctattccag aagtagtgag    3120
gaggcttttt tggaggccta acttttgca gatcgaccca tggggccccg cccaactgg      3180 ggtaaccttt gagttctctc agttgggggt aatcagcatc atgatgtggt accacatcat    3240
gatgctgatt ataagaatgc ggccgccaca ctctagtgga tctcgagtta ataattcaga    3300
agaactcgtc aagaaggcga tagaaggcga tgcgctgcga atcgggagcg cgataccgt    3360 aaagcacgag gaagcggtca gcccattcgc cgccaagctc ttcagcaata tcacgggtag    3420
ccaacgctat gtcctgatag cggtccgcca cacccagccg gccacagtcg atgaatccag    3480
aaaagcggcc attttccacc atgatattcg gcaagcaggc atcgccatgg gtcacgacga    3540
gatcctcgcc gtcgggcatg ctcgccttga gcctggcgaa cagttcggct ggcgcgagcc    3600
cctgatgctc ttcgtccaga tcatcctgat cgacaagacc ggcttccatc cgagtacgtg    3660
ctcgctcgat gcgatgtttc gcttggtggt cgaatgggca ggtagccgga tcaagcgtat    3720
gcagccgccg cattgcatca gccatgatgg atactttctc ggcaggagca aggtgagatg    3780
acaggagatc ctgccccggc acttcgccca atagcagcca gtcccttccc gcttcagtga    3840
caacgtcgag cacagctgcg caaggaacgc ccgtcgtggc cagccacgat agccgcgctg    3900
cctcgtcttg cagttcattc agggcaccgg acaggtcggt cttgacaaaa agaaccgggc    3960
gcccctgcgc tgacagccgg aacacgcgg catcagagca gccgattgtc tgttgtgccc    4020
agtcatagcc gaatagcctc tccacccaag cggccggaga acctgcgtgc aatccatctt    4080
gttcaatcat gcgaaacgat cctcatcctg tctcttgatc agagcttgat cccctgcgcc    4140
atcagatcct ggcggcgag aaagccatcc agtttacttt gcagggcttc ccaaccttac    4200
cagagggcgc cccagctggc aattccggtt cgcttgctgt ccataaaacc gcccagtcta    4260
gctatcgcca tgtaagccca ctgcaagcta cctgctttct ctttgcgctt gcgttttccc    4320
ttgtccagat agcccagtag ctgacattca tccggggtca gcaccgtttc tgcggactgg    4380
ctttctacgt gctcgagggg ggccaaacgg tctccagctt ggctgttttg gcggatgaga    4440
gaagattttc agcctgatac agattaaatc agaacgcaga agcggtctga taaaacagaa    4500
tttgcctggc ggcagtagcg cggtggtccc acctgacccc atgccgaact cagaagtgaa    4560
acgccgtagc gccgatggta gtgtgggtc tccccatgcg agagtaggga actgccaggc    4620
atcaaataaa acgaaaggct cagtcgaaag actgggcctt tcgttttatc tgttgtttgt    4680
cggtgaacgc tctcctgagt aggacaaatc cgccgggagc ggatttgaac gttgcgaagc    4740
aacggcccgg agggtggcgg gcaggacgcc cgccataaac tgccaggcat caaattaagc    4800
```

-continued

| | |
|---|---|
| agaaggccat cctgacggat ggccttttg cgtttctaca aactcttttg tttatttttc | 4860 |
| taaatacatt caaatatgta tccgctcatg accaaaatcc cttaacgtga gttttcgttc | 4920 |
| cactgagcgt cagaccccgt agaaaagatc aaaggatctt cttgagatcc ttttttttctg | 4980 |
| cgcgtaatct gctgcttgca acaaaaaaaa ccaccgctac cagcggtggt ttgtttgccg | 5040 |
| gatcaagagc taccaactct ttttccgaag gtaactggct tcagcagagc gcagatacca | 5100 |
| aatactgtcc ttctagtgta gccgtagtta ggccaccact tcaagaactc tgtagcaccg | 5160 |
| cctacatacc tcgctctgct aatcctgtta ccagtggctg ctgccagtgg cgataagtcg | 5220 |
| tgtcttaccg ggttggactc aagacgatag ttaccggata aggcgcagcg gtcgggctga | 5280 |
| acggggggtt cgtgcacaca gcccagcttg gagcgaacga cctacaccga actgagatac | 5340 |
| ctacagcgtg agctatgaga aagcgccacg cttcccgaag ggagaaaggc ggacaggtat | 5400 |
| ccggtaagcg gcagggtcgg aacaggagag cgcacgaggg agcttccagg gggaaacgcc | 5460 |
| tggtatcttt atagtcctgt cgggtttcgc cacctctgac ttgagcgtcg attttttgtga | 5520 |
| tgctcgtcag ggggggcggag cctatggaaa aacgccagca acgcggcctt tttacggttc | 5580 |
| ctggcctttt gctggccttt tgctcacatg ttctttcctg cgttatcccc tgattctgtg | 5640 |
| gataaccgta ttaccgcctt tgagtgagct gataccgctc gccgcagccg aacgaccgag | 5700 |
| cgcagcgagt cagtgagcga ggaagcggaa gagcgcctga tgcggtattt tctccttacg | 5760 |
| catctgtgcg gtatttcaca ccgcatatgg tgcactctca gtacaatctg ctctgatgcc | 5820 |
| gcatagttaa gccagtatac actccgctat cgctacgtga ctgggtcatg gctgcgcccc | 5880 |
| gacacccgcc aacacccgct gacgcgccct gacgggcttg tctgctcccg gcatccgctt | 5940 |
| acagacaagc tgtgaccgtc tccgggagct gcatgtgtca gaggttttca ccgtcatcac | 6000 |
| cgaaacgcgc gaggcagcag atcaattcgc gcgcgaaggc gaagcggcat gcataatgtg | 6060 |
| cctgtcaaat ggacgaagca gggattctgc aaaccctatg ctactccgtc aagccgtcaa | 6120 |
| ttgtctgatt cgttaccaat tatgacaact tgacggctac atcattcact ttttcttcac | 6180 |
| aaccggcacg gaactcgctc gggctggccc cggtgcattt tttaaatacc cgcgagaaat | 6240 |
| agagttgatc gtcaaaacca acattgcgac cgacggtggc gataggcatc cgggtggtgc | 6300 |
| tcaaaagcag cttcgcctgg ctgatacgtt ggtcctcgcg ccagcttaag acgctaatcc | 6360 |
| ctaactgctg gcggaaaaga tgtgacagac gcgacggcga caagcaaaca tgctgtgcga | 6420 |
| cgctggcgat | 6430 |

<210> SEQ ID NO 39
<211> LENGTH: 2395
<212> TYPE: DNA
<213> ORGANISM: Artificial Sequence
<220> FEATURE:
<223> OTHER INFORMATION: pMC-CMV-SV40-polyA SGLuc (without bacterial
      backbone)

<400> SEQUENCE: 39

| | |
|---|---|
| cccttgggct ccccgggcgc gactagtgaa ttgatactag tattatgccc agtacatgac | 60 |
| cttatgggac tttcctactt ggcagtacat ctacgtatta gtcatcgcta ttaccatggt | 120 |
| gatgcggttt tggcagtaca tcaatgggcg tggatagcgg tttgactcac ggggatttcc | 180 |
| aagtctccac cccattgacg tcaatgggag tttgttttgg caccaaaatc aacgggactt | 240 |
| tccaaaatgt cgtaacaact ccgccccatt gacgcaaatg ggcggtaggc gtgtacggtg | 300 |
| ggaggtttat ataagcagag ctcgtttagt gaaccgtcag atcgcctgga gacgccatcc | 360 |

-continued

```
acgctgtttt gacctccata gaagattcta gagtcgacgc ggccgcggat ccttgctagc    420
ctcgagacgc gtgattttgg cgcgccgcca ccatgggagt caaagttctg tttgccctga    480
tctgcatcgc tgtggccgag gccaagccca ccgagaacaa cgaagacttc aacatcgtgg    540
ccgtggccag caacttcgcg accacggatc tcgatgctga ccgcgggaag ttgcccggca    600
agaagctgcc gctggaggtg ctcaaagaga tggaagccaa tgcccggaaa gctggctgca    660
ccaggggctg tctgatctgc ctgtcccaca tcaagtgcac gcccaagatg aagaagtggc    720
tcccaggacg ctgccacacc tacgaaggcg acaaagagtc cgcacagggc ggcataggcg    780
aggcgatcgt cgacattcct gagattcctg ggttcaagga cttggagccc atggagcagt    840
tcatcgcaca ggtcgatctg tgtgtggact gcacaactgg ctgcctcaaa gggcttgcca    900
acgtgcagtg ttctgacctg ctcaagaagt ggctgccgca acgctgtgcg acctttgcca    960
gcaagatcca gggccaggtg gacaagatca aggggccgg tggtgactaa gcggacgcaa   1020
aatcagcctc aatctttccc gggggtaccg tcgactgcgg ccgcgaattc gctagctcga   1080
caatcaacct ctgattaca aaatttgtga aagattgact ggtattctta actatgttgc    1140
tcctttacg ctatgtggat acgctgcttt aatgcctttg tatcatgcta ttgcttccg    1200
tatggctttc attttctcct ccttgtataa atcctggttg ctgtctcttt atgaggagtt   1260
gtggcccgtt gtcaggcaac gtggcgtggt gtgcactgtg tttgctgacg caaccccac    1320
tggttggggc attgccacca cctgtcagct cctttccggg actttcgctt tccccctccc   1380
tattgccacg gcggaactca tcgccgcctg ccttgcccgc tgctggacag gggctcggct   1440
gttgggcact gacaattccg tggtgttgtc ggggaaatca tcgtcctttc cttggctgct   1500
cgcctgtgtt gccacctgga ttctgcgcgg gacgtccttc tgctacgtcc cttcggccct   1560
caatccagcg gaccttcctt cccgcggcct gctgccggct ctgcgcctc ttccgcgtct   1620
tcgccttcgc cctcagacga gtcggatctc cctttgggcc gcctcccgc ctggtacctt    1680
taagaccaat gacttacaag gcagctgtag atcttagcca cttttaaaa gaaaagggg   1740
gactggaagg gctaattcac tcccaacgaa gataagatct gcttttgct tgtactgggt    1800
ctctctggtt agaccagatc tgagcctggg agctctctgg ctaactaggg aacccactgc   1860
ttaagcctca ataaagcttg ccttgagtgc ttcaagtagt gtgtgcccgt ctgttgtgtg   1920
actctggtaa ctagagatcc ctcagaccct tttagtcagt gtggaaaatc tctagcagta   1980
gtagttcatg tcatcttatt attcagtatt tataacttgc aaagaaatga atatcagaga   2040
gtgagaggaa cttgtttatt gcagcttata atggttacaa ataaagcaat agcatcacaa   2100
atttcacaaa taaagcattt ttttcactgc attctagttg tggtttgtcc aaactcatca   2160
atgtatctta tcatgtctgg ctctagctat cccgcccta actccgccca tcccgcccct    2220
aactccgccc agttccgccc attctccgcc ccatggctga ctaattttt ttatttatgc    2280
agaggccgag gccgcctcgg cctctgagct attccagaag tagtgaggag ctttttgg    2340
aggcctagac ttttgcagat cgacccatgg gggcccgccc caactgggt aacct        2395
```

METHODS OF MAKING AND USING VACCINES UTILIZING MINICIRCLE DNA EXPRESSION VECTORS FOR PRODUCTION OF FOOT-AND-MOUTH-DISEASE VIRUS PROTEINS AND VIRUS-LIKE PARTICLES

GOVERNMENT RIGHTS

This invention was made with government support under HSHQPM-12-X-00013 and HSHQDC-14-F-00035 awarded by the U.S. Department of Homeland Security. The Government has certain rights in this invention.

SEQUENCE LISTING

The instant application contains a Sequence Listing which has been submitted in ASCII format via EFS-Web and is hereby incorporated by reference in its entirety. The ASCII copy is named DHS-067_Sequence_Listing.txt and is 96 KB in size.

BACKGROUND

Technical Field

The present disclosure relates to compositions and methods for the vaccination and diagnosis of foot-and-mouth disease. More specifically, the present disclosure relates to a minicircle vector that is expressed in a mammalian host cell to produce virus-like particles of foot-and-mouth disease virus (FMDV).

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The foot-and-mouth disease virus (FMDV), a prototypic aphthovirus within the Picornaviridae family, is the causative agent of a highly infectious and sometimes fatal disease that affects cloven-hoofed animals such as cattle, pigs, sheep, goats, deer and other animals with cloven hooves. There are seven major FMDV antigenically distinct virus serotypes (A, O, C, Asia 1 and South African Territories or SAT 1, 2 and 3) and multiple subtypes or topotypes exist within each serotype. Infection with any one serotype does not confer protective immunity against another. Serotype O is the most common serotype worldwide.

After an animal is infected with the FMDV, the first signs of illness usually appear within 2 to 14 days: high fever for 2-3 days followed by blisters inside the mouth and on the feet that may rupture and cause lameness.

FMD outbreaks cause significant agro-economic losses and severe implications for animal farming throughout much of the world. For example, the outbreak of FMD in the U.K. in 2001 was estimated to cost the U.K. £8 billion, including 6 million slaughtered livestock. Since the virus causing the disease is highly contagious and can be spread by infected livestock through aerosols, through contact with contaminated farming equipment, vehicles, clothing, or feed, and by domestic and wild predators, the containment of FMD demands considerable efforts in vaccination, strict monitoring, trade restrictions, and quarantines, and sometimes, the culling of animals.

BRIEF SUMMARY

According to a first aspect, the present disclosure provides a mutant nucleotide sequence that encodes a foot-and-mouth disease virus (FMDV) capsid polyprotein precursor, the mutant nucleotide sequence comprising a mutation that removed a restriction enzyme recognition site from a nucleotide sequence from which the mutant nucleotide sequence was formed.

In one or more embodiments, the nucleotide sequence comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G170, T338, T1518, C1578, T1593, C1665, C1836, C2010, A2190 and combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the restriction enzyme recognition site is selected from the group consisting of XbaI, XcmI, BsiWI, XhoI, BstEII, PflMI, AccI, NheI, SacII, PpuMI, AgeI, PvuII, NcoI, PstI, BstXI, AatI and combinations thereof.

In one or more embodiments, the FMDV is selected from the group consisting of O, A, C, Asia 1, SAT 1, SAT 2 and SAT 3 serotypes.

According to a second aspect, the present disclosure provides a vector comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In one or more embodiments, the protease is functionally able to cleave the FMDV capsid polyprotein precursor into a plurality of FMDV capsid proteins.

In one or more embodiments, the FMDV capsid proteins are selected from a group consisting of VP0, VP1, VP2, VP3, VP4, and combinations thereof.

In one or more embodiments, the transitional regulatory element is functional to reduce expression of the protease relative to the nucleotide sequence that encodes the protease.

In one or more embodiments, the vector expresses the protease.

In one or more embodiments, the vector comprises a minicircle vector,

In one or more embodiments, the vector comprises the nucleotide sequence of SEQ ID NO: 2.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the vector comprises the nucleotide sequence of SEQ ID NO: 3.

In one or more embodiments, the eukaryotic translation initiation nucleotide sequence comprises SEQ ID NO: 4.

In one or more embodiments, the eukaryotic translation initiation nucleotide sequence comprises SEQ ID NO: 5.

In one or more embodiments, the translational regulatory element comprises a DNA or RNA sequence responsible for a ribosomal frameshift.

In one or more embodiments, the DNA or RNA sequence responsible for a ribosomal frameshift is selected from the group consisting of an ALIL pseudoknot, an antizyme RNA frameshifting stimulation element, a coronavirus frameshifting stimulation element, a DnaX ribosomal frameshifting element, a HIV ribosomal frameshift signal, an insertion sequence IS1222 ribosomal frameshifting element, and a ribosomal frameshift.

In one or more embodiments, the DNA or RNA sequence responsible for a ribosomal frameshift is functional to mediate a translational frameshift in the protease in an amount of 90-95% of translated protease mRNA.

In one or more embodiments, the DNA or RNA sequence responsible for a ribosomal frameshift is functional to yield translation of no more than twenty percent (20%) of the nucleotide sequence that encodes the protease after translation.

In one or more embodiments, the DNA or RNA sequence responsible for a ribosomal frameshift is functional to yield translation of between five and ten percent (5-10%) of the nucleotide sequence that encodes the protease after translation.

In one or more embodiments, the nucleotide sequence that encodes the protease is fully translated and comprises a correct translation of the protease after translation.

In one or more embodiments, the DNA or RNA sequence responsible for a ribosomal frameshift comprises the nucleotide sequence of SEQ ID NO: 6.

In one or more embodiments, the nucleotide sequence that encodes a protease comprises the nucleotide sequence of SEQ ID NO: 7, and the amino acid sequence of the protease comprises SEQ ID NO: 8.

In one or more embodiments, the nucleotide sequence that encodes a protease comprises SEQ ID NO: 9.

In a third aspect, the present disclosure provides a transformed host cell comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the transformed host cell comprises a mammalian cell.

In one or more embodiments, the transformed host cell is functional to produce a virus like particle (VLP).

In one or more embodiments, the VLP comprises a FMDV VLP.

In a fourth aspect, the present disclosure provides virus like particle (VLP) comprising a polypeptide produced from expression of a vector comprising a mutant nucleotide sequence that encodes a foot-and-mouth disease virus (FMDV) capsid polyprotein precursor and includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In a fifth aspect, the present disclosure provides a method of vaccinating a mammal against a foot-and-mouth disease virus (FMDV), comprising administering a vector comprising a mutant nucleotide sequence which when expressed in a host cell of the mammal induces production of foot-and-mouth disease virus virus-like particles (VLP) by the host cell, the mutant nucleotide sequence encodes a FMDV capsid polyprotein precursor and includes a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the method further comprises administering an adjuvant with the vector.

In a sixth aspect, the present disclosure provides a method of determining whether a mammal is vaccinated against or infected with foot-and-mouth disease virus (FMDV) comprising detecting an antibody's presence in a sample from the mammal, and detecting an other antibody's presence or absence in the sample, the absence of the other antibody indicates vaccination of the mammal with a vector comprising a mutant nucleotide sequence which when expressed in a host cell of the mammal induces production of FMDV virus-like particles, the mutant nucleotide sequence encodes a FMDV capsid polyprotein precursor and a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mammal produced the antibody responsive to vaccination with the vector.

In one or more embodiments, the other antibody comprises a plurality of antibodies that do not include the antibody.

In one or more embodiments, the plurality of antibodies comprise antibodies against FMDV non-structural proteins.

In one or more embodiments, the plurality of antibodies are associated with FMDV infection.

In one or more embodiments, the detecting the antibody's presence implements an immunoassay.

In one or more embodiments, immunoassay comprises an enzyme linked immunosorbent assay (ELISA).

In one or more embodiments, the detecting the other antibody's presence or absence implements an immunoassay.

In one or more embodiments, the immunoassay comprises an enzyme linked immunosorbent assay (ELISA).

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

An appreciation of the disclosure and many of the attendant advantages thereof may be understood by reference to the accompanying drawings. Included in the drawings are the following figures:

FIG. 4 illustrates gene layouts of three inserts that were each individually cloned into a minicircle vector system.

DETAILED DESCRIPTION OF THE EMBODIMENTS

Overview

Figure 1:
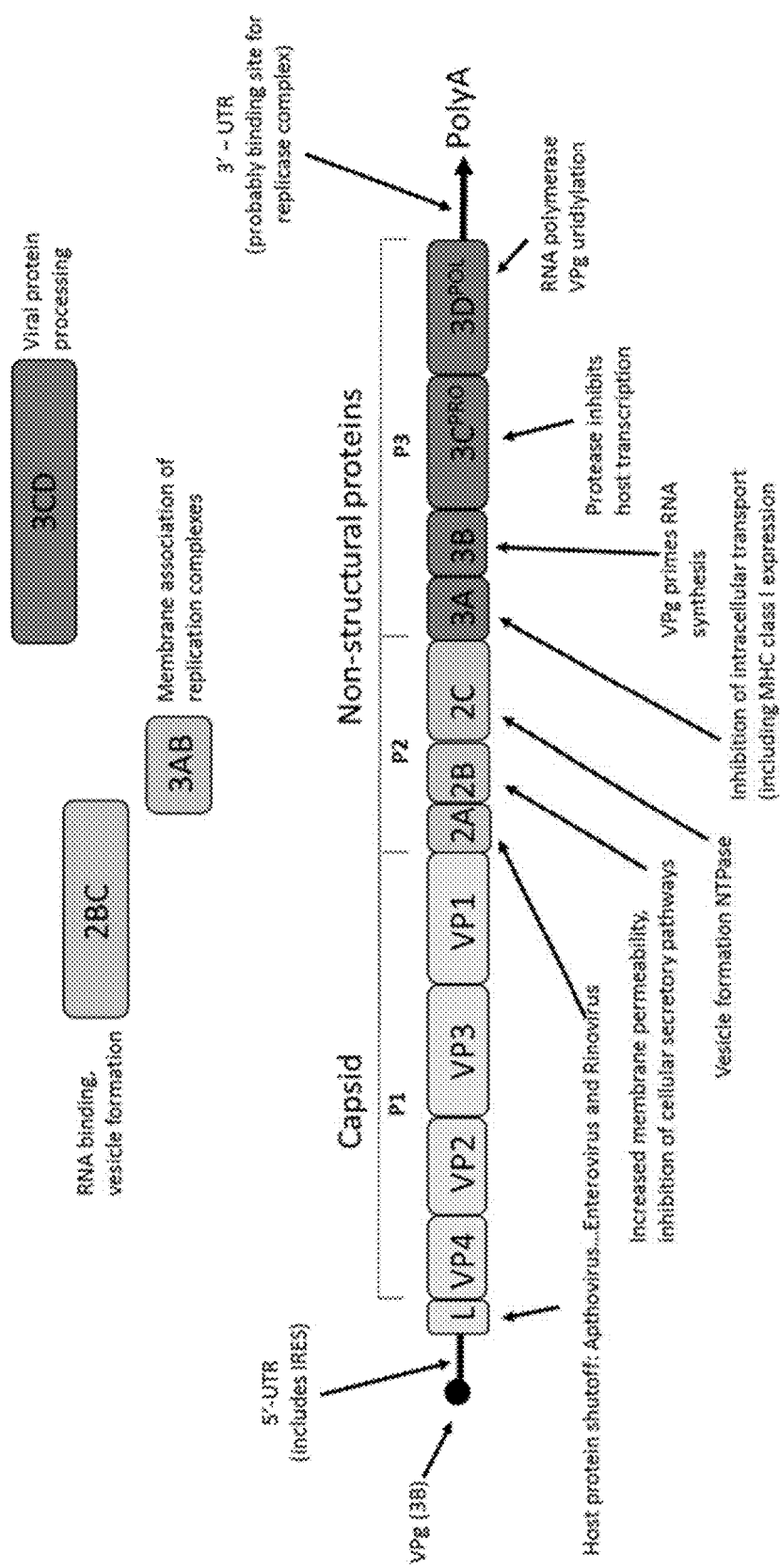
FIG. 1 is a diagrammatic representation of the picornavirus genome that includes translated capsid and other non-structural proteins.

Some vaccine includes the use of a whole virus that is either killed or inactivated, such as by chemically inactivating the virus, or is attenuated by various means. Vaccines are fraught with limitations and shortcomings, such as potential virus escape, vaccine instability (e.g., loss of immunogenicity during transportation and storage), short duration of immunity and the use of multiple antigens (e.g., dozens) to address viral mutation, evolution and antigenic diversity. Furthermore, the set-up and running costs of the vaccine production facilities are very high, and the antibody profiles animals vaccinated with the whole virus may not be easily distinguished from those of infected animals.

Description

Referring now to the drawings, wherein like reference numerals designate identical or corresponding parts throughout the several views.

For purposes of the present invention, "foot-and-mouth-disease virus" or the acronym FMDV refers to any of the seven major FMDV antigenically distinct virus serotypes, i.e. A, O, C, Asia 1 and South African Territories 1, 2 and 3 as well as the multiple subtypes or topotypes exist within each serotype. Infection with any one serotype does not confer protective immunity against another. The FMDV is a non-enveloped picornavirus (belonging to the genus Aphthovirus of the family Picornaviridae) with a single-stranded genomic RNA of between 7,500 to 8,000 nucleotides or approximately between 7,500 to 8,000 nucleotides, approximately 7,500 nucleotides, or approximately 8,000 nucleotides. The capsid, which is the protein shell of the virus, is made up of 60 copies of each of the four structural proteins VP1, VP2, VP3 and VP4 (see FIG. 1). In embodiments, during assembly, P1, a 95-kDa capsid polyprotein precursor is cleaved by the viral 3C protease to ultimately yield VP1, VP2, VP3 and VP4. As shown in FIG. 1, apart from the 3C protease, the FMDV also expresses several other non-structural or non-capsid proteins (e.g. 2A-C, 3A-D) that can be involved in virus replication and various cellular functions.

The present disclosure provides compositions comprising recombinant foot-and-mouth disease virus (FMDV) nucleic acids and/or proteins for use in vaccine formulations and diagnostic reagents, as well as methods of preparing the compositions.

In particular, these compositions include mutant FMDV nucleotide sequences and transgene expression cassettes. In some embodiments, the compositions further comprise vehicles to carry and transfer the transgene expression cassette such as vectors (preferably minicircle vectors) and host cells (preferably mammalian cells) wherein the transgene expression cassette may be expressed and/or replicated.

For purposes of the present disclosure, a "nucleotide sequence" or "nucleic acid sequence" is a succession of letters that indicate the order of nucleotides or nucleic acids within a DNA (using GACT) or RNA molecule (using GACU). The DNA or RNA molecule may be single or double stranded and may be genomic, recombinant, mRNA or cDNA.

For purposes of the present disclosure, a "transgene expression cassette" or "transgene expression construct" is a nucleic acid sequence that has been artificially constructed to comprise one or more functional units (e.g. promoter, control element, consensus sequence, translational frame-shift sequence, protein encoding gene etc.) not found together in nature, and is capable of directing the expression of any RNA transcript in an organism that the cassette has been transferred to, including gene encoding sequence(s) of interest as well as non-translated RNAs, such as shRNAs, microRNAs, siRNAs, anti-sense RNAs. A transgene expression cassette may be single- or double-stranded and circular or linear. A transgene expression cassette can be constructed, inserted or cloned into a "vector", which serves as a vehicle for transferring, replicating and/or expressing nucleic acid sequences in target cells.

The transgene expression cassette according to the disclosure can be constructed as a single open reading frame. The transgene expression cassette includes a consensus nucleotide sequence for eukaryotic translation initiation (e.g., Kozak consensus sequence), a nucleotide sequence that encodes a FMDV capsid polyprotein precursor that contains at least one mutation to eliminate a restriction enzyme recognition site, a nucleotide sequence that encodes a protease that cleaves the capsid polyprotein precursor and a translational regulatory element to regulate the expression of the protease.

The transgene expression cassette described in accordance with embodiments described herein does not encode the complete FMDV genome and therefore cannot cause an accidental FMD outbreak during manufacture, or administration of the vaccine containing the transgene expression cassette.

Furthermore, the transgene expression cassette encodes only the P1 and 3C FMDV viral proteins. Animals treated with a vaccine containing the transgene expression cassette will not produce antibodies to other FMDV viral proteins that are expressed during a natural FMDV infection. For example, if the transgene expression cassette contains a nucleotide sequence that encodes the 2B protein, the animal treated with the vaccine containing the transgene expression cassette containing a nucleotide sequence that encodes the 2B protein will only produce antibodies for the 2B protein and not antibodies for other viral proteins such as 2C, 3B, 3D, etc. The difference in antibody profiles produced after natural infection compared to vaccination with the transgene expression cassette confers the ability to differentiate infected animals from vaccinated animals and vice versa.

Figure 2:
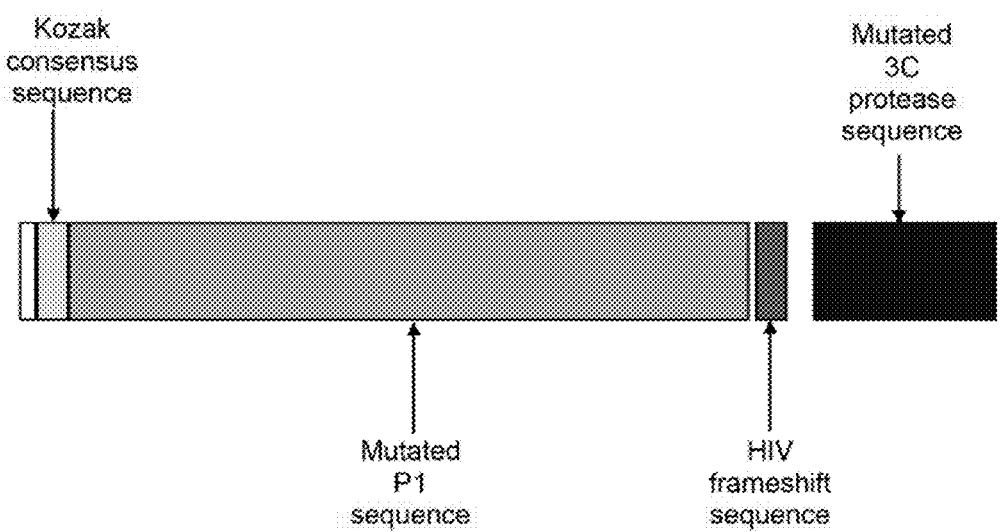
FIG. 2 illustrates the organization and design of the multiple functional units of a transgene expression cassette according to one embodiment.

FIG. 2 shows an embodiment of the transgene expression cassette that is arranged as follows: Kozak consensus sequence-Mutated P1 nucleotide sequence from FMDV-HIV frameshift sequence-Mutated 3C protease nucleotide sequence from FMDV.

In one or more embodiments, the nucleotide sequence of the transgene expression cassette comprises SEQ ID NO: 2.

The Kozak consensus sequence is a sequence which occurs in eukaryotic mRNA and, in one or more embodiments, comprises SEQ ID NO: 4. The Kozak consensus sequence plays a major role in the initiation of the translation process. In some instances the Kozak consensus sequence plays an essential role in initiation of the translation process, e.g., it is substantially the sole determining factor in initiation of the translation process.

In one or more embodiments, the Kozak consensus sequence is a Kozak eukaryotic translation initiation sequence comprising SEQ ID NO: 5.

In principle, effective FMDV vaccines can be produced from recombinant VLPs. However, the formation of stable VLPs in host cells at concentrations high enough to stimulate immune responses are hindered by the viral 3C protease. The 3C protease is used for proper processing and cleaving of the P1 polyprotein precursor, and has been found to be toxic to the host cells. Furthermore, the empty recombinant particles such as empty capsids tend to be less stable than in comparison to virus particles containing nucleic acid.

In some embodiments, the expression of the 3C protease from the transgene expression cassette is down regulated in such a way so the levels of enzyme are reduced or the expressed enzyme is not cytotoxic yet maintains the P1 cleavage activity for capsid formation. This may be achieved by engineering of the enzyme by rational design (e.g., site-directed mutagenesis) and/or random mutagenesis (e.g., directed evolution followed by screening of the desired enzyme properties) wherein one or more mutations may be introduced to the recombinant gene that encodes the protease. In certain embodiments, the 3C protease contains a mutation at cysteine residue 142. The cysteine may be substituted by another residue, for example, a threonine or an alanine.

In one or more embodiments, the nucleotide sequence of the mutated 3C protease comprises SEQ ID NO: 9 and the amino acid sequence of the mutated 3C protease comprises SEQ ID NO: 10.

In one or more embodiments, the 3C protease in the transgene expression cassette is derived from FMDV Asia Lebanon 1989 strain (serotype Asia-1).

In one or more embodiments, the 3C protease in the transgene expression cassette is derived from FMDV A22 Iraq strain (serotype A).

Alternatively, the expression of 3C protease may be controlled or suppressed with a translational element or a DNA or RNA sequence responsible for a ribosomal frameshift such as ALIL pseudoknot, antizyme RNA frameshifting stimulation element, coronavirus frameshifting stimulation element, DnaX ribosomal frameshifting element, HIV ribosomal frameshift signal, insertion sequence IS1222 ribosomal frameshifting element and a ribosomal frameshift. The DNA or RNA sequence responsible for a ribosomal frameshift may be located upstream of the nucleotide sequence that encodes the protease and downstream of the nucleotide sequence that encodes the capsid polyprotein precursor in the transgene expression cassette, and may cause a frameshift event of occurring in 80-98% of the total translation events. In certain embodiments, the DNA or RNA sequence responsible for a ribosomal frameshift mediates a translational frameshift in the protease in an amount of 90-95% of translated protease mRNA. This results in a small fraction of no more than 20%, preferably 5-10% of the nucleotide sequence that encodes the protease (e.g. 3C protease) downstream of the frameshift element being fully translated with the correct open reading frame.

Frameshifts resulting from ribosomal frameshifting are controlled by various mechanisms found in codons. These mechanisms emerge from the fact that ribosomes do not translate proteins at a steady rate, regardless of the sequence. Certain codons take longer to translate, because there are not equal amounts of tRNA of that particular codon in the cytosol. Due to this lag, there exist in small sections of codons sequences that control the rate of ribosomal frameshifting. Sections of less accessible codons that slow ribosomal transaction are known as "choke points," and sections of easily accessible codons which result in faster ribosomal transaction are "slippery sequences." Slippery sequences can potentially make the reading ribosome "slip" and skip a number of nucleotides (usually only 1) and read a completely different frame thereafter. Choke points reduce the probability of this happening (de Crecy-Lagard, V. *Identification of genes encoding tRNA modification enzymes by comparative genomics*. Methods in Enzymology. 2007 425: 153-83; Green, L., Kim, C. H., Bustamante, C., Tinoco Jr, I. *Characterization of the mechanical unfolding of RNA pseudoknots*. J Mol. Biol. 2008 375(2):511-28; US Patent Publication No. 20120258133—each incorporated herein by reference in its entirety).

In addition to 3C, Leader (L) and 2A proteins of picornaviruses including the FMDV (see FIG. 1) are responsible for proper viral polyprotein processing. Therefore, wild-type and mutant nucleotide sequences that encode the L and 2A proteins may be used to construct the transgene expression cassette described herein for processing of the P1 capsid polyprotein precursor.

To enhance the stability of the final assembled capsid product, mutagenesis strategies and techniques as previously described may be applied to introduce one or more mutations to the nucleotide sequence that encodes the polyprotein precursor. In one or more embodiments, the nucleotide sequence is 2256 nucleotides in length and encodes the P polyprotein precursor derived from the FMDV O1 Manisa isolate 87 strain (serotype O). Among the mutations that can be introduced include silent mutations that effectively eliminate restriction enzyme recognition sites to better facilitate cloning and sub-cloning yet maintain the same translated protein product by not causing any amino acid substitution. These mutations enhance the cloning in and cloning out of the P1 polyprotein precursor into a transgene expression cassette to swap different P1 polyprotein precursors from different FMDV serotypes to promptly respond to the needs of individual outbreaks.

In one or more embodiment, the mutations to the DNA coding sequence of the P polyprotein precursor include changes to one or more of C99, C285, T345, G354, A369, C408, C468, G498, C528, A588, C597, C627, C957, G1170, T1338, T1518, C1578, T1593, C1665, C1836, C2010, A2190 or combinations thereof, from one pyrimidine base to another pyrimidine base, from one purine base to another purine base, or to any other base as long as the mutation does not result in an amino acid change upon translation. In one or more embodiments, the nucleotide substitutions are: C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T or combinations thereof, from one pyrimidine base to another pyrimidine base, from one purine base to another purine base, or to any other base as long as the mutation does not result in an amino acid change upon translation.

Figure 3:
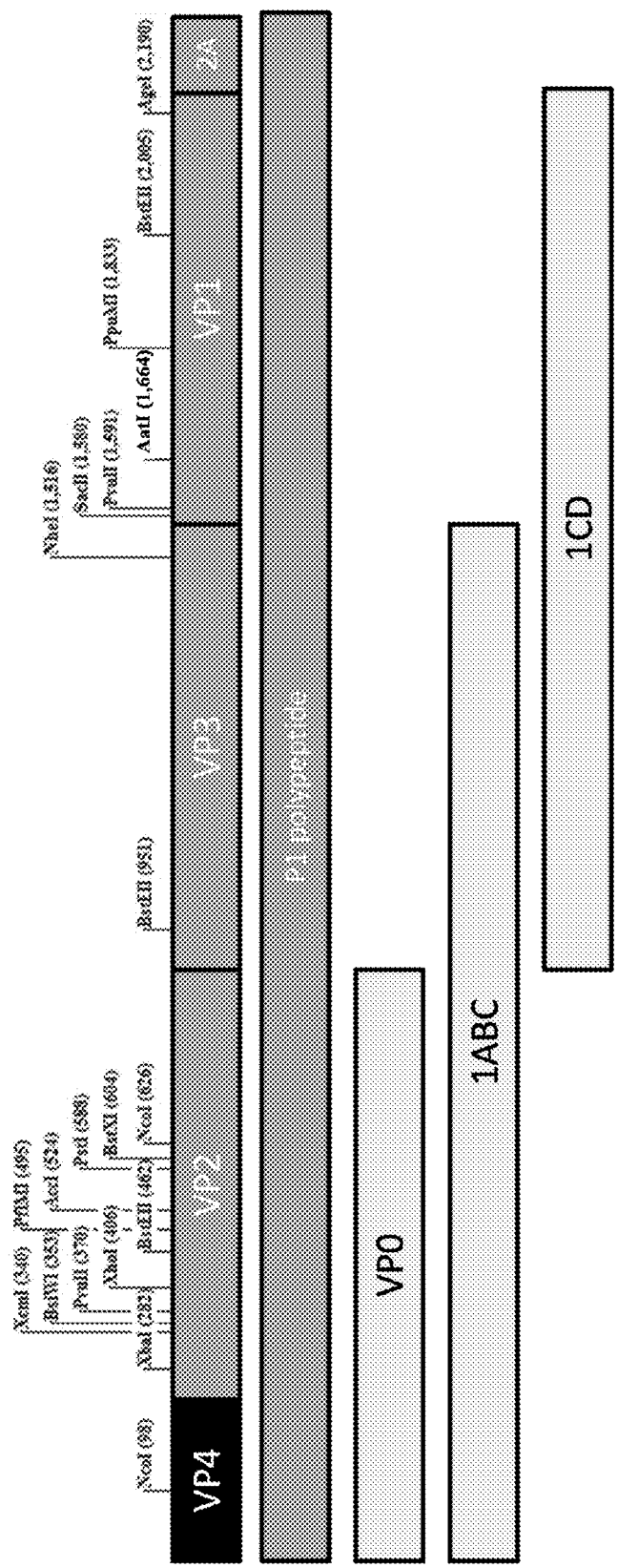
FIG. 3 is a schematic diagram illustrating the locations of multiple restriction enzyme recognition sites in the P1 polyprotein precursor according to one embodiment.

In one or more embodiments, the restriction enzyme recognition sites that are eliminated by the mutations to the P1 polyprotein precursor include, as shown in FIG. 3, XbaI, XcmI, BsiWI, XhoI, BstEII, PflMI, AccI, NheI, SacII, PpuMI, AgeI, PvuII, NcoI, PstI, BstXI and AatI.

To ensure cessation of mRNA translation, a stop codon sequence (i.e., TAA, TGA, or TAG) may be added to the end of the transgene expression cassette.

In one or more embodiments, the mutated P1 polyprotein precursor comprises nucleotide sequence SEQ ID NO: 1. The nucleotide sequence of a wild-type P1 polyprotein precursor derived from FMDV O1 Manisa isolate 87 comprises SEQ ID NO: 11.

In one or more embodiments, the mutated P1 polyprecursor comprises a mutant nucleotide sequence of a P1 polyprecursor derived from any of the seven major FMDV antigenically distinct virus serotypes, i.e., A, O, C, Asia 1 and South African Territories 1, 2 and 3 as well as the multiple subtypes or topotypes exist within each serotype. The wild-type nucleotide sequences of the P1 polyprotein precursor from various FMDV serotypes are known, for example SEQ ID NO: 11 (O1 Manisa isolate 87), SEQ ID NO: 12 (Type A (A/IRN/1/96)), SEQ ID NO: 13 (Type C (Haute Loire FR/69)), SEQ ID NO: 14 (SAT3 ZAM/04/96/3), SEQ ID NO: 15 (SAT2 SEN/05/75), SEQ ID NO: 16 (SAT1 NIG/15/75) and SEQ ID NO: 17 (Asia 1 IND 63/72).

The present disclosure further provides vectors or vehicles containing the transgene expression cassette. Example vectors include, but are not limited to, circular or linear, single- or double-stranded, natural or engineered extrachromosomal plasmid vectors, cosmids, viral vectors, expression vectors, gene transfer vectors, minicircle vectors, and artificial chromosomes and typically contain at least an origin of replication, a cloning site and a selectable marker (e.g., antibiotic resistance). Natural versions of the foregoing examples may be isolated, purified, and/or modified so the resultant natural version is differentiable from the material in its natural state.

In an embodiment, the vector used for transferring the transgene expression cassette is a minicircle DNA vector. A "minicircle DNA vector" may be referred to as "minicircle vector" or "minicircle" is a small (usually in the range of 3-4 kb, approximately 3-4 kb or usually no larger than 10 kb) circular, episomal plasmid derivative wherein all prokaryotic vector parts (e.g., bacterial origin of replication, genes associated with bacterial propagation of plasmids) have been removed. Since minicircle vectors contain no prokaryotic DNA sequences, they are less likely to be perceived as foreign and destroyed when they are employed as vehicles for transferring transgenes into target mammalian cells. In embodiments, a minicircle DNA vector is a minicircle carrying a transgene expression cassette. In examples, a minicircle DNA vector is a minicircle carrying a transgene expression cassette and does not contain an empty vector without an insert.

The use of a minicircle DNA vector to carry and transfer the transgene expression cassette allows mammalian cells to be transfected (e.g., directly) without utilizing an intermediate eukaryotic host system (e.g., insect cell line production system). In embodiments, "transfection" is the process of deliberately introducing nucleic acid into eukaryotic cells, such as animal cells. Transfection can eliminates the costs and labor associated with maintaining large volumes of intermediate host cell cultures in production facilities and harvesting empty capsids or VLPs produced by intermediate host cells.

Furthermore, the size of minicircle vectors (which are smaller than standard plasmid vectors) and the lack of extraneous bacterial sequences enhance transfection of cells and enable an extended duration of transgene expression within the mammalian host cell. For example, a minicircle vector is smaller than a standard vector as it lacks extraneous bacterial sequences found on plasmids. Differences in size between plasmid vectors and minicircle vectors can be attributed to the lack of extraneous bacterial sequences, inclusion of an insubstantial amount of extraneous bacterial sequences in comparison to the overall size of the vector, such as appreciably smaller in comparison to the plasmid, and variations thereof. Prolonged high levels of transgene expression by minicircles in mammalian hosts can also be facilitated by in the incorporation of strong and constitutive promoters such as SV40, CMV, UBC, EFIA, PGK and CAGG.

In one or more embodiments, the nucleotide sequence of a minicircle containing the transgene expression cassette comprises SEQ ID NO: 3.

The present disclosure additionally provides methods of producing minicircle vectors that are capable of inducing production of FMDV virus-like particles in mammalian host cells and methods of vaccinating a mammalian subject with the minicircle vectors.

Minicircle vectors are prepared using a two-step procedure. Firstly, a full-size parental plasmid containing bacterial sequences and transgene is produced in, for example, *Escherichia coli*. While the parental plasmid is still inside the *E. coli* host, the expression of a site-specific recombinase is induced and the prokaryotic or bacterial bone is excised by the enzyme at the recombinase recognition sites. Examples of site-specific recombinases include Tyr- and Ser-recombinases such as Cre recombinase, Flp recombinase, ParA resolvase and PhiC31 integrase. The resulting minicircle vector is recovered by capillary gel electrophoresis. An example of suitable materials, techniques, approaches, and methods are described in U.S. Pat. No. 8,236,548 which is hereby incorporated by reference in its entirety. Further description may be found in Kay et al, *A Robust System for Production of Minicircle DNA Vectors*, Nature Biotechnology, 2010 28:1287-1289, which is hereby incorporated by reference in its entirety.

A vaccine in embodiments in accordance with the present disclosure is a biological composition that provides or improves immunity to an organism to a particular disease. A vaccine may contain an agent, such as a killed, inactivated, weakened or attenuated form of the disease-causing microorganism (e.g., virus, bacteria, fungi, algae), its toxins, surface proteins or recombinant nucleic acid such as DNA, compositions or particles that resemble the pathogenic microorganism (e.g., virus-like particles) or combinations thereof. The agent functions as an antigen and is administered to an organism to stimulate the body's immune system to produce an immune response, which may include recognizing the agent as foreign, destroying the agent (e.g., with antibodies produced that are specific to the agent/antigen), and remembering the agent, so the immune system can more easily recognize and destroy any of these microorganisms that it later encounters, for example, an infection.

Virus-like particles, or VLPs, can be used in accordance with embodiments of the present disclosure. VLPs are recombinant particles with viral matrix or structural proteins such as capsids that resemble viruses, but are non-infectious and unable to propagate as they, respectively, do not contain any viral genetic material. VLPs can be utilized as vaccine antigens as they mimic the native virions, and can be produced in vitro in a variety of cell culture systems including mammalian cell lines, insect cell lines, yeast and plant cells or in vivo. In embodiments, FMDV VLPs consist essentially of assembled structural proteins or assembled capsid proteins (e.g., VP1, VP2, VP3 and VP4).

In DNA vaccination, an organism is protected against a disease by injecting it with genetically engineered DNA (e.g., transgene+vector) to produce an immune response. DNA vaccines have a number of advantages over traditional whole-pathogen vaccines and protein-based vaccines. For example, DNA vaccines do not contain an actual infectious agent, whether dead or alive. DNA vaccines can also be easily lyophilized for long-term storage and transportation and do not require any cold chain delivery.

The DNA vector inside a DNA vaccine can be produced and modified more quickly and more easily in comparision to traditional vaccine preparation. This allows a more rapid response to specifically engineer DNA vaccines tailored to individual FMD outbreaks (e.g., a DNA vaccine matching a specific FMDV outbreak strain or serotype). Using a minicircle DNA vector to carry and transfer the transgene expression cassette eliminates the use of an intermediate eukaryotic host system and the associated costs and labor, including modification of an intermediate host system during and outbreak, such as during the onset of an FMD outbreak.

Routes of DNA vaccine administration include, but are not limited to, traditional injection methods in saline (e.g. subcutaneous, intradermal and intramuscular injections), jet injection, oral administration, skin patches, aerosol inhalation or instillation, topical administration to the eye, electroporation, gene gun, transfection, liposome-mediated delivery or combinations thereof.

An FMD DNA vaccine in accordance with embodiments of the present disclosure are administered at dosages such as in the range of 25-1000 µg of the minicircle DNA vector in saline solution or another appropriate diluent, in the range of between 50-500 µg, in the range of 100-250 µg. A variety of factors can form the basis of what dosage range to implement. Examples of factors that influence dosage amount include, but are not limited to, the size of the subject, how virulent the FMD strain that is being inoculated against is, and so forth. The FMD DNA vaccine and/or the method of vaccinating a mammalian subject with the vaccine protects the subject against one or more of the O, A, C, Asia 1, SAT 1, SAT 2 and SAT 3 serotypes of the FMD virus.

The FMD DNA vaccines formulated with compositions and methods described herein may be used prophylactically (e.g., to prevent or ameliorate the effects of a future infection), therapeutically (e.g., to treat or to empower the immune system of an infected organism) or both.

FMD vaccines in accordance with the present disclosure are marker vaccines or DIVA (Differentiating Infected from Vaccinated Animals), which induce immune responses that differ from those caused by natural infection. These differences are reflected in antibody profiles, and can be detected by diagnostic tests and assays such as enzyme linked immunosorbent assays (ELISAs) containing the same compositions used in the vaccine formulations. The DIVA strategy is useful in eradication scenarios wherein emergency vaccination using DIVA FMD vaccines could be an effective control tool for FMD outbreaks in densely populated livestock areas. DIVA vaccination can limit the number of culled animals in the process of FMD eradication, thereby enhancing public acceptance for disease control measures and limiting economic losses.

The minicircle vector DNA vaccine platform for FMD, as described herein, may be used with or without adjuvants. In certain embodiments, the FMD DNA vaccines further include one or more compounds selected from an adjuvant, a diluent or a carrier. Example adjuvants include, but are not limited to, aqueous-based aluminum hydroxide gel-saponin, the oil-based Montanide ISA 206, other aluminum-based adjuvants and incomplete Freunds adjuvant (IFA). Example diluents include, but are not limited to, water, physiological saline solution, human serum albumin, oils, polyethylene glycols, glycerin, propylene glycol or other synthetic solvents, antibacterial agents such as benzyl alcohol, antioxidants such as ascorbic acid or sodium bisulfite, chelating agents, such as ethylene diamine-tetra-acetic acid, buffers such as acetates, citrates or phosphates and agents for adjusting osmolarity, such as sodium chloride or dextrose.

Example carriers include, but are not limited to, liquid carriers (e.g., water, saline, culture medium, saline, aqueous dextrose, aqueous glycols) and solid carriers (e.g., carbohydrates such as starch, glucose, lactose, sucrose, dextrans; anti-oxidants such as ascorbic acid and glutathione, hydrolyzed proteins).

An FMD DNA vaccine's efficacy in embodiments is considered the rate of reduction in the incidence of serotype-specific FMD among a population of subjects that have been vaccinated compared to the incidence in a population of unvaccinated subjects, over a duration of 12 months. Vaccine efficacy (VE) can measured using the following formula:

$$VE=[(ARU-ARV)/ARU]\times 100\%$$

where "VE" is vaccine efficacy, "ARU" is an attack rate in an unvaccinated population and "ARV" is an attack rate in the vaccinated population.

FMD DNA vaccines comprising the minicircle DNA vector in accordance with the present disclosure exhibit VE values of between 50-95%, approximately 50%, greater than 50/%, 50%, approximately 75%, approximately 75%, greater than 75%, approximately 90%, greater than 90%, 95%, approximately 95%, or greater than 95%.

The examples below are intended to further illustrate protocols for preparing and characterizing the transgene expression cassette and the minicircle vector carrying the transgene expression cassette, and are not intended to limit the scope of the claims. While these examples are provided for explanatory purposes, these should not be considered the only examples. Additional examples will be apparent based on the teachings of the present disclosure.

Example 1

Construction of Inserts and Production of Minicircle Vectors

Figure 4:
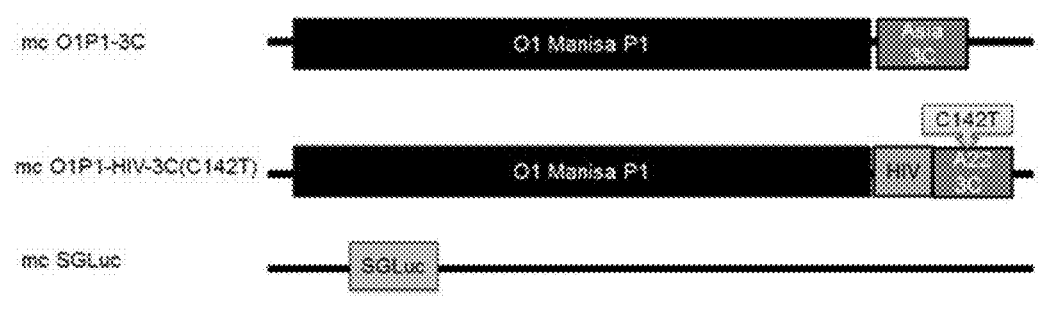

Three insert constructs, as may be seen in FIG. 4 and outlined below, were constructed, individually cloned and evaluated in a minicircie vector system in accordance with this disclosure.

The O1P1-3C(wt) insert (SEQ ID NO: 18) includes the mutant FMDV P1 polypeptide from FMDV 01 Manisa isolate 87 (SEQ ID NO: 1) with a wild-type Asia Lebanon 89 3C protease sequence for processing (SEQ ID NO: 7). This arrangement mirrors that used in FMDV adenovirus vaccine constructs. Examples include Mayr et al., *Immune Responses And Protection Against Foot-And-Mouth Disease Virus (FMDV) Challenge in Swine Vaccinated With Adenovirus-FMDV Constructs*, Vaccine, 2001 19:2152-62; Moraes et al., *Early Protection Against Homologous Challenge After a Single Dose of Replication-Defective Human Adenovirus Type 5 Expressing Capsid Proteins of Foot-And-Mouth Disease Virus (FMDV) Strain A*24, Vaccine, 2002 20:1631-9; Pacheco et al., *Rapid Protection of Cattle From Direct Challenge With Foot-And-Mouth Disease Virus (FMDV) by a Single Inoculation With An Adenovirus-Vectored FMDV Subunit Vaccine*, Virology, 2005 337:205-9. All of the foregoing articles are incorporated by reference in their entirety.

The O1P1-HIV-3C(C142T) insert (SEQ ID NO: 19) utilizes the mutant FMDV P1 polypeptide from FMDV 01 Manisa isolate 87 (SEQ ID NO: 1), the HIV frameshift element (SEQ ID NO: 6) with an A22 Iraq strain 3C protease containing a C142T mutation (SEQ ID NO: 9).

The wild-type nucleotide sequence of FMDV 01 Manisa isolate 87 P1 coding region comprises SEQ ID NO: 11.

The SGLuc insert (SEQ ID NO: 20) expresses the 8990 variant of *Gaussia luciferase* (SGLuc), such as that described in Kim et al., *Superluminescent Variants of Marine Luciferases for Bioassays*, Analytical Chemistry. 2011 83:8732-40, which is hereby incorporated herein by reference in its entirety. The SGLuc insert provides both a negative control for FMDV protein expression and a positive control for transfection efficiency due to its *luciferase* activities.

The Kozak eukaryotic translation initiation nucleotide sequence (SEQ ID NO: 5) is positioned 5' to each of the O1P1-3C(wt) (SEQ ID NO: 18), O1P1-HIV-3C(C142T) (SEQ ID NO: 19) and SGLuc insert constructs (SEQ ID NO: 20). With the O1P1-3C(wt) and O1P1-HIV-3C(C142T) inserts, the Kozak eukaryotic translation initiation nucleotide sequence is positioned 5' to mutant nucleotide sequence of FMDV P1 polypeptide from FMDV 01 Manisa isolate 87 (SEQ ID NO: 1).

To produce the pMC-CMV-SV40-polyA O1P1-HIV-3C (C142T) minicircle vector, the parental plasmid pMC-CMV-MCS-SV40-polyA (System Biosciences, catalog number MN501A-1) was digested with BamHI and EcoRI restriction enzymes according to manufacturer's instructions. The nucleotide sequence for the O1P1-HIV-3C(C142T) construct was synthesized and digested with BamHI and EcoRI restriction enzymes according to manufacturer's instructions for insertion into the pMC.CMV-MCS-SV40-polyA parental plasmid. A ligation reaction was performed using T4 DNA Ligase with a 3:1 insert to vector ratio as per manufacturer's instructions.

A ligation reaction was used to transform 5-alpha Competent *E. coli* (High Efficiency) as per manufacturer's instructions. The cells were plated on 50 µg/mL Kanamycin LB agar plates. Colonies were picked and grown in growth medium with kanamycin, overnight in a 37° C. shaker. Plasmids were purified using a miniprep kit according to manufacturer's protocols. Sequencing was performed to confirm mutation free insertion using the following primers: O1 MSeq1-F (SEQ ID NO: 21), O1MSeq2-F (SEQ ID NO: 22), O1MSeq3-F (SEQ ID NO: 23), 01 MSeq4-F (SEQ ID NO: 24), O1MSeq5-F (SEQ ID NO: 25), O1MSeq6-F (SEQ ID NO: 26), O1MSeq7-F (SEQ ID NO: 27), O1MSeq8-F (SEQ ID NO: 28), O1P1-Seq-R1 (SEQ ID NO: 29) and O1P1-Seq-R2 (SEQ ID NO: 30).

Alternatively, competent *E. coli* cells from the ZYCY10P3S2T *E. coli* strain were transformed by adding DNA from the ligation reaction to the competent cells that have been thawed on ice, incubating the cells on ice for 30 minutes (min), heat-shocking the cells for 30 s in a 42° C. water bath without shaking and placing the cells on ice again for 2 min. The transformed *E. coli* cells were recovered by adding 0.2 ml of room temperature Super Optimal Broth with Catabolit repression (SOC) medium to the cells and incubating at 30° C. or 37° C. for 60-90 min with shaking at 250 revolutions per minute (rpm). After that, the transformants were selected on LB plates containing 50 µg/µl kanamycin and 10 mM L-arabinose. Transformants that formed colonies after the overnight incubation had their minicircle vectors extracted by standard miniprep. The extracted minicircle vector samples were examined by restriction digest analysis and sequencing with the aforementioned primers.

The ZYCY10P3S2T *E. coli* strain harbors an arabinose-inducible system to express the PhiC31 integrase and I-SceI endonuclease (both integrase and endonuclease genes are found on the parental plasmid). The PhiC31 integrase excises the prokaryotic parts from the parental plasmid, thus forming a "bacterial backbone" and the pMC-CMV-SV40-polyA O1P1-HIV-3C(C142T) minicircle vector containing the transgene expression cassette. In one or more embodiments, the nucleotide sequence of the "bacterial backbone" and the pMC-CMV-SV40-polyA O1P1-HIV-3C(C142T) minicircle vector containing the transgene expression cassette comprises SEQ ID NO: 31. The bacterial backbone, containing signals for methylation transgene silencing, is recognized and ultimately degraded by the expressed I-SceI endonuclease. The elements that remain in the polyA O1P1-HIV-3C(C142T) minicircle vector include the Cytomegalovirus (CMV) promoter to drive high and sustained levels of gene expression and the Simian virus 40 (SV40) PolyA signal for transcription termination. In one or more embodiments, the pMC-CMV-SV40-polyA O1P1-HIV-3C(C142T) minicircle vector containing the transgene expression cassette comprises SEQ ID NO: 3.

To create the O1P1-3C(wt) construct the previously constructed O1P1-HIV-3C(C142T) construct was digested with NotI and EcoRI restriction enzymes according to manufacturer's instructions. PCR was performed according to manufacturer's instructions with primers NotI-3CLeb89-F (SEQ ID NO: 32) and 3CLeb89-EcoRI-R (SEQ ID NO: 33) using a template plasmid containing the 3C nucleotide sequence from FMDV Asia Lebanon 1989 strain. PCR product was digested with NotI and EcoRI restriction enzymes according to manufacturer's instructions. Ligation, transformation, plasmid purification, and sequencing were performed as described above. In one or more embodiments, the nucleotide sequence of the "bacterial backbone" and the pMC-CMV-SV40-polyA O1P-3C(wt) minicircle vector containing the transgene expression cassette comprises SEQ ID NO: 34. In one or more embodiments, the pMC-CMV-SV40-polyA O1P1-3C(wt) minicircle vector containing the transgene expression cassette comprises SEQ ID NO: 35.

To create the SGLuc construct a pTarget construct containing the SGLuc nucleotide coding sequence was digested with BamHI and EcoRI restriction enzymes according to manufacturer's instructions. Ligation, transformation, and plasmid purification was performed as described above. Sequencing was performed using primers AscI-Kzk-Gluc-F (SEQ ID NO: 36) and Gluc-R-NotI (SEQ ID NO: 37). In one or more embodiments, the "bacterial backbone" and the pMC-CMV-SV40-polyA SGLuc minicircle vector containing the transgene expression cassette comprises SEQ ID NO: 38. In one or more embodiments, the pMC-CMV-SV40-polyA SGLuc minicircle vector containing the transgene expression cassette comprises SEQ ID NO: 39.

Example 2

Transfection of the Minicircle Vectors into Mammalian Cells and VLP Production

The pMC-CMV-SV40-polyA O1P1-3C(wt) (SEQ ID NO: 35), pMC-CMV-SV40-polyA O1P1-HIV-3C(C142T) (SEQ ID NO: 3) and pMC-CMV-SV40-polyA SGLuc (SEQ ID NO: 39) minicircle vectors produced in Example 1 were transfected into the mammalian cell line LF-BK αV/β6 using a commercially available transfection reagent. LF-BK αV/β6 cells were cultivated in six well plates until 95% confluent. Transfections were performed with 4 µg of minicircle DNA according to the manufacturer's protocol. Additionally, HEK293-T cells at passage 71 at roughly 90% confluence were transfected with the minicircle vectors using a transfection reagent and 4 µg of the minicircle vectors as per manufacturer's instructions. Transfected cell cultures were allowed to sit at 37° C. for 24 hour (h) in a $CO_2$ incubator.

Example 3

Evaluation of Expression by *Luciferase* Assay

Figure 5:
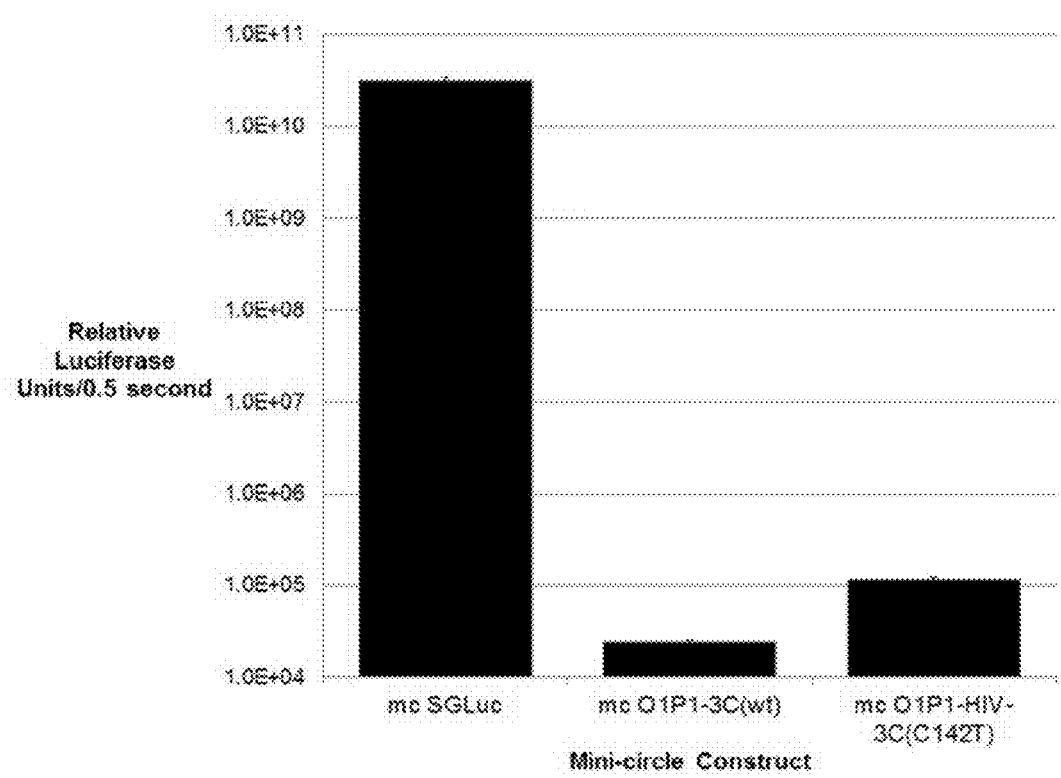
FIG. 5 is a bar graph of *luciferase* reading from cell culture media harvested off of transfected HEK239-T cells. The Y axis represents Relative *Luciferase* Units (RLU)/0.5 second (s), and the X axis represents the mc SGLuc, mc O1P1-3C(wt) and mc O1P1-HIV-3C(C142T) Mini-circle Constructs.

To evaluate expression of the pMC-CMV-SV40-polyA SGLuc minicircle vector, a *luciferase* assay was utilized to detect for luminescence. A luminescence assay was performed on a 96-well luminometer using 20 dl of harvested media without delay after injection of 25 µl of 100 µM water soluble coelenterazine solution and an integration of 0.5 s. Readings were taken both before and after injection of coelenterazine. During analysis of the data, readings for before injection were used to establish a baseline of light emission at the time of injection and were subsequently subtracted from post-injection values. Replicates were averaged together to give an overall *luciferase* reading in relative *luciferase* units per half second (RLU/0.5 s). Media from transfected HEK293-T cells was harvested and checked for *luciferase* activity to confirm transfection, as shown in FIG. 5. As expected only cells transfected with the SGLuc insert construct showed *luciferase* activity.

Example 4

Evaluation of Expression and P1 Processing by Western Blotting

Figure 6:
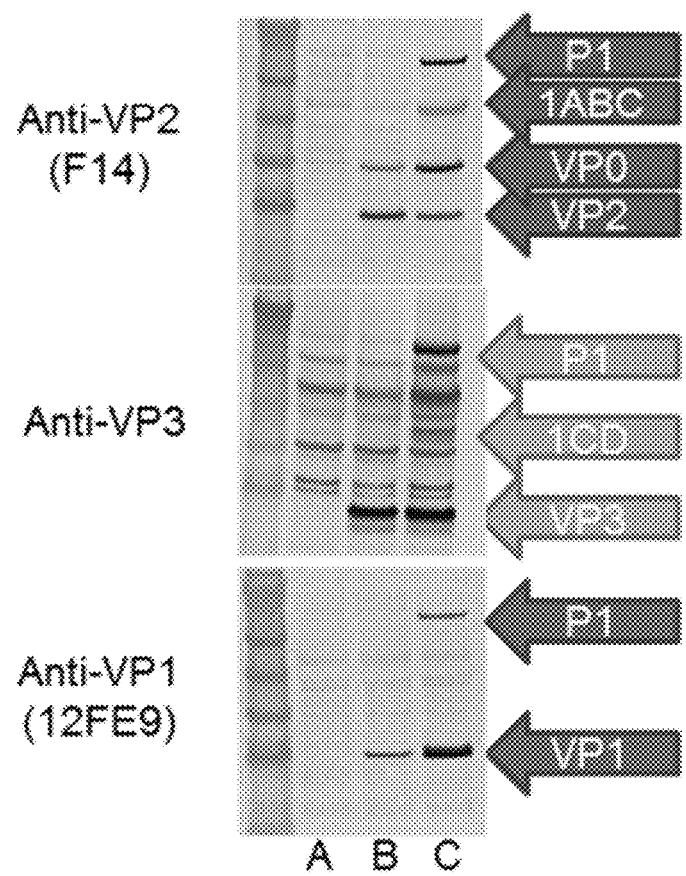
FIG. 6 is a western blotting image of transfected cells reacted with F14 anti-VP2, anti-VP3 and 12FE9 antibodies to examine FMDV P1 processing in transfected cells.

Transfected HEK293-T cells lysates was examined by western blotting to confirm expression and processing of FMDV proteins as shown in FIG. 6. Three different antibodies were used to examine processing. Each of the antibodies was chosen to react with a different capsid protein. Two mouse monoclonal antibodies, F14 and 12FE9, and one rabbit polyclonal antibody against FMDV VP3 were used. The F14 mouse monoclonal antibody reacts with the FMDV VP2 protein while the 12FE9 mouse monoclonal antibody reacts with VP1.

To evaluate processing, transfected cell lysates were harvested from 6 well plates using 250 id of mammalian protein extraction reagent. Samples were mixed with a loading buffer to make a final concentration of 1×. 16 µl of the mixed samples were loaded onto 4-12% Bis-Tris protein gels and run according to manufacturer's instructions. Transfer of the protein gel to membranes was performed using a western blot.

Membranes were incubated in 5% milk blocking buffer solution for 1 h while shaking at room temperature. Membranes were rinsed two times with 1×PBS-T and washed for five min with 1×PBS-T while shaking at room temperature. Primary antibodies were diluted in 1×-PBS-T and applied to membranes for 1 h at room temperature. Primary antibodies used were 1:50 mouse monoclonal F14 (anti-VP2), 1:250 rabbit polyclonal anti-VP3, and 1:50 mouse monoclonal 12FE9 (anti-VP1). After incubation membranes were washed for five min with PBS-T for three times. Secondary antibodies were diluted in 1×PBS-T and applied to the membranes for 1 h at room temperature. Secondary antibodies used are a 1:500 dilution ratio of goat HRP conjugated anti-mouse (KPL) and a 1:500 dilution ratio of goat HRP conjugated anti-rabbit. After incubation membranes were washed for five min with PBS-T for three times. A solution of 3',3'-Diaminobenzidine made using 3,3'-Diaminobenzidine tablets was applied to membranes and incubated while shaking at room temperature until the appearance of bands.

As shown in FIG. 6, examination of cell lysates from cells transfected with the O1P1-3C(wt) construct shows full processing of all 3C dependent junctions. VP0 is present in O1P1-3C(wt) cell lysate. However the band is less intense than that of the VP2 band suggesting that there is a greater concentration of fully processed VP2 than unprocessed VP0 in the sample. Still referring to FIG. 6, the O1P1-HIV-3C (C142T) insert construct does not show complete processing of VPs as confirmed through the presence of detectable levels of unprocessed intermediates. The only unprocessed intermediate not observed is a 1ABCD fusion which would be hard to differentiate from the P1 polypeptide on the blots due to high and similar molecular weights. Additionally we see a more intense band representing VP0 than representing VP2 suggesting that there is more unprocessed VP0 in the sample than that of VP2, an inversion of what is observed with the O1P1-3C(wt) construct.

Given that the HIV-1 frameshift sequence reduces overall expression of 3C in the O1P1-HIV-3C(C142T) construct the presence of unprocessed intermediates is not surprising. The reduction of 3C expression lowers the level of 3C present which can process host proteins providing a benefit to the host cell. However it also reduces the amount of 3C available to process the FMDV VPs.

Example 5

Evaluation of Transfected Cells by Immunofluorescent Antibody Staining (IFA) and Transmission Electron Microscopy (TEM)

As the presence of processed P1 does not ensure the formation of VLPs, transfected LF-BK αV/β6 cells were examined at 24 and 48 h post-transfection using IFA staining and TEM to confirm the production of FMDV VLPs. An electron microscopy image showing FMDV VLPs in crystalline array is shown in FIG. 7.

HEK293-T cells were incubated to adhesion on a collagen coated slide, dried, then fixed at −20° C. with 1:1 acetone: methanol. Samples were blocked with 10% FBS in PBS. Antibody 12FE9 was used at a 1:10 dilution for primary staining. Secondary staining used 1:250 anti-mouse secondary antibody. Mounting media with DAPI (Molecular Probes P36935) was applied.

HEK293-T cells were grown in T-75 flasks for transmission electron microscopy (TEM). Cells were fixed in 2% glutaraldehyde in NaHCa (Heuser's) buffer, post-fixed with 1% tannic acid followed by 1% osmium tetroxide, en-bloc stained with 4% uranyl acetate, embedded in 2% agarose, dehydrated through graded series of acetone, and embedded in Spurr's resin. Ultrathin (80 nm) sections were cut on a ultramicrotome (e.g., Leica UC6), stained with uranyl acetate and lead citrate, and imaged on a transmission electron microscope (e.g. Hitachi 7600) with a 2k×2 k AMT camera at 80 kV.

Figure 7:
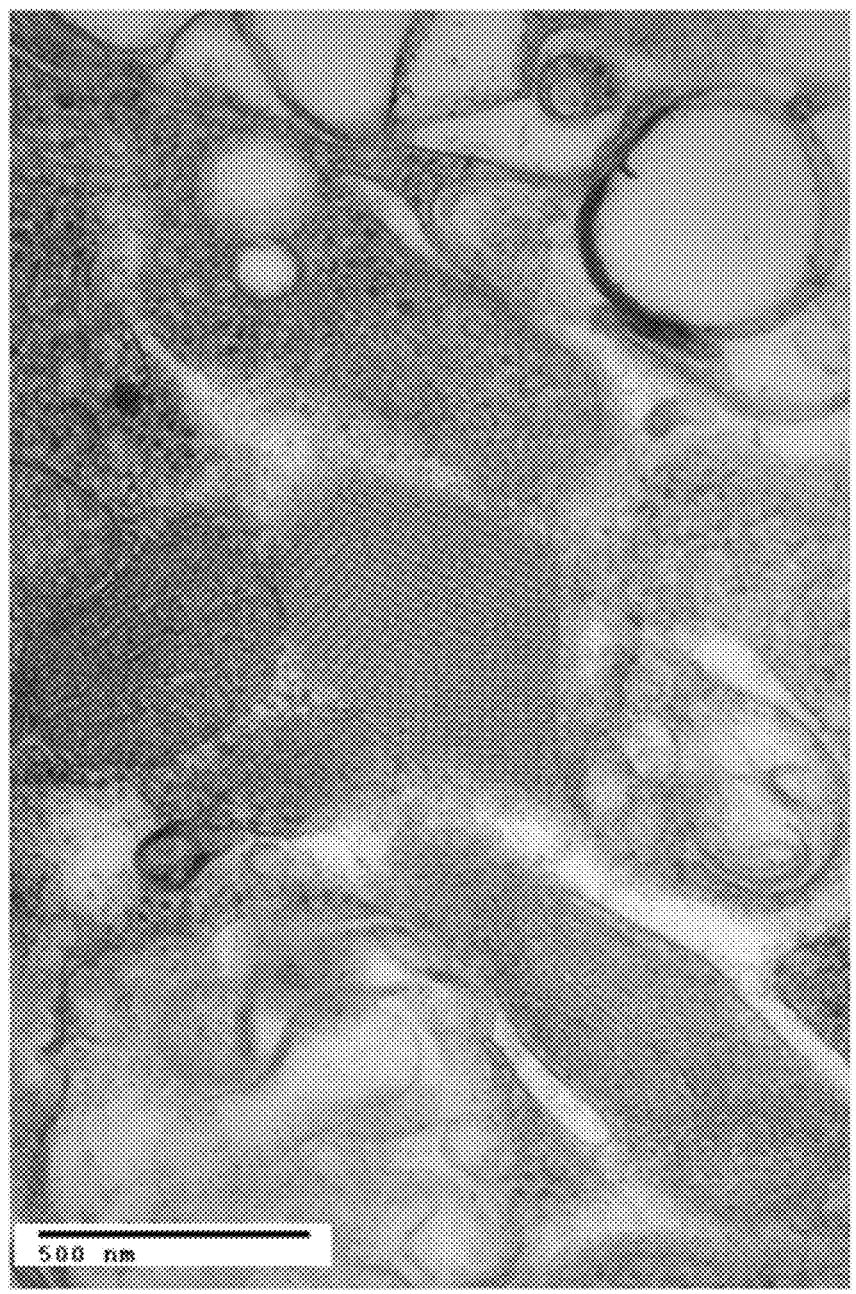
FIG. 7 is a transmission electron microscopy image showing formation of FMDV VLP arrays of HEK293-T cells transfected with pMC-CMV-SV40-polyA O1P1-3C (wt) minicircles.
Figure 8A:
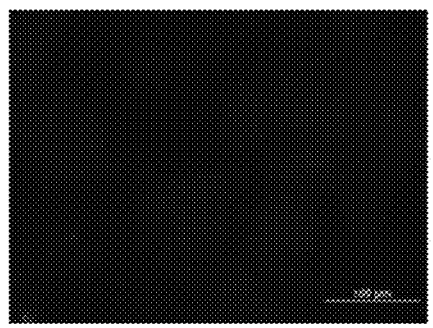
FIG. 8A is an image of IFA staining of HEK293-T cells transfected with pMC-CMV-SV40-polyA SGLuc minicircles using 12FE9 antibody.

Similarly, to confirm the presence of VLPs generated off of minicircles, transfected HEK293-T cells were examined using TEM (see FIG. 7). IFAs were performed on transfected cells to ensure the presence of expressed proteins in transfected cell lines (see FIGS. 8A-8C). The IFAs showed expression of FMDV proteins in both constructs that contained the FMDV P1 polypeptide (FIGS. 8B and 8C) and no expression in cells transfected with the mc SGLuc construct (FIG. 8A). This is in agreement with results seen in previously performed western blots in FIG. 6.

Fluorescence in the pMC-CMV-SV40-polyA O1P1-3C (wt) samples was localized largely in aggregates while fluorescence in pMC-CMV-S0-polyA O1P1-HIV-3C (C142T) samples was much more diffused through the whole cell. This suggests that transgene expression in O1P1-3C(wt) transfected samples is more structured and localized.

Figure 8B:
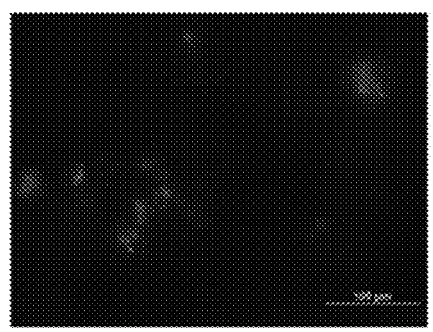
FIG. 8B is an image of IFA staining of HEK293-T cells transfected with pMC-CMV-SV40-polyA O1P1-3C(wt) minicircles using 12FE9 antibody.
Figure 8C:
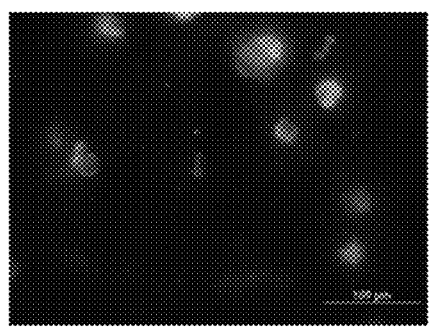
FIG. 8C is an image of IFA staining of HEK293-T cells transfected with pMC-CMV-SV40-polyA O1P1-HIV-3C (C142T) minicircles using 12FE9 antibody.

In FIG. 7, the transmission electron microscopy image shows formation of FMDV VLP arrays of HEK293-T cells transfected with pMC-CMV-SV40-polyA O1P1-3C(wt). This aligns with the difference in fluorescence distribution between pMC-CMV-SV40-polyA O1P1-3C(wt) and pMC-CMV-SV40-polyA O1P1-HIV-3C(C142T) samples as seen in FIGS. 8B and 8C, respectively. This difference in distribution is also probably related to the lack of complete processing observed in pMC-CMV-SV40-polyA O1P1-HIV-3C(C142T) samples in FIG. 6. The observance of VLP arrays in the pMC-CMV-S0-polyA O1P1-3C(wt) sample does confirm that VLP formation using a minicircle vector is viable. Previous publications using the HIV frameshift in conjunction with the FMDV 3C, (Porta C, Xu X, Loureiro S, Paramasivam S, Ren J, Al-Khalil T, et al. *Efficient production of foot-and-mouth disease virus empty capsids in insect cells following down regulation of 3C protease activity*. Journal of Virological Methods. 2013 187:406-12, incorporated herein by reference in its entirety), observed VLPs after utilizing sucrose gradient purification to concentrate any VLPs produced prior to observation with TEM. It is possible that this additional purification and subsequent concentration of the samples aids in VLP detection by TEM.

The foregoing discussion discloses embodiments in accordance with the present disclosure. As will be understood by those skilled in the art, the approaches, methods, techniques, materials, devices, and so forth disclosed herein may be embodied in additional embodiments as understood by those of skill in the art, it is the intention of this application to encompass and include such variation. Accordingly, this disclosure is illustrative and should not be taken as limiting the scope of the following claims.

What is claimed:

1. A mutant nucleotide sequence that encodes a foot-and-mouth disease virus (FMDV) capsid polyprotein precursor derived from a FMDV, the mutant nucleotide sequence comprising a mutation that removes a restriction enzyme recognition site, and comprising the nucleotide sequence of SEQ ID NO: 1.

2. A vector comprising a mutant nucleotide sequence that encodes a foot-and-mouth disease virus (FMDV) capsid polyprotein precursor that includes a mutation that removes a restriction enzyme recognition site, wherein the mutant nucleotide sequence comprises the nucleotide sequence of SEQ ID NO: 1.

3. A vector comprising a mutant nucleotide sequence that encodes a foot-and-mouth disease virus (FMDV) capsid polyprotein precursor that includes a mutation that removes a restriction enzyme recognition site, wherein the vector comprises the nucleotide sequence of SEQ ID NO: 2.

4. A vector comprising a mutant nucleotide sequence that encodes a foot-and-mouth disease virus (FMDV) capsid polyprotein precursor that includes a mutation that removes a restriction enzyme recognition site, further comprising:
   a eukaryotic translation initiation nucleotide sequence positioned 5' to the mutant nucleotide sequence;
   a nucleotide sequence that encodes a protease; and
   a translational regulatory element positioned 3' to the mutant nucleotide sequence and 5' to the nucleotide sequence that encodes the protease, and
   wherein the vector comprises the nucleotide sequence of SEQ ID NO: 3.

5. A vector comprising a mutant nucleotide sequence that encodes a foot-and-mouth disease virus (FMDV) capsid polyprotein precursor that includes a mutation that removes a restriction enzyme recognition site, further comprising:
   a eukaryotic translation initiation nucleotide sequence positioned 5' to the mutant nucleotide sequence;
   a nucleotide sequence that encodes a protease, and
   a translational regulatory element positioned 3' to the mutant nucleotide sequence and 5' to the nucleotide sequence that encodes the protease,
   wherein the translational regulator element comprises a DNA or RNA sequence responsible for a ribosomal frameshift, and
   wherein the DNA or RNA sequence responsible for a ribosomal frameshift comprises the nucleotide sequence of SEQ ID NO: 6.

6. A vector comprising a mutant nucleotide sequence that encodes a foot-and-mouth disease virus (FMDV) capsid polyprotein precursor that includes a mutation that removes a restriction enzyme recognition site, further comprising:
   a eukaryotic translation initiation nucleotide sequence positioned 5' to the mutant nucleotide sequence;
   a nucleotide sequence that encodes a protease; and
   a translational regulatory element positioned 3' to the mutant nucleotide sequence and 5' to the nucleotide sequence that encodes the protease,
   wherein the nucleotide sequence that encodes the protease comprises the nucleotide sequence of SEQ ID NO: 7.

7. A vector comprising a mutant nucleotide sequence that encodes a foot-and-mouth disease virus (FMDV) capsid polyprotein precursor that includes a mutation that removes a restriction enzyme recognition site, further comprising:
   a eukaryotic translation initiation nucleotide sequence positioned 5' to the mutant nucleotide sequence;
   a nucleotide sequence that encodes a protease; and
   a translational regulatory element positioned 3' to the mutant nucleotide sequence and 5' to the nucleotide sequence that encodes the protease,
   wherein the nucleotide sequence that encodes the protease comprises the nucleotide sequence of SEQ ID NO: 9.

\* \* \* \* \*